United States Patent
Wang et al.

(10) Patent No.: US 7,399,903 B2
(45) Date of Patent: Jul. 15, 2008

(54) VESICLE TRAFFICKING STRESS-RELATED POLYPEPTIDES AND METHODS OF USE IN PLANTS

(75) Inventors: Xi-Qing Wang, Chapel Hill, NC (US); Damian Allen, Cary, NC (US); Chen Ruoying, Apex, NC (US); Lori V. Mills, Willow Springs, NC (US); Nocha van Thielen, Durham, NC (US); Oswaldo da Costa e Silva, Neustadt (DE); Bryan McKersie, Raleigh, NC (US)

(73) Assignee: BASF Plant Science GmbH (DE)

( * ) Notice: Subject to any disclaimer, the term of this patent is extended or adjusted under 35 U.S.C. 154(b) by 0 days.

(21) Appl. No.: 11/666,828

(22) PCT Filed: Oct. 27, 2005

(86) PCT No.: PCT/US2005/038805

§ 371 (c)(1),
(2), (4) Date: Apr. 27, 2007

(87) PCT Pub. No.: WO2006/050038

PCT Pub. Date: May 11, 2006

(65) Prior Publication Data

US 2008/0005808 A1 Jan. 3, 2008

Related U.S. Application Data

(60) Provisional application No. 60/522,708, filed on Oct. 29, 2004.

(51) Int. Cl.
- *A01H 5/00* (2006.01)
- *C12N 5/14* (2006.01)
- *C12N 15/82* (2006.01)
- *C12N 15/63* (2006.01)
- *C07H 21/04* (2006.01)

(52) U.S. Cl. ............... 800/295; 435/320.1; 435/468; 536/23.1; 800/278; 800/312; 800/320

(58) Field of Classification Search .............. None
See application file for complete search history.

(56) References Cited

FOREIGN PATENT DOCUMENTS

WO   WO-01/77161 A2   10/2001

OTHER PUBLICATIONS

Reddy et al. (EMBL Database, Sequence Accession No. BI306675, Published Jul. 31, 2001, Applicant's IDS).*
Maniatis et al. (Molecular Cloning: A Laboratory Manual, Cold Spring Harbor Laboratory, 1982).*
Borg et al., NCBI, Sequence Accession No. Z73932, pp. 1-2, Published Jun. 6, 1996.*
"Physcomitrella patens subsp. patens cDNA clone: pph5e02, 5' end, single read", EMBL-EBI Database Accession No. BJ157779, Jan. 22, 2002.
"NL_5_K18 Drought stress (leaf) Oryza sativa cDNA clone NL_5_k18 3', mRNA sequence", EMBL-EBI Database Accession No. BI306675, Jul. 31, 2001.
"Cicer arietinum mRNA for rab-type small GTP-binding protein, complete cds.", EMBL-EBI Database Accession No. AB024994, Apr. 6, 1999.
"Rab-type small GTP-binding protein", NCBI Database Accession No. Q9SXT5, May 1, 2000.
"Pisum sativum mRNA for GTP-binding protein, complete cds, clone: pra9A", EMBL-EBI Database Accession No. D12548, Jul. 7, 1993.
"GTP-binding protein", NCBI Database Accession No. Q08153, Nov. 1, 1996.
"Cell proliferation-related polypeptide #138", EMBL-EBI Database Accession No. ADQ37155, Oct. 7, 2004.
"Rice stress-related protein #74", EMBL-EBI Database Accession No. ADQ15739, Oct. 7, 2004.
"Physcomitrella patens subsp. patens cDNA clone: pphf26a22, 5' end", EMBL-EBI Database Accession No. BJ944582, Jun. 9, 2005.
Shinozaki, K., et al., "Molecular responses to dehydration and low temperature: differences and cross-talk between two stress signaling pathways", Current Opinion in Plant Biology, 2000, vol. 3, pp. 217-223.
Takai, Y., et al., "Small GTP-binding proteins", Physiological Reviews, 2001, vol. 81, No. 1, pp. 153-208.
Vernoud, V., et al., "Analysis of the small GTPase gene superfamily of Arabidopsis", Plant Physiology, 2003, vol. 131, pp. 1191-1208.
Geelen, D., et al., "The abscisic acid-related SNARE homolog NtSyr1 contributes to secretion and growth: evidence from competition with its cytosolic domain", The Plant Cell, 2002, vol. 14, pp. 387-406.
Bolte, S., et al., "Characterization of a small GTP-binding protein of the rab 5 family in *Mesembryanthemum crystallinum* with increased level of expression during early salt stress", Plant Molecular Biology, 2000, vol. 42, pp. 923-936.
O'Mahony, P. J., et al., "Characterization of a desiccation-responsive small GTP-binding protein (Rab2) from the desiccation-tolerant grass *Sporobolus stapfianus*", Plant Molecular Biology, 1999, vol. 39, pp. 809-821.
Mazel, A., et al., "Induction of salt and osmotic stress tolerance by overexpression of an intracellular vesicle trafficking protein AtRab7 (AtRabG3e)", Plant Physiology, 2004, vol. 134, pp. 118-128.

* cited by examiner

*Primary Examiner*—Phuong T Bui
*Assistant Examiner*—Vinod Kumar
(74) *Attorney, Agent, or Firm*—Patricia A. McDaniels

(57) ABSTRACT

A transgenic plant transformed by a Vesicle Trafficking Stress-Related Polypeptide (VTSRP) coding nucleic acid, wherein expression of the nucleic acid sequence in the plant results in the plant's increased growth and/or increased tolerance to environmental stress as compared to a wild type variety of the plant. Also provided are agricultural products, including seeds, produced by the transgenic plants. Also provided are isolated VTSRPs, and isolated nucleic acid coding VTSRPs and vectors and host cells containing the latter.

26 Claims, 4 Drawing Sheets

*Nucleotide sequence of PpVTP-1 from Physcomitrella patents* (SEQ ID NO:1)
CCCAGAAGGCCGATCCGAAAGAAAGGCACCATGAATCCCGAATATGATTACCTTTT
CAAGCTGTTGCTGATCGGAGACTCCGGTGTTGGAAAGAGTTGCCTTCTGCTACGATT
TGCAGACGACTCGTACCTGGAGAGCTACATCAGCACAATCGGTGTGGACTTTAAAAT
ACGTACGGTGGAGCTGGACGGGAAGACCATCAAGTTGCAGATTTGGGATACTGCTG
GTCAGGAGAGGTTCCGGACCATCACAAGCAGCTACTATCGTGGAGCGCACGGGATC
ATTGTTGTGTACGACGTGACAGACCAGGAGAGCTTCAACAACGTGAAGCAATGGTT
GAGTGAGATCGACCGGTACGCGAGCGAGAACGTGAACAAGCTGCTGGTGGGCAACA
AGTCAGATCTGGCGTCGAAGAAGGTGGTGGATTATGCAACTGCAAAGGCATTTGCG
GACGAGATTGGGATTCCGTTTTTGGAGACGAGTGCGAAGAATGCTACGAACGTGGA
GCAGGCGTTTATGACAATGGCAGCGGAGATCAAGAACAGGATGGCGAGTCAGCCCG
CGTTGAGCAGCACAAGCAGGCCGAACAATGTGACGAACCTGCGAGGACAGGCTATT
CCGCAGAAGAGTGGGTGCTGCTCA

*Deduced amino acid sequence of PpVTP-1 from Physcomitrella patents* (SEQ ID NO:2)
MNPEYDYLFKLLLIGDSGVGKSCLLLRFADDSYLESYISTIGVDFKIRTVELDGKTIKLQI
WDTAGQERFRTITSSYYRGAHGIIVVYDVTDQESFNNVKQWLSEIDRYASENVNKLLVG
NKSDLASKKVVDYATAKAFADEIGIPFLETSAKNATNVEQAFMTMAAEIKNRMASQPA
LSSTSRPNNVTNLRGQAIPQKSGCCS

*Nucleotide sequence of PpGBP-1 from Physcomitrella patents* (SEQ ID NO:3)
CCCGGGTCCGTAGATACCAAGGCTGGTACCATGTTTCTTGTAGATTGGTTTTACGGC
TTTCTTGCGAGCATAGGGCTGTGGCAGAAGGAGGCCAAAATCCTGTTTCTGGGTCTC
GACAATGCTGGCAAGACTACTCTTCTGCACATGCTCAAGGATGAGAAACTGGGGCA
ACATCAACCAACGCAGTATCCAACGTCAGAGGAGTTGAGTATCAACAGAGTGAAGT
TCAAAGCATTCGATCTGGGTGGCCACACAATCGCTCGACGCGTGTGGAGGGACTACT
ATGCTAAGGTGGATGCTATAGTGTATCTCGTCGACGCAGTAGACAGGGAGAGATTT
GCTGAGTCAAAGAAAGAGCTCGATTCTCTTCTCCGACGATTCTCTGTCCCAAGTT
CCTGTGCTCGTCCTGGGAAACAAGATTGATATCCCGTACGCTTCTTCTGAAGACGAG
TTGCGGTTCACACTTGGGTTGACCATGACCACTGGTAAAGGAACGGTGAACCTGGG
AGATAGCAACATTCGGCCCATTGAGGTTTTCATGTGCAGTATTGTGCGCAAAATGGG
GTACGGTGAAGGTTTCAAGTGGATGACCCAGTACATCAAG

*Deduced amino acid sequence of PpGBP-1 from Physcomitrella patents* (SEQ ID NO:4)
MFLVDWFYGFLASIGLWQKEAKILFLGLDNAGKTTLLHMLKDEKLGQHQPTQYPTSEE
LSINRVKFKAFDLGGHTIARRVWRDYYAKVDAIVYLVDAVDRERFAESKKELDSLLSD
DSLSQVPVLVLGNKIDIPYASSEDELRFTLGLTMTTGKGTVNLGDSNIRPIEVFMCSIVRK
MGYGEGFKWMTQYIK

FIGURE 3 Cont'd

*Nucleotide sequence of ScVTP-1 from Saccharomyces cerevisiae* (SEQ ID NO:5)
ATGAGTTCCCTATTAATATCATACGAATCTGACTTCAAAACAACCTTAGAACAAGCC
AAAGCGAGCTTAGCAGAGGCCCCCTCACAACCGTTATCACAGAGAAATACTACACT
GAAGCACGTAGAACAGCAACAAGATGAGTTGTTTGACCTGCTAGATCAGATGGATG
TAGAAGTTAATAACAGCATAGGCGATGCCTCAGAACGTGCTACGTACAAGGCGAAG
TTAAGAGAATGGAAGAAGACTATACAGAGCGATATCAAACGACCACTGCAATCCTT
AGTAGACTCAGGCGATCGTGATAGACTTTTTGGAGATCTTAACGCATCTAATATTGA
CGATGACCAAAGGCAACAGTTGTTGAGCAACCATGCAATCTTACAGAAATCGGGAG
ATAGACTAAAAGATGCCAGTAGAATAGCAAATGAAACTGAAGGAATAGGGTCACA
AATAATGATGGATTTAAGGTCACAGAGAGAAACTTTGGAAAATGCAAGACAGACCT
TGTTTCAAGCGGATTCATATGTGGATAAAAGTATAAAGACACTAAAAACAATGACT
AGAAGGCTAGTTGCTAATAAATTCATAAGCTATGCCATTATCGCAGTCCTTATATTA
TTGATTTTGCTAGTTTTGTTCTCAAAGTTTAAATAA

*Deduced amino acid sequence of YMR197C Chr13 ORF3240 from Saccharomyces cerevisiae*
(SEQ ID NO:6)
MSSLLISYESDFKTTLEQAKASLAEAPSQPLSQRNTTLKHVEQQQDELFDLLDQMDVEV
NNSIGDASERATYKAKLREWKKTIQSDIKRPLQSLVDSGDRDRLFGDLNASNIDDDQRQ
QLLSNHAILQKSGDRLKDASRIANETEGIGSQIMMDLRSQRETLENARQTLFQADSYVD
KSIKTLKTMTRRLVANKFISYAIIAVLILLILLVLFSKFK

VESICLE TRAFFICKING STRESS-RELATED POLYPEPTIDES AND METHODS OF USE IN PLANTS

CROSS-REFERENCE TO RELATED APPLICATIONS

This application is a national stage application (under 35 U.S.C. 371) of PCT/US2005/038805 filed Oct. 27, 2005, which claims the benefit of U.S. Provisional Application 60/522,708 filed Oct. 29, 2004.

BACKGROUND OF THE INVENTION

1. Field of the Invention

This invention relates generally to nucleic acid sequences encoding polypeptides that are associated with abiotic stress responses and abiotic stress tolerance in plants. In particular, this invention relates to nucleic acid sequences encoding polypeptides that confer upon the plant increased growth and/or increased drought, cold, and/or salt tolerance.

2. Background Art

Abiotic environmental stresses, such as drought stress, salinity stress, heat stress, and cold stress, are major limiting factors of plant growth and productivity. Crop losses and crop yield losses of major crops such as soybean, rice, maize (corn), cotton, and wheat caused by these stresses represent a significant economic and political factor and contribute to food shortages in many underdeveloped countries.

Plants are typically exposed during their life cycle to conditions of reduced environmental water content. Most plants have evolved strategies to protect themselves against these conditions of desiccation. However, if the severity and duration of the drought conditions are too great, the effects on development, growth, and yield of most crop plants are profound. Continuous exposure to drought conditions causes major alterations in the plant metabolism that ultimately lead to cell death and consequently yield losses.

Developing stress-tolerant plants is a strategy that has the potential to solve or mediate at least some of these problems. However, traditional plant breeding strategies to develop new lines of plants that exhibit resistance (tolerance) to these types of stresses are relatively slow and require specific resistant lines for crossing with the desired line. Limited germplasm resources for stress tolerance and incompatibility in crosses between distantly related plant species represent significant problems encountered in conventional breeding. Additionally, the cellular processes leading to drought, cold, and salt tolerance in model drought- and/or salt-tolerant plants are complex in nature and involve multiple mechanisms of cellular adaptation and numerous metabolic pathways. This multi-component nature of stress tolerance has not only made breeding for tolerance largely unsuccessful, but has also limited the ability to genetically engineer stress tolerant plants using biotechnological methods.

Therefore, what is needed is the identification of the genes and proteins involved in these multi-component processes leading to increased growth and/or increased stress tolerance. Elucidating the function of genes expressed in stress tolerant plants will not only advance our understanding of plant adaptation and tolerance to environmental stresses, but also may provide important information for designing new strategies for crop improvement.

There are at least four different signal-transduction pathways leading to stress tolerance in the model plant *Arabidopsis thaliana*. These pathways are under the control of distinct transcription factors, protein kinases, protein phosphatases and other signal-transduction pathway components (Shinozaki et al., 2000, Curr. Op. Pl. Biol. 3:217-23). These proteins are prime targets for engineering stress tolerance since they could function as master switches; alterations in a single gene would lead to activation of an entire signal-transduction chain leading to stress tolerance.

Sensing of osmotic stress in bacteria as well as in plants is performed by a two-component system comprising a sensing protein and an effecting protein (Wurgler-Murphy S M and Saito S., 1997, Trends in Biochem. Sci. 22:172-6; Shinozaki et al., 2000, Curr. Op. Pl. Biol. 3: 217-23). Mitogen-activated protein kinase-dependent signal transduction pathways are tightly involved in these processes. Another major component of these signal-transduction chains are GTP-binding proteins (G-proteins). Generally speaking, there are at least three classes of G-proteins: a) heterotrimeric (alpha, beta and gamma subunits), b) monomeric (small) proteins, and c) Dyanins. GTP-binding proteins are named as such because each must bind GTP in order to be active. The functions of GTP-binding proteins are varied as they range from directly transmitting an external signal (where the GTP binding protein is associated with a membrane-bound receptor), to participating in vesicle traffic, to importing proteins into sub-cellular compartments.

Monomeric/small G-proteins are involved in many different cellular processes and have been implicated in vesicle traffic/transport systems, cell cycle regulation, and protein import into organelles. To date, more than 200 small G-proteins have been discovered. These proteins may be classified into five superfamilies based on the structural and functional similarities: Ras, Rho/Rac/Cda42, Rab, Sar1/Arf, and Ran. Generally, members of only the Sar1 and Rab families of small G proteins, are involved in vesicle trafficking in yeast (*S. cerevisiae*) and mammalian cells (Takai et al., 2001, Phys. Rev. 81:153-208). In plants, Rab G proteins have been proven to function in a manner similar to their yeast and mammalian counterparts. Rab G proteins regulate endocytic trafficking pathways and biosynthetic trafficking pathways. Members of the Sar1/Arf family of G proteins also can help recruit coat proteins to transport vesicles (Vemoud et al., 2003, Plant. Physiol. 131:1191-1208).

The SNARE proteins are members of the Rab family of G proteins. The SNARE (Soluble N-ethylmaleimide-sensitive factor attachment protein receptor, or SNAP receptor) proteins are cytoplasmically oriented membrane proteins that play a central role in vesicle trafficking and are conserved among yeast and mammals. Protein transit between organelles is mediated by transport vesicles that bear integral membrane proteins (v-SNAREs), which selectively interact with similar proteins on the target membrane (t-SNAREs), resulting in a docked vesicle.

During adaptation to stress, the plant has to recycle its own components, for example, by transporting proteins from one membrane compartment to another, depositing unused proteins in vacuoles, and processing newly synthesized proteins from the ER to the Golgi. Vesicle trafficking has been shown to be actively involved in this biological recycling process under unfavorable environmental conditions. For example, Snsyr1, one of the ABA-related SNARE proteins, plays a role in the stomata movement and root growth (Geelen, D. et al. 2002, Plant Cell 14: 387-406).

Several groups have identified small G-proteins, homologous to the Rab family of small G-proteins, as being induced upon desiccation treatments in plants (Bolte et al., 2000, Plant Mol. Biol. 42:923-36; O'Mahony and Oliver, 1999, Plant Mol. Biol. 39:809-21). These researchers speculate that the small G-proteins could be involved in preservation of membrane integrity or re-structuring upon relief of stress. However, they have not produced transgenic plants with increased stress tolerance by overexpression of these small G-proteins. In addition, *Arabidopsis* AtRab7, another member of the Rab family of small G proteins, has been shown to be induced after infection of the plant by necrogenic pathogens, and overexpression of AtRab7 has been shown to enhance resistance of transgenic plant to salt and osmotic stress (Mazel et al., 2004 Plant Physiol. 134:118-128).

Although some genes that are involved in stress responses and water use efficiency in plants have been characterized, the characterization and cloning of plant genes that confer stress tolerance and water use efficiency remains largely incomplete and fragmented. For example, certain studies have indicated that drought and salt stress in some plants may be due to additive gene effects, in contrast to other research that indicates specific genes are transcriptionally activated in vegetative tissue of plants under osmotic stress conditions. Although it is generally assumed that stress-induced proteins have a role in tolerance, direct evidence is still lacking, and the functions of many stress-responsive genes are unknown.

There is a fundamental physiochemically-constrained trade-off, in all terrestrial photosynthetic organisms, between $CO_2$ absorption and water loss (Taiz and Zeiger 1991 Plant Physiology, Benjamin/Cummings Publishing Co, p 94). $CO_2$ needs to be in aqueous solution for the action of $CO_2$ fixation enzymes such as Rubisco (Ribulose 1,5-bisphosphate Carboxylase/Oxygenase) and PEPC (Phosphoenolpyruvate carboxylase). As a wet cell surface is required for $CO_2$ diffusion, evaporation will inevitably occur when the humidity is below 100% (Taiz and Zeiger 1991 Plant Physiology, Benjamin/Cummings Publishing Co p 257). Plants have numerous physiological mechanisms to reduce water loss (e.g. waxy cuticles, stomatal closure, leaf hairs, sunken stomatal pits). As these barriers do not discriminate between water and $CO_2$ flux, these water conservation measures will also act to increase resistance to $CO_2$ uptake (Kramer 1983 Water Relations of Plants, Academic Press p 305). Photosynthetic $CO_2$ uptake is absolutely required for plant growth and biomass accumulation in photoautotrophic plants. Water Use Efficiency (WUE) is a parameter frequently used to estimate the trade off between water consumption and $CO_2$ uptake/growth (Kramer 1983 Water Relations of Plants, Academic Press p 405). WUE has been defined and measured in multiple ways. One approach is to calculate the ratio of whole plant dry weight, to the weight of water consumed by the plant throughout its life (Chu et al., 1992, Oncologia, 89:580). Another variation is to use a shorter time interval when biomass accumulation and water use are measured (Mian et al., 1998, Crop Sci. 38:390). Often measurements from restricted parts of the plant are used, for example, measuring only aerial growth and water use (Nienhuis et al., 1994, Amer. J. Bot. 81:943). WUE has also been defined as the ratio of $CO_2$ uptake to water vapor loss from a leaf or portion of a leaf, often measured over a very short time period (seconds/minutes) (Kramer 1983, Water Relations of Plants, Academic Press p. 406). The ratio of $^{13}C/^{12}C$ fixed in plant tissue, and measured with an isotope ratio mass-spectrometer, has also been used to estimate WUE in plants using $C_3$ photosynthesis (Martin et al., 1999, Crop Sci. 1775).

An increase in WUE is informative about the relatively improved efficiency of growth and water consumption, but on it's own it doesn't describe which of these two processes (or both) have changed. In selecting traits for improving crops, an increase in WUE due to a decrease in water use, without a change in growth would have particular merit in an irrigated agricultural system where the water input costs were high. An increase in WUE driven mainly by an increase in growth without a corresponding jump in water use would have applicability to all agricultural systems. In many agricultural systems where water supply is not limiting, an increase in growth, even if it came at the expense of an increased water use (i.e. no change in WUE), could also increase yield. Therefore new methods to increase both WUE and biomass accumulation are required to improve agricultural productivity. As WUE integrates many physiological processes relating to primary metabolism and water use, it is typically a highly polygenic trait with a large genotype by environment interaction (Richards et al., 2002, Crop Sci. 42:111). For these and other reasons few attempts to select for WUE changes in traditional breeding programs have been successful.

There is a need, therefore, to identify genes expressed in stress tolerant plants and plants that are efficient in water use that have the capacity to confer stress tolerance and water use efficiency to its host plant and to other plant species. Newly generated stress tolerant plants will have many advantages, such as an increased range in which the crop plants can be cultivated, by for example, decreasing the water requirements of a plant species. Other desirable advantages include increased resistance to lodging, the bending of shoots or stems in response to wind, rain, pests, or disease.

SUMMARY OF THE INVENTION

This invention fulfills in part the need to identify new, unique polypeptides capable of conferring increased growth and/or increased stress tolerance to plants upon overexpression. The present invention describes a novel genus of Vesicle Trafficking Protein Stress-Related Polypeptides (VTSRPs) and VTSRP coding nucleic acids that are important for modulating a plant's response to an environmental stress. More particularly, overexpression of these VTSRP coding nucleic acids in a plant results in the plant's increased growth and/or increased tolerance to an environmental stress.

Therefore, the present invention includes an isolated plant cell comprising a VTSRP coding nucleic acid, wherein expression of the nucleic acid sequence in the plant cell results in the plant's increased growth and/or increased tolerance to environmental stress as compared to a wild type variety of the plant cell. Preferably, the VTSRP is from *Physcomitrella patens* or *Saccharomyces cerevisiae*. Namely, described herein are the *Physcomitrella patens* Vesicle Trafficking Protein-1 (PPVTP-1 or EST 513), *Physcomitrella patens* GTP Binding Protein-1 (PpGBP-1 or EST 203), and *Saccharomyces cerevisiae* Vesicle Trafficking Protein-1 (ScVTP-1 or ORF 3240).

The invention provides in some embodiments that the VTSRP and coding nucleic acid are those that are found in members of the genus *Physcomitrella* or *Saccharomyces*. In another preferred embodiment, the nucleic acid and polypeptide are from a *Physcomitrella patens* plant or a *Saccharomyces cerevisiae* yeast. In one embodiment, the invention provides that plants overexpressing the VTSRP demonstrate an increase in growth. In a preferred embodiment, the increase in plant growth is due to the plant's increase in Water Use Efficiency (WUE), as compared to a wild-type variety of the plant. In another embodiment, the invention provides that plants overexpressing the LPKSRP demonstrate increased tolerance to an environmental stress, as compared to a wild-type variety of the plant. The invention provides that the environmental stress can be salinity, drought, temperature, metal, chemical, pathogenic and oxidative stresses, or combinations thereof. In a preferred embodiment, the environmental stress is drought stress.

The invention further provides a seed produced by a transgenic plant transformed by a VTSRP coding nucleic acid, wherein the plant is true breeding for increased growth and/or increased tolerance to environmental stress as compared to a wild type variety of the plant.

The invention further provides an agricultural product produced by any of the below-described transgenic plants, plant parts, or seeds. The invention further provides an isolated VTSRP as described below. The invention further provides an isolated VTSRP coding nucleic acid, wherein the VTSRP coding nucleic acid codes for a VTSRP as described below.

The invention further provides an isolated recombinant expression vector comprising a VTSRP coding nucleic acid as described below, wherein expression of the vector in a host cell results in increased tolerance to environmental stress as compared to a wild type variety of the host cell. The invention further provides a host cell containing the vector and a plant containing the host cell.

The invention further provides a method of producing a transgenic plant with a VTSRP coding nucleic acid, wherein expression of the nucleic acid in the plant results in increased growth and/or increased tolerance to environmental stress as compared to a wild type variety of the plant comprising: (a) transforming a plant cell with an expression vector comprising a VTSRP coding nucleic acid, and (b) generating from the plant cell a transgenic plant with increased growth and/or increased tolerance to environmental stress as compared to a wild type variety of the plant. In preferred embodiments, the VTSRP and VTSRP coding nucleic acid are as described below.

The present invention further provides a method of identifying a novel VTSRP, comprising (a) raising a specific antibody response to a VTSRP, or fragment thereof, as described below; (b) screening putative VTSRP material with the antibody, wherein specific binding of the antibody to the material indicates the presence of a potentially novel VTSRP; and (c) identifying from the bound material a novel VTSRP in comparison to known VTSRP. Alternatively, hybridization with nucleic acid probes as described below can be used to identify novel VTSRP nucleic acids.

The present invention also provides methods of modifying the growth and/or stress tolerance of a plant comprising, modifying the expression of a VTSRP nucleic acid in the plant, wherein the VTSRP is as described below. The invention provides that this method can be performed such that the growth and/or stress tolerance is either increased or decreased. Preferably, growth and/or stress tolerance is increased in a plant via increasing expression of a VTSRP nucleic acid.

BRIEF DESCRIPTION OF THE DRAWINGS

Figure 1:
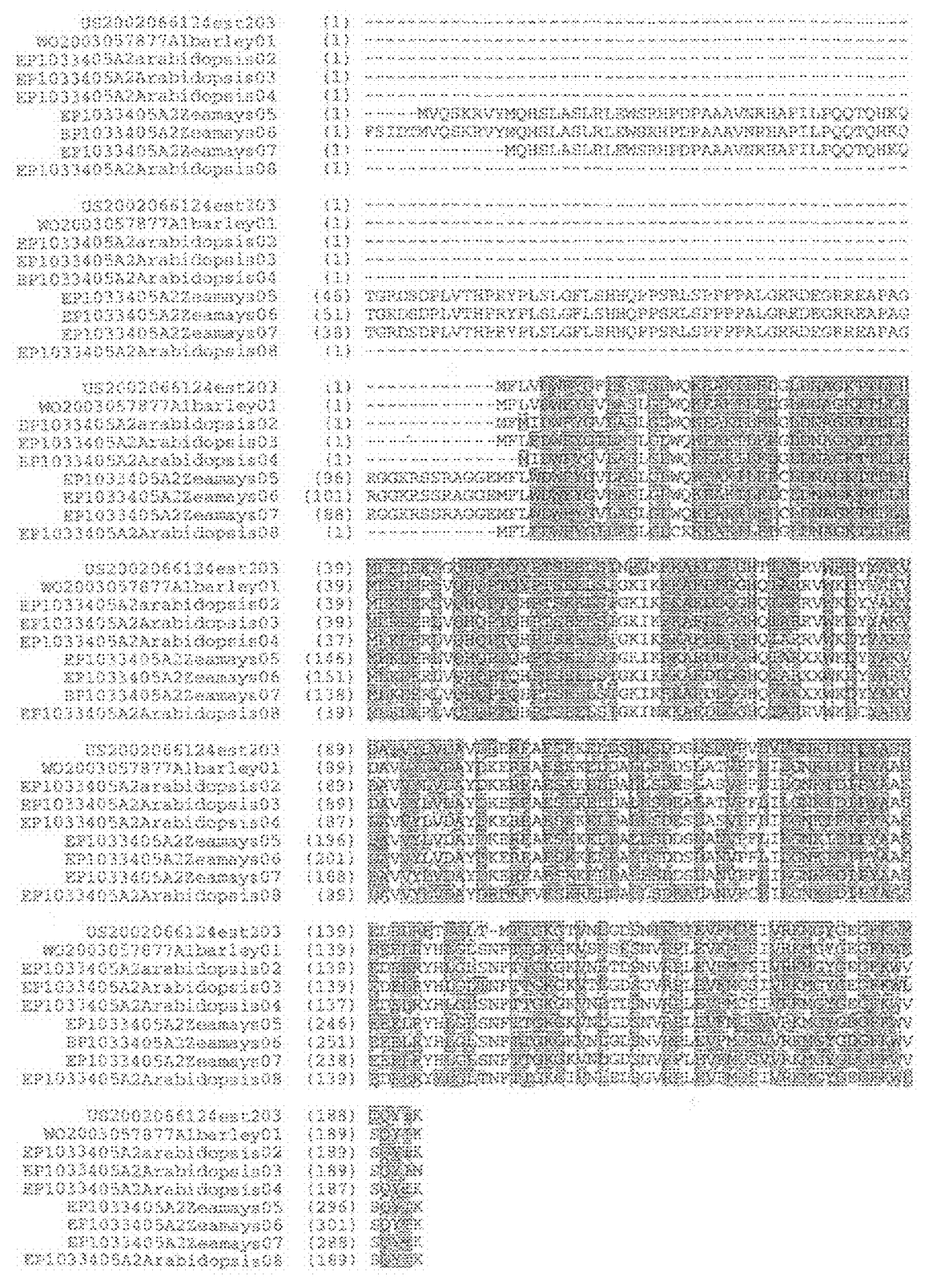

FIG. 1 shows an alignment of the amino acid sequence of the disclosed *Physcomitrella patens* PpGBP-1 (SEQ ID NO:4) with the amino acid sequences of eight polypeptides disclosed in published patent applications (SEQ ID NOs: 24-31, respectively in order of appearance). Amino acid residues that are conserved among each of the sequences are indicated by the dark shading, and amino acid residues that are either identical or similar over some or all of the sequences are indicated with light shading.

Figure 2:
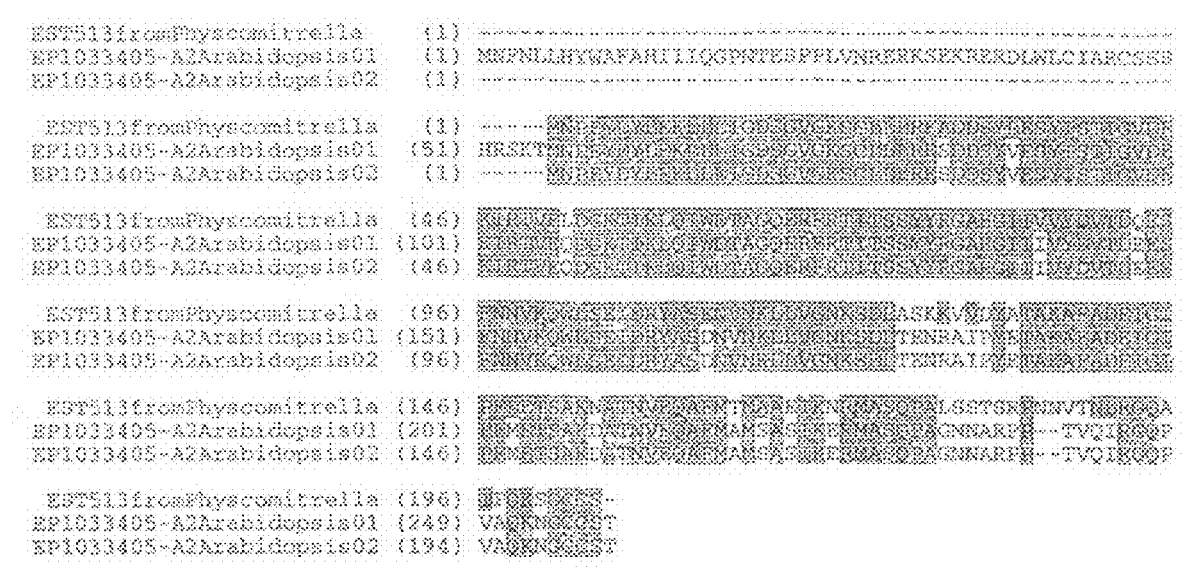

FIG. 2 shows an alignment of the amino acid sequence of the disclosed *Physcomitrella patens* PpVTP-1 (SEQ ID NO:2) with two amino acid sequences disclosed in published patent applications (SEQ ID NOs: 32-33, respectively in order of appearance). Amino acid residues that are either conserved among each of the sequences are indicated by shading, and amino acid residues that are either identical or similar over some or all of the sequences are also indicated with shading.

FIG. 3 shows the polynucleotide and polypeptide sequences of PpVTP, PpGBP-1 and ScVTP-1.

DETAILED DESCRIPTION OF THE INVENTION

The present invention may be understood more readily by reference to the following detailed description of the preferred embodiments of the invention and the Examples included herein. However, before the present compounds, compositions, and methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting. In particular, the designation of the amino acid sequences as polypeptide "Vesicle Trafficking Stress-Related Polypeptides" (VTSRPs), in no way limits the functionality of those sequences.

The present invention describes a novel genus of VTSRPs and VTSRP coding nucleic acids that are important for modulating a plant's response to an environmental stress. More particularly, overexpression of these VTSRP coding nucleic acids in a plant results in the plant's increased growth and/or increased tolerance to an environmental stress. Representative members of the VTSRP genus include, but are not limited to PpGBP-1 (Sar1, EST 203), PpVTP-1 (Rab Small GTPase, EST 513), and ScVTP-1 (YMR197C, V-SNARE protein). In a preferred embodiment, all members of the genus are biologically active vesicle trafficking proteins.

Accordingly, the present invention encompasses VTSRP polynucleotide and polypeptide sequences and their use for increasing a plant's growth and/or tolerance to an environmental stress. In one embodiment, the VTSRP sequences are from a plant, preferably a *Physcomitrella* plant or a *Saccharomyces* yeast, and more preferably a *Physcomitrella patens* plant or a *Saccharomyces cerevisiae* yeast. In another embodiment, the VTSRP sequences include PpGBP-1 (SEQ ID NOS:3 and 4), PpVTP-1 (SEQ ID NOS: 1 and 2), and ScVTP-1 (SEQ ID NOS:5 and 6). The disclosed *Physcomitrella patens* VTSRP sequences and the disclosed *Saccharomyces cerevisiae* VTSRP sequence have significant percent identity to known vesicle trafficking as is indicated below.

The present invention provides a transgenic plant cell transformed by a VTSRP coding nucleic acid, wherein expression of the nucleic acid sequence in the plant cell results in increased growth and/or increased tolerance to an environmental stress as compared to a wild type variety of the plant cell. The invention further provides transgenic plant parts and transgenic plants containing the plant cells described herein. The term "plant" used herein can, depending on context, be understood to refer to whole plant, plant cells, and plant parts including seeds. Plant parts include, but are not limited to, stems, roots, ovules, stamens, leaves, embryos, meristematic regions, callus tissue, gametophytes, sporophytes, pollen, nucrospores, and the like. In one embodiment, the transgenic plant is male sterile. Also provided is a plant seed produced by a transgenic plant transformed by a VTSRP coding nucleic acid, wherein the seed contains the VTSRP coding nucleic acid, and wherein the plant is true breeding for increased growth and/or increased tolerance to environmental stress as compared to a wild type variety of the plant. The invention further provides a seed produced by a transgenic plant expressing a VTSRP, wherein the seed contains the VTSRP, and wherein the plant is true breeding for increased growth and/or increased tolerance to environmental stress as compared to a wild type variety of the plant. The invention also provides an agricultural product produced by any of the below-described transgenic plants, plant parts, and plant seeds. Agricultural products include, but are not limited to, plant extracts, proteins, amino acids, carbohydrates, fats, oils, polymers, vitamins, and the like.

As used herein, the term "variety" refers to a group of plants within a 'species that share constant characters that separate them from the typical form and from other possible varieties within that species. While possessing at least one distinctive trait, a variety is also characterized by some variation between individuals within the variety, based primarily on the Mendelian segregation of traits among the progeny of succeeding generations. A variety is considered "true breeding" for a particular trait if it is genetically homozygous for that trait to the extent that, when the true-breeding variety is self-pollinated, a significant amount of independent segregation of the trait among the progeny is not observed. In the present invention, the trait arises from the transgenic expression of one or more DNA sequences introduced into a plant variety.

The present invention describes for the first time that the *Physcomitrella patens* VTSRPs including Sar1 Small GTPase (PpGBP-1, EST 203), Rab Small GTPase (PpVTP-1, EST 513), and *Saccharomyces cerevisiae* V-SNARE protein (ScVTP-1, YMR197C) are useful for increasing a plant's tolerance to environmental stress. As used herein, the term polypeptide refers to a chain of at least four amino acids joined by peptide bonds. The chain may be linear, branched, circular, or combinations thereof. Accordingly, the present invention provides isolated VTSRPs selected from PpGBP-1, PpVTP-1, and ScVTP-1, and homologs thereof. In preferred embodiments, the VTSRP is selected from: 1) a PpGBP-1 polypeptide as defined in SEQ ID NOs:4 and 2) a PpVTP-1 polypeptide as defined in SEQ ID NOs:2 and 3) an ScVTP-1 polypeptide as defined in SEQ ID NO:6; and homologs and orthologs thereof. Homologs and orthologs of the amino acid sequences are defined below.

The VTSRPs of the present invention are preferably produced by recombinant DNA techniques. For example, a nucleic acid molecule encoding the polypeptide is cloned into an expression vector (as described below), the expression vector is introduced into, a host cell (as described below) and the VTSRP is expressed in the host cell. The VTSRP can then be isolated from the cells by an appropriate purification scheme using standard polypeptide purification techniques. For the purposes of the invention, the term "recombinant polynucleotide" refers to a polynucleotide that has been altered, rearranged, or modified by genetic engineering. Examples include any cloned polynucleotide, and polynucleotides that are linked or joined to heterologous sequences. The term "recombinant" does not refer to alterations to polynucleotides that result from naturally occurring events, such as spontaneous mutations. Alternative to recombinant expression, a VTSRP, or peptide thereof, can be synthesized chemically using standard peptide synthesis techniques. Moreover, native VTSRP can be isolated from cells (e.g., *Physcomitrella patens* or *Saccharomyces cerevisiae* cells), for example using an anti-VTSRP antibody, which can be produced by standard techniques utilizing a VTSRP or fragment thereof.

As used herein, the term "environmental stress" refers to sub-optimal conditions associated with salinity, drought, temperature, metal, chemical, pathogenic and oxidative stresses, or combinations thereof. In preferred embodiments, the environmental stress can be selected from one or more of the group consisting of salinity, drought, or temperature, or combinations thereof, and in particular, can be selected from one or more of the group consisting of high salinity, low water content (drought), or low temperature. In a more preferred embodiment, the environmental stress is drought stress. As also used herein, the term "water use efficiency" refers to the amount of organic matter produced by a plant divided by the amount of water used by the plant in producing it, i.e. the dry weight of a plant in relation to the plant's water use. As used herein, the term "dry weight" refers to everything in the plant other than water, and includes, for example, carbohydrates, proteins, oils, and mineral nutrients. It is also to be understood that as used in the specification and in the claims, "a" or "an" can mean one or more, depending upon the context in which it is used. Thus, for example, reference to "a cell" can mean that at least one cell can be utilized.

As also used herein, the term "nucleic acid" and "polynucleotide" refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. Less common bases, such as inosine, 5-methylcytosine, 6-methyladenine, hypoxanthine, and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR, and in vitro or in vivo transcription.

An "isolated" nucleic acid molecule is one that is substantially separated from other nucleic acid molecules, which are present in the natural source of the nucleic acid (i.e., sequences encoding other polypeptides). Preferably, an "isolated" nucleic acid is free of some of the sequences, which naturally flank the nucleic acid (i.e. sequences located at the 5' and 3' ends of the nucleic acid) in its naturally occurring replicon. For example, a cloned nucleic acid is considered isolated. In various embodiments, the isolated VTSRP nucleic acid molecule can contain less than about 5 kb, 4 kb, 3 kb, 2 kb, 1 kb, 0.5 kb, or 0.1 kb of nucleotide sequences which naturally flank the nucleic acid molecule in genomic DNA of the cell from which the nucleic acid is derived (e.g., a *Physcomitrella patens* cell or a *Saccharomyces cerevisiae* cell). A nucleic acid is also considered isolated if it has been altered by human intervention, or placed in a locus or location that is not its natural site, or if it is introduced into a cell by agroinfection. Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized.

Specifically excluded from the definition of "isolated nucleic acids" are: naturally occurring chromosomes (such as chromosome spreads), artificial chromosome libraries, genomic libraries, and cDNA libraries that exist either as an in vitro nucleic acid preparation or as a transfected/transformed host cell preparation, wherein the host cells are either an in vitro heterogeneous preparation or plated as a heterogeneous population of single colonies. Also specifically excluded are the above libraries wherein a specified nucleic acid makes up less than 5% of the number of nucleic acid inserts in the vector molecules. Further specifically excluded are whole cell genomic DNA or whole cell RNA preparations (including whole cell preparations that are mechanically sheared or enzymatically digested). Even further specifically excluded are the whole cell preparations found as either an in vitro preparation or as a heterogeneous mixture separated by electrophoresis wherein the nucleic acid of the invention has not further been separated from the heterologous nucleic acids in the electrophoresis medium (e.g., further separating by excising a single band from a heterogeneous band population in an agarose gel or nylon blot).

A nucleic acid molecule of the present invention, e.g., a nucleic acid molecule having a nucleotide sequence of SEQ ID NO:1, SEQ ID NO:3, or SEQ ID NO:5, or a portion thereof, can be isolated using standard molecular biology techniques and the sequence information provided herein. For example, a *P. patens* VTSRP cDNA can be isolated from a *P. patens* library using all or a portion of one of the sequences disclosed herein. Moreover, a nucleic acid molecule encompassing all or a portion of one of the sequences of SEQ ID NO:1, SEQ ID NO:3, or SEQ ID NO:5, can be isolated by the polymerase chain reaction using oligonucleotide primers designed based upon this sequence. For example, mRNA can be isolated from plant cells (e.g., by the guanidinium-thiocyanate extraction procedure of Chirgwin et al., 1979, Biochemistry 18:5294-5299), and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon one of the nucleotide sequences shown in SEQ ID NO:1, SEQ ID NO:3, or SEQ ID NO:5. A nucleic acid molecule of the invention can be amplified using cDNA or, alternatively, genomic DNA, as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to a VTSRP nucleotide sequence can be prepared by standard synthetic techniques, e.g., using an automated DNA synthesizer.

In a preferred embodiment, an isolated nucleic acid molecule of the invention comprises one of the nucleotide sequences shown in SEQ ID NO:1, SEQ ID NO:3, or SEQ ID NO:5. These cDNAs may comprise sequences encoding the VTSRPs, (i.e., the "coding region"), as well as 5' untranslated sequences and 3' untranslated sequences. Alternatively, the nucleic acid molecules of the present invention can comprise only the coding region of any of the sequences in SEQ ID NO:1, SEQ ID NO:3, or SEQ ID NO:5, or can contain whole genomic fragments isolated from genomic DNA. The present invention also includes VTSRP coding nucleic acids that encode VTSRPs as described herein. Preferred is a VTSRP coding nucleic acid that encodes a VTSRP selected from the group consisting of Sar1 small GTPase (PpGBP-1, EST 203, SEQ ID NO:4), Rab small GTPase (PpVTP-1, EST 513, SEQ ID NO:2), and v-SNARE protein (YMR197C, SEQ ID NO:6).

Moreover, the nucleic acid molecule of the invention can comprise a portion of the coding region of one of the sequences in SEQ ID NO:1, SEQ ID NO:3, or SEQ ID NO:5, for example, a fragment that can be used as a probe or primer or a fragment encoding a biologically active portion of a VTSRP. The nucleotide sequences determined from the cloning of the VTSRP genes from *Physcomitrella patens* and *Saccharomyces cerevisiae* allow for the generation of probes and primers designed for use in identifying and/or cloning VTSRP homologs in other cell types and organisms, as well as VTSRP homologs from other mosses and related species. The portion of the coding region can also encode a biologically active fragment of a VTSRP.

As used herein, the term "biologically active portion of" a VTSRP is intended to include a portion, e.g., a domain/motif, of a VTSRP that participates in modulation of growth and/or stress tolerance in a plant, and more preferably, drought tolerance. For the purposes of the present invention, modulation of growth and/or stress tolerance refers to at least a 10%, 15%, 20%, 25% or 30%, preferably at least 40%, 45%, 50%, 55% or 60%, more preferably at least 65%, 70%, 75%, 80%, 85%, 90% 95% or more increase or decrease in the growth and/or stress tolerance of a transgenic plant comprising a VTSRP expression cassette (or expression vector) as compared to the growth and/or stress tolerance of a non-transgenic control plant. Methods for quantitating growth and/or stress tolerance are provided at least in Example 7 below. In a preferred embodiment, the biologically active portion of a VTSRP increases a plant's tolerance to drought stress.

Biologically active portions of a VTSRP include peptides comprising amino acid sequences derived from the amino acid sequence of a VTSRP, e.g., an amino acid sequence of SEQ ID NO:2, SEQ ID NO:4, or SEQ ID NO:6, or the amino acid sequence of a polypeptide identical to a VTSRP, which includes fewer amino acids than a full length VTSRP or the full length polypeptide which is identical to a VTSRP, and exhibits at least one activity of a VTSRP. Typically, biologically active portions (e.g., peptides which are, for example, 5, 10, 15, 20, 30, 35, 36, 37, 38, 39, 40, 50, 100, or more amino acids in length) comprise a domain or motif with at least one activity of a VTSRP. Moreover, other biologically active portions in which other regions of the polypeptide are deleted, can be prepared by recombinant techniques and evaluated for one or more of the activities described herein. Preferably, the biologically active portion of a VTSRP includes one or more selected domains/motifs or portions thereof having a vesicle trafficking activity.

The invention also provides VTSRP chimeric or fusion polypeptides. As used herein, a VTSRP "chimeric polypeptide" or "fusion polypeptide" comprises a VTSRP operatively linked to a non-VTSRP. A VTSRP refers to a polypeptide having an amino acid sequence corresponding to a VTSRP, whereas a non-VTSRP refers to a polypeptide having an amino acid sequence corresponding to a polypeptide which is not substantially identical to the VTSRP, e.g., a polypeptide that is different from the VTSRP and is derived from the same or a different organism. With respect to the fusion polypeptide, the term "operatively linked" is intended to indicate that the VTSRP and the non-VTSRP are fused to each other so that both sequences fulfill the proposed function attributed to the sequence used. The non-VTSRP can be fused to the N-terminus or C-terminus of the VTSRP, or alternatively, fragments of the VTSRP such as the N-terminal region (or fragments thereof, the central domain (or fragments thereof, the C-terminal region (or fragments thereof) or combinations of the N-terminal region, the central domain, and the C-terminal region, or fragments of those regions/domains. For example, in one embodiment, the fusion polypeptide is a GST-VTSRP fusion polypeptide in which the VTSRP sequences are fused to the C-terminus of the GST sequences. Such fusion polypeptides can facilitate the purification of recombinant VTSRPs. In another embodiment, the fusion polypeptide is a VTSRP containing a heterologous signal sequence at its N-terminus. In certain host cells (e.g., mammalian host cells), expression and/or secretion of a VTSRP can be increased through use of a heterologous signal sequence.

Preferably, a VTSRP chimeric or fusion polypeptide of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and re-amplified to generate a chimeric gene sequence (See, for example, Current Protocols in Molecular Biology, Eds. Ausubel et al. John Wiley & Sons, 1992). Moreover, many expression vectors are commercially available that already encode a fusion moiety (e.g., a GST polypeptide). A VTSRP encoding nucleic acid can be cloned into such an expression vector such that the fusion moiety is linked in-frame to the VTSRP.

In addition to fragments and fusion polypeptides of the VTSRPs described herein, the present invention includes homologs and analogs of naturally occurring VTSRPs and VTSRP encoding nucleic acids in a plant. “Homologs” are defined herein as two nucleic acids or polypeptides that have similar, or “identical,” nucleotide or amino acid sequences, respectively. Homologs include allelic variants, orthologs, paralogs, agonists, and antagonists of VTSRPs as defined hereafter. The term “homolog” further encompasses nucleic acid molecules that differ from one of the nucleotide sequences shown in SEQ ID NO:1, SEQ ID NO:3, or SEQ ID NO:5 (and portions thereof) due to degeneracy of the genetic code and thus encode the same VTSRP as that encoded by the nucleotide sequences shown in SEQ ID NO:1, SEQ ID NO:3, or SEQ ID NO:5. As used herein, a “naturally occurring” VTSRP refers to a VTSRP amino acid sequence that occurs in nature. Preferably, a naturally occurring VTSRP comprises an amino acid sequence selected from the group consisting of SEQ ID NO:2, SEQ ID NO:4, and SEQ ID NO:6.

An agonist of the VTSRP can retain substantially the same, or a subset, of the biological activities of the VTSRP. An antagonist of the VTSRP can inhibit one or more of the activities of the naturally occurring form of the VTSRP.

Nucleic acid molecules corresponding to natural allelic variants and analogs, orthologs, and paralogs of a VTSRP cDNA can be isolated based on their identity to the *Physcomitrella paten* or *Saccharomyces cerevisiae* VTSRP nucleic acids described herein using VTSRP cDNAs, or a portion thereof, as a hybridization probe according to standard hybridization techniques under stringent hybridization conditions. In an alternative embodiment, homologs of the VTSRP can be identified by screening combinatorial libraries of mutants, e.g., truncation mutants, of the VTSRP for VTSRP agonist or antagonist activity. In one embodiment, a variegated library of VTSRP variants is generated by combinatorial mutagenesis at the nucleic acid level and is encoded by a variegated gene library. A variegated library of VTSRP variants can be produced by, for example, enzymatically ligating a mixture of synthetic oligonucleotides into gene sequences such that a degenerate set of potential VTSRP sequences is expressible as individual polypeptides, or alternatively, as a set of larger fusion polypeptides (e.g., for phage display) containing the set of VTSRP sequences therein. There are a variety of methods that can be used to produce libraries of potential VTSRP homologs from a degenerate oligonucleotide sequence. Chemical synthesis of a degenerate gene sequence can be performed in an automatic DNA synthesizer, and the synthetic gene is then ligated into an appropriate expression vector. Use of a degenerate set of genes allows for the provision, in one mixture, of all of the sequences encoding the desired set of potential VTSRP sequences. Methods for synthesizing degenerate oligonucleotides are known in the art (See, e.g., Narang, S. A., 1983, Tetrahedron 39:3; Itakura et al., 1984, Annu. Rev. Biochem 53:323; Itakura et al., 1984, Science 198:1056; Ike et al., 1983, Nucleic Acid Res. 11:477).

In addition, libraries of fragments of the VTSRP coding regions can be used to generate a variegated population of VTSRP fragments for screening and subsequent selection of homologs of a VTSRP. In one embodiment, a library of coding sequence fragments can be generated by treating a double stranded PCR fragment of a VTSRP coding sequence with a nuclease under conditions wherein nicking occurs only about once per molecule, denaturing the double stranded DNA, renaturing the DNA to form double stranded DNA, which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal, and internal fragments of various sizes of the VTSRP.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of VTSRP homologs. The most widely used techniques, which are amenable to high throughput analysis, for screening large gene libraries typically include cloning the gene library into replaceable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique that enhances the frequency of functional mutants in the libraries, can be used in combination with the screening assays to identify VTSRP homologs (Arvin and Yourvan, 1992, PNAS 89:7811-7815; Delgrave et al., 1993, Polypeptide Engineering 6(3):327-331). In another embodiment, cell based assays can be exploited to analyze a variegated VTSRP library, using methods well known in the art. The present invention further provides a method of identifying a novel VTSRP, comprising (a) raising a specific antibody response to a VTSRP, or a fragment thereof, as described herein; (b) screening putative VTSRP material with the antibody, wherein specific binding of the antibody to the material indicates the presence of a potentially novel VTSRP; and (c) analyzing the bound material in comparison to known VTSRP, to determine its novelty.

As stated above, the present invention includes VTSRPs and homologs thereof. To determine the percent sequence identity of two amino acid sequences (e.g., one of the sequences of SEQ ID NO:2, SEQ ID NO:4, and SEQ ID NO:6, and a mutant form thereof), the sequences are aligned for optimal comparison purposes (e.g., gaps can be introduced in the sequence of one polypeptide for optimal alignment with the other polypeptide or nucleic acid). The amino acid residues at corresponding amino acid positions are then compared. When a position in one sequence (e.g., one of the sequences of SEQ ID NO:2, SEQ ID NO:4, and SEQ ID NO:6) is occupied by the same amino acid residue as the corresponding position in the other sequence (e.g., a mutant form of the sequence of SEQ ID NO:2, SEQ ID NO:4, and SEQ ID NO:6), then the molecules are identical at that position. The same type of comparison can be made between two nucleic acid sequences.

The percent sequence identity between the two sequences is a function of the number of identical positions shared by the sequences (i.e., percent sequence identity=numbers of identical positions/total numbers of positions×100). Preferably, the isolated amino acid homologs included in the present invention are at least about 50-60%, preferably at least about 60-70%, and more preferably at least about 70-75%, 75-80%, 80-85%, 85-90%, or 90-95%, and most preferably at least about 96%, 97%, 98%, 99%, or more identical to an entire amino acid sequence shown in SEQ ID NO:2, SEQ ID NO:4, or SEQ ID NO:6. In yet another embodiment, the isolated amino acid homologs included in the present invention are at least about 50-60%, preferably at least about 60-70%, and more preferably at least about 70-75%, 75-80%, 80-85%, 85-90%, or 90-95%, and most preferably at least about 96%, 97%, 98%, 99%, or more identical to an entire amino acid sequence encoded by a nucleic acid sequence shown in SEQ ID NO:1, SEQ ID NO:3, or SEQ ID NO:5. In a preferred embodiment, the polypeptide comprises two regions wherein the first region commences with an aspartic acid residue at position 1 and has a tryptophan residue at position 2, a phenylalanine residue at position 3, a tyrosine residue at position 4, a glycine residue at position 5, a leucine residue at position 7, an alanine residue at position 8, a serine residue at position 9, a glycine residue at position 11, a leucine residue at position 12, a lysine residue at position 15, a glutamic acid residue at position 16, an alanine residue at position 17, a lysine residue at position 18, a isoleucine residue at position 19, a leucine residue at position 20, a phenylalanine residue at position 21, a leucine residue at position 22, a leucine residue at position 24, an aspartic acid residue at position 25, an asparagine residue at position 26, an alanine residue at position 27, a glycine residue at position 28, a lysine residue at position 29, a threonine residue at position 30, a threonine residue at position 31, a leucine residue at position 32, a leucine residue at position 33, a histidine residue at position 34, a methionine residue at position 35, a leucine residue at position 36, a lysine residue at position 37, an aspartic acid residue at position 38, a glutamic acid residue at position 39, a leucine residue at position 41, a glutamine residue at position 43, a histidine residue at position 44, a glutamine residue at position 45, a proline residue at position 46, a threonine residue at position 47, a glutamine residue at position 48, a proline residue at position 50, a threonine residue at position 51, a serine residue at position 52, a glutamic acid residue at position 53, a glutamic acid residue at position 54, a leucine residue at position 55, a serine residue at position 56, a isoleucine residue at position 57, a phenylalanine residue at position 62, a lysine residue at position 63, an alanine residue at position 64, a phenylalanine residue at position 65, an aspartic acid residue at position 66, a leucine residue at position 67, a glycine residue at position 68, a glycine residue at position 69, a histidine residue at position 70, a isoleucine residue at position 72, an alanine residue at position 73, an arginine residue at position 74, a tryptophan residue at position 77, an aspartic acid residue at position 79, a tyrosine residue at position 81, an alanine residue at position 82, a lysine residue at position 83, a valine residue at position 84, an aspartic acid residue at position 85, an alanine residue at position 86, a valine residue at position 88, a tyrosine residue at position 89, a leucine residue at position 90, a valine residue at position 91, an aspartic acid residue at position 92, an alanine residue at position 93, an aspartic acid residue at position 95, an arginine residue at position 98, a phenylalanine residue at position 99, a glutamic acid residue at position 101, a serine residue at position 102, a lysine residue at position 103, a glutamic acid residue at position 105, a leucine residue at position 106, an aspartic acid residue at position 107, a leucine residue at position 109, a leucine residue at position 110, a serine residue at position 111, an aspartic acid residue at position 112, a leucine residue at position 115, a valine residue at position 118, a proline residue at position 119, a leucine residue at position 121, a leucine residue at position 123, a glycine residue at position 124, an asparagine residue at position 125, a lysine residue at position 126, a isoleucine residue at position 127, an aspartic acid residue at position 128, a isoleucine residue at position 129, a proline residue at position 130, a tyrosine residue at position 131, an alanine residue at position 132, a serine residue at position 134, a glutamic acid residue at position 136, a glutamic acid residue at position 137, a leucine residue at position 138, an arginine residue at position 139, a leucine residue at position 142, a glycine residue at position 143, and a leucine residue at position 144; and the second region is downstream from the first region, commences with a threonine residue at position 1, and has a threonine residue at position 2, a glycine residue at position 3, a lysine residue at position 4, a glycine residue at position 5, a valine residue at position 7, a leucine residue at position 9, a serine residue at position 12, an arginine residue at position 15, a proline residue at position 16, a glutamic acid residue at position 18, a valine residue at position 19, a phenylalanine residue at position 20, a methionine residue at position 21, a cysteine residue at position 22, a serine residue at position 23, a valine residue at position 25, an arginine residue at position 26, a lysine residue at position 27, a methionine residue at position 28, a glycine residue at position 29, a tyrosine residue at position 30, a glycine residue at position 31, a glycine residue at position 33, a phenylalanine residue at position 34, a lysine residue at position 35, a tryptophan residue at position 36, a glutamine residue at position 39, a tyrosine residue at position 40, and an isoleucine residue at position 41.

In another preferred embodiment, an isolated nucleic acid homolog of the invention comprises a nucleotide sequence which is at least about 40-60%, preferably at least about 60-70%, more preferably at least about 70-75%, 75-80%, 80-85%, 85-90%, or 90-95%, and even more preferably at least about 95%, 96%, 97%, 98%, 99%, or more identical to a nucleotide sequence shown in SEQ ID NO:1, SEQ ID NO:3, or SEQ ID NO:5, or to a portion comprising at least 60 consecutive nucleotides thereof. The preferable length of sequence comparison for nucleic acids is at least 75 nucleotides, more preferably at least 100 nucleotides, and most preferably the entire length of the coding region. It is even more preferable that the nucleic acid homologs encode proteins having homology with SEQ ID NO:2, SEQ ID NO:4, or SEQ ID NO:6.

It is further preferred that the isolated nucleic acid homolog of the invention encodes a VTSRP, or portion thereof, that is at least 80% identical to an amino acid sequence of SEQ ID NO:2, SEQ ID NO:4, or SEQ ID NO:6, and that functions as a modulator of growth and/or an environmental stress response in a plant. In a more preferred embodiment, overexpression of the nucleic acid homolog in a plant increases the plant's growth and/or the tolerance of the plant to an environmental stress. In a further preferred embodiment, the nucleic acid homolog encodes a VTSRP that functions as a vesicle trafficking protein.

For the purposes of the invention, the percent sequence identity between two nucleic acid or polypeptide sequences is determined using the Vector NTI 6.0 (PC) software package (InforMax, 7600 Wisconsin Ave., Bethesda, Md. 20814). A gap opening penalty of 15 and a gap extension penalty of 6.66 are used for determining the percent identity of two nucleic acids. A gap-opening penalty of 10 and a gap extension penalty of 0.1 are used for determining the percent identity of two polypeptides. All other parameters are set at the default settings. For purposes of a multiple alignment (Clustal W algorithm), the gap-opening penalty is 10, and the gap extension penalty is 0.05 with blosum62 matrix. It is to be understood that for the purposes of determining sequence identity when comparing a DNA sequence to an RNA sequence, a thymidine nucleotide is equivalent to a uracil nucleotide.

In another aspect, the invention provides an isolated nucleic acid comprising a polynucleotide that hybridizes to the polynucleotide of SEQ ID NO:1, SEQ ID NO:3, or SEQ ID NO:5 under stringent conditions. More particularly, an isolated nucleic acid molecule of the invention is at least 15 nucleotides in length and hybridizes under stringent conditions to the nucleic acid molecule comprising a nucleotide sequence of SEQ ID NO:1, SEQ ID NO:3, or SEQ ID NO:5. In other embodiments, the nucleic acid is at least 30, 50, 100, 250, or more nucleotides in length. Preferably, an isolated nucleic acid homolog of the invention comprises a nucleotide sequence which hybridizes under highly stringent conditions to the nucleotide sequence shown in SEQ ID NO:1, SEQ ID NO:3, or SEQ ID NO:5 and functions as a modulator of growth and/or stress tolerance in a plant. In a further preferred embodiment, overexpression of the isolated nucleic acid homolog in a plant increases a plant's growth and/or tolerance to an environmental stress. In an even further preferred embodiment, the isolated nucleic acid homolog encodes a VTSRP that functions as a vesicle trafficking protein.

As used herein with regard to hybridization for DNA to a DNA blot, the term "stringent conditions" may refer to hybridization overnight at 60° C. in 10× Denhart's solution, 6×SSC, 0.5% SDS, and 100 µg/ml denatured salmon sperm DNA. Blots are washed sequentially at 62° C. for 30 minutes each time in 3×SSC/0.1% SDS, followed by 1×SSC/0.1% SDS, and finally 0.1×SSC/0.1% SDS. In a preferred embodiment, the phrase "stringent conditions" refers to hybridization in a 6×SSC solution at 65° C. As also used herein, "highly stringent conditions" refers to hybridization overnight at 65° C. in 10× Denharts solution, 6×SSC, 0.5% SDS, and 100 µg/ml denatured salmon sperm DNA. Blots are washed sequentially at 65° C. for 30 minutes each time in 3×SSC/0.1% SDS, followed by 1×SSC/0.1% SDS, and finally 0.1× SSC/0.1% SDS. Methods for nucleic acid hybridizations are described in Meinkoth and Wahl, 1984, Anal. Biochem. 138: 267-284; Current Protocols in Molecular Biology, Chapter 2, Ausubel et al. Eds., Greene Publishing and Wiley-Interscience, New York, 1995; and Tijssen, 1993, Laboratory Techniques in Biochemistry and Molecular Biology: Hybridization with Nucleic Acid Probes, Part I, Chapter 2, Elsevier, New York, 1993. Preferably, an isolated nucleic acid molecule of the invention that hybridizes under stringent or highly stringent conditions to a sequence of SEQ ID NO:1, SEQ ID NO:3, or SEQ ID NO:5 corresponds to a naturally occurring nucleic acid molecule. As used herein, a "naturally occurring" nucleic acid molecule refers to an RNA or DNA molecule having a nucleotide sequence that occurs in nature (e.g., encodes a natural polypeptide). In one embodiment, the nucleic acid encodes a naturally occurring *Physcomitrella patens* VTSRP or *Saccharomyces cerevisiae* VTSRP.

Using the above-described methods, and others known to those of skill in the art, one of ordinary skill in the art can isolate homologs of the VTSRPs comprising amino acid sequences shown in SEQ ID NO:2, SEQ ID NO:4, or SEQ ID NO:6. One subset of these homologs is allelic variants. As used herein, the term "allelic variant" refers to a nucleotide sequence containing polymorphisms that lead to changes in the amino acid sequences of a VTSRP and that exist within a natural population (e.g., a plant species or variety). Such natural allelic variations can typically result in 1-5% variance in a VTSRP nucleic acid. Allelic variants can be identified by sequencing the nucleic acid sequence of interest in a number of different plants, which can be readily carried out by using hybridization probes to identify the same VTSRP genetic locus in those plants. Any and all such nucleic acid variations and resulting amino acid polymorphisms or variations in a VTSRP that are the result of natural allelic variation and that do not alter the functional activity of a VTSRP, are intended to be within the scope of the invention.

Moreover, nucleic acid molecules encoding VTSRPs from the same or other species such as VTSRP analogs, orthologs, and paralogs, are intended to be within the scope of the present invention. As used herein, the term "analogs" refers to two nucleic acids that have the same or similar function, but that have evolved separately in unrelated organisms. As used herein, the term "orthologs" refers to two nucleic acids from different species, but that have evolved from a common ancestral gene by speciation. Normally, orthologs encode polypeptides having the same or similar functions. As also used herein, the term "paralogs" refers to two nucleic acids that are related by duplication within a genome. Paralogs usually have different functions, but these functions may be related (Tatusov, R. L. et al., 1997, Science 278(5338):631-637). Analogs, orthologs, and paralogs of a naturally occurring VTSRP can differ from the naturally occurring VTSRP by post-translational modifications, by amino acid sequence differences, or by both. Post-translational modifications include in vivo and in vitro chemical derivatization of polypeptides, e.g., acetylation, carboxylation, phosphorylation, or glycosylation, and such modifications may occur during polypeptide synthesis or processing or following treatment with isolated modifying enzymes. In particular, orthologs of the invention will generally exhibit at least 80-85%, more preferably, 85-90% or 90-95%, and most preferably 95%, 96%, 97%, 98%, or even 99% identity, or 100% sequence identity, with all or part of a naturally occurring VTSRP amino acid sequence, and will exhibit a function similar to a VTSRP. Preferably, a VTSRP ortholog of the present invention functions as a modulator of growth and/or an environmental stress response in a plant and/or functions as a vesicle trafficking protein. More preferably, a VTSRP ortholog increases the growth and/or stress tolerance of a plant. In one embodiment, the VTSRP orthologs function as vesicle trafficking proteins.

In addition to naturally-occurring variants of a VTSRP sequence that may exist in the population, the skilled artisan will further appreciate that changes can be introduced by mutation into a nucleotide sequence of SEQ ID NO:2, SEQ ID NO:4, or SEQ ID NO:6, thereby leading to changes in the amino acid sequence of the encoded VTSRP, without altering the functional activity of the VTSRP. For example, nucleotide substitutions leading to amino acid substitutions at "nonessential" amino acid residues can be made in a sequence of SEQ ID NO:1, SEQ ID NO:3, or SEQ ID NO:5. A "nonessential" amino acid residue is a residue that can be altered from the wild-type sequence of one of the VTSRPs without altering the activity of said VTSRP, whereas an "essential" amino acid residue is required for VTSRP activity. Other amino acid residues, however, (e.g., those that are not conserved or only semi-conserved in the domain having VTSRP activity) may not be essential for activity and thus are likely to be amenable to alteration without altering VTSRP activity.

Accordingly, another aspect of the invention pertains to nucleic acid molecules encoding VTSRPs that contain changes in amino acid residues that are not essential for VTSRP activity. Such VTSRPs differ in amino acid sequence from a sequence contained in SEQ ID NO:2, SEQ ID NO:4, or SEQ ID NO:6, yet retain at least one of the VTSRP activities described herein. In one embodiment, the isolated nucleic acid molecule comprises a nucleotide sequence encoding a polypeptide, wherein the polypeptide comprises an amino acid sequence at least about 50-60% identical to one of the sequences of SEQ ID NO:2, SEQ ID NO:4, or SEQ ID NO:6, more preferably at least about 60-70% identical to one of the sequences of SEQ ID NO:2, SEQ ID NO:4, or SEQ ID NO:6, even more preferably at least about 70-75%, 75-80%, 80-85%, 85-90%, or 90-95% identical to one of the sequences of SEQ ID NO:2, SEQ ID NO:4, or SEQ ID NO:6, and most preferably at least about 96%, 97%, 98%, or 99% identical to one of the sequences of SEQ ID NO:2, SEQ ID NO:4, or SEQ ID NO:6. The preferred VTSRP homologs of the present invention preferably participate in a plant's growth and/or a stress tolerance response in a plant, or more particularly, function as vesicle trafficking proteins.

An isolated nucleic acid molecule encoding a VTSRP having sequence identity with a polypeptide sequence of SEQ ID NO:2, SEQ ID NO:4, or SEQ ID NO:6 can be created by introducing one or more nucleotide substitutions, additions, or deletions into a nucleotide sequence of SEQ ID NO:1, SEQ ID NO:3, or SEQ ID NO:5, respectively, such that one or more amino acid substitutions, additions, or deletions are introduced into the encoded polypeptide. Mutations can be introduced into one of the sequences of SEQ ID NO:1, SEQ ID NO:3, or SEQ ID NO:5 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain.

Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine). Thus, a predicted nonessential amino acid residue in a VTSRP is preferably replaced with another amino acid residue from the same side chain family. Alternatively, in another embodiment, mutations can be introduced randomly along all or part of a VTSRP coding sequence, such as by saturation mutagenesis, and the resultant mutants can be screened for a VTSRP activity described herein to identify mutants that retain VTSRP activity. Following mutagenesis of one of the sequences of SEQ ID NO:1, SEQ ID NO:3, or SEQ ID NO:5, the encoded polypeptide can be expressed recombinantly and the activity of the polypeptide can be determined by analyzing the growth and/or stress tolerance of a plant expressing the polypeptide as described in Example 7.

Additionally, optimized VTSRP nucleic acids can be created. Preferably, an optimized VTSRP nucleic acid encodes a VTSRP that modulates a plant's growth and/or tolerance to an environmental stress, and more preferably increases a plant's growth and/or tolerance to an environmental stress upon its overexpression in the plant. As used herein, "optimized" refers to a nucleic acid that is genetically engineered to increase its expression in a given plant or animal. To provide plant optimized VTSRP nucleic acids, the DNA sequence of the gene can be modified to 1) comprise codons preferred by highly expressed plant genes; 2) comprise an A+T content in nucleotide base composition to that substantially found in plants; 3) form a plant initiation sequence; or 4) to eliminate sequences that cause destabilization, inappropriate polyadenylation, degradation and termination of RNA, or that form secondary structure hairpins or RNA splice sites. Increased expression of VTSRP nucleic acids in plants can be achieved by utilizing the distribution frequency of codon usage in plants in general or in a particular plant. Methods for optimizing nucleic acid expression in plants can be found in EPA 0359472; EPA 0385962; PCT Application No. WO 91/16432; U.S. Pat. No. 5,380,831; U.S. Pat. No. 5,436,391; Perlack et al., 1991., Proc. Natl. Acad. Sci. USA 88:3324-3328; and Murray et al., 1989, Nucleic Acids Res. 17:477498.

As used herein, "frequency of preferred codon usage" refers to the preference exhibited by a specific host cell in usage of nucleotide codons to specify a given amino acid. To determine the frequency of usage of a particular codon in a gene, the number of occurrences of that codon in the gene is divided by the total number of occurrences of all codons specifying the same amino acid in the gene. Similarly, the frequency of preferred codon usage exhibited by a host cell can be calculated by averaging frequency of preferred codon usage in a large number of genes expressed by the host cell. It is preferable that this analysis be limited to genes that are highly expressed by the host cell. The percent deviation of the frequency of preferred codon usage for a synthetic gene from that employed by a host cell is calculated first by determining the percent deviation of the frequency of usage of a single codon from that of the host cell followed by obtaining the average deviation over all codons. As defined herein, this calculation includes unique codons (i.e., ATG and TGG). In general terms, the overall average deviation of the codon usage of an optimized gene from that of a host cell is calculated using the equation $1A = n = 1ZX_n - Y_nX_n$ times $100Z$ where $X_n$=frequency of usage for codon n in the host cell; $Y_n$=frequency of usage for codon n in the synthetic gene; n represents an individual codon that specifies an amino acid; and the total number of codons is Z. The overall deviation of the frequency of codon usage, A, for all amino acids should preferably be less than about 25%, and more preferably less than about 10%.

Hence, a VTSRP nucleic acid can be optimized such that its distribution frequency of codon usage deviates, preferably, no more than 25% from that of highly expressed plant genes and, more preferably, no more than about 10%. In addition, consideration is given to the percentage G+C content of the degenerate third base (monocotyledons appear to favor G+C in this position, whereas dicotyledons do not). It is also recognized that the XCG (where X is A, T, C, or G) nucleotide is the least preferred codon in dicots whereas the XTA codon is avoided in both monocots and dicots. Optimized VTSRP nucleic acids of this invention also preferably have CG and TA doublet avoidance indices closely approximating those of the chosen host plant (e.g., *Physcomitrella patens, Brassica napus, Glycine max,* or *Oryza sativa*). More preferably these indices deviate from that of the host by no more than about 10-15%.

In addition to the nucleic acid molecules encoding the VTSRPs described above, another aspect of the invention pertains to isolated nucleic acid molecules that are antisense thereto. Antisense polynucleotides are thought to inhibit gene expression of a target polynucleotide by specifically binding the target polynucleotide and interfering with transcription, splicing, transport, translation, and/or stability of the target polynucleotide. Methods are described in the prior art for targeting the antisense polynucleotide to the chromosomal DNA, to a primary RNA transcript, or to a processed mRNA. Preferably, the target regions include splice sites, translation initiation codons, translation termination codons, and other sequences within the open reading frame.

The term "antisense," for the purposes of the invention, refers to a nucleic acid comprising a polynucleotide that is sufficiently complementary to all or a portion of a gene, primary transcript, or processed mRNA, so as to interfere with expression of the endogenous gene. "Complementary" polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. It is understood that two polynucleotides may hybridize to each other even if they are not completely complementary to each other, provided that each has at least one region that is substantially complementary to the other. The term "antisense nucleic acid" includes single stranded RNA as well as double-stranded DNA expression cassettes that can be transcribed to produce an antisense RNA. "Active" antisense nucleic acids are antisense RNA molecules that are capable of selectively hybridizing with a primary transcript or mRNA encoding a polypeptide having at least 80% sequence identity with the polypeptide of SEQ ID NO:2, SEQ ID NO:4, or SEQ ID NO:6.

The antisense nucleic acid can be complementary to an entire VTSRP coding strand, or to only a portion thereof. In one embodiment, an antisense nucleic acid molecule is antisense to a "coding region" of the coding strand of a nucleotide sequence encoding a VTSRP. The term "coding region" refers to the region of the nucleotide sequence comprising codons that are translated into amino acid residues. In another embodiment, the antisense nucleic acid molecule is antisense to a "noncoding region" of the coding strand of a nucleotide sequence encoding a VTSRP. The term "noncoding region" refers to 5' and 3' sequences that flank the coding region that are not translated into amino acids (i.e., also referred to as 5' and 3' untranslated regions). The antisense nucleic acid molecule can be complementary to the entire coding region of VTSRP mRNA, but more preferably is an oligonucleotide that is antisense to only a portion of the coding or noncoding region of VTSRP mRNA. For example, the antisense oligonucleotide can be complementary to the region surrounding the translation start site of VTSRP mRNA. An antisense oligonucleotide can be, for example, about 5, 10, 15, 20, 25, 30, 35, 40, 45, or 50 nucleotides in length. Typically, the antisense molecules of the present invention comprise an RNA having 60-100% sequence identity with at least 14 consecutive nucleotides of SEQ ID NO:1, SEQ ID NO:3, or SEQ ID NO:5, or a polynucleotide encoding a polypeptide of SEQ ID NO:2, SEQ ID NO:4, or SEQ ID NO:6. Preferably, the sequence identity will be at least 70%, more preferably at least 75%, 80%, 85%, 90%, 95%, or 98%, and most preferably 99%.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual P-units, the strands run parallel to each other (Gaultier et al., 1987, Nucleic Acids. Res. 15:6625-6641). The antisense nucleic acid molecule can also comprise a 2'-o-methylribonucleotide (Inoue et al., 1987, Nucleic Acids Res. 15:6131-6148) or a chimeric RNA-DNA analogue (Inoue et al., 1987, FEBS Lett. 215:327-330).

The antisense nucleic acid molecules of the invention are typically administered to a cell or generated in situ such that they hybridize with or bind to cellular mRNA and/or genomic DNA encoding a VTSRP to thereby inhibit expression of the polypeptide, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. The antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong prokaryotic, viral, or eukaryotic (including plant) promoter are preferred.

As an alternative to antisense polynucleotides, ribozymes, sense polynucleotides, or double stranded RNA (dsRNA) can be used to reduce expression of a VTSRP polypeptide. As used herein, the term "ribozyme" refers to a catalytic RNA-based enzyme with ribonuclease activity that is capable of cleaving a single-stranded nucleic acid, such as an mRNA, to which it has a complementary region. Ribozymes (e.g., hammerhead ribozymes described in Haselhoff and Gerlach, 1988, Nature 334:585-591) can be used to catalytically cleave VTSRP mRNA transcripts to thereby inhibit translation of VTSRP mRNA. A ribozyme having specificity for a VTSRP-encoding nucleic acid can be designed based upon the nucleotide sequence of a VTSRP cDNA, as disclosed herein (i.e., SEQ ID NO:1, SEQ ID NO:3, or SEQ ID NO:5) or on the basis of a heterologous sequence to be isolated according to methods taught in this invention. For example, a derivative of a Tetrahymena L-19 IVS RNA can be constructed in which the nucleotide sequence of the active site is complementary to the nucleotide sequence to be cleaved in a VTSRP-encoding mRNA. See, e.g., U.S. Pat. Nos. 4,987,071 and 5,116,742 to Cech et al. Alternatively, VTSRP mRNA can be used to select a catalytic RNA having a specific ribonuclease activity from a pool of RNA molecules. See, e.g., Bartel, D. and Szostak, J. W., 1993, Science 261: 1,411-1418. In preferred embodiments, the ribozyme will contain a portion having at least 7, 8, 9, 10, 12, 14, 16, 18, or 20 nucleotides, and more preferably 7 or 8 nucleotides, that have 100% complementarity to a portion of the target RNA. Methods for making ribozymes are known to those skilled in the art. See, e.g., U.S. Pat. Nos. 6,025,167; 5,773,260; and 5,496,698.

The term "dsRNA," as used herein, refers to RNA hybrids comprising two strands of RNA. The dsRNAs can be linear or circular in structure. In a preferred embodiment, dsRNA is specific for a polynucleotide encoding either the polypeptide of SEQ ID NO:2, SEQ ID NO:4, or SEQ ID NO:6, or a polypeptide having at least 80% sequence identity with a polypeptide of SEQ ID NO:2, SEQ ID NO:4, or SEQ ID NO:6. The hybridizing RNAs may be substantially or completely complementary. By "substantially complementary," is meant that when the two hybridizing RNAs are optimally aligned using the BLAST program as described above, the hybridizing portions are at least 95% complementary. Preferably, the dsRNA will be at least 100 base pairs in length. Typically, the hybridizing RNAs will be of identical length with no over hanging 5' or 3' ends and no gaps. However, dsRNAs having 5' or 3' overhangs of up to 100 nucleotides may be used in the methods of the invention.

The dsRNA may comprise ribonucleotides, ribonucleotide analogs such as 2'-O-methyl ribosyl residues, or combinations thereof. See, e.g., U.S. Pat. Nos. 4,130,641 and 4,024,222. A dsRNA polyriboinosinic acid:polyribocytidylic acid is described in U.S. Pat. No. 4,283,393. Methods for making and using dsRNA are known in the art. One method comprises the simultaneous transcription of two complementary DNA strands, either in vivo, or in a single in vitro reaction mixture. See, e.g., U.S. Pat. No. 5,795,715. In one embodiment, dsRNA can be introduced into a plant or plant cell directly by standard transformation procedures. Alternatively, dsRNA can be expressed in a plant cell by transcribing two complementary RNAs.

Other methods for the inhibition of endogenous gene expression, such as triple helix formation (Moser et al., 1987, Science 238:645-650 and Cooney et al., 1988, Science 241:456-459) and co-suppression (Napoli et al., 1990, The Plant Cell 2:279-289) are known in the art. Partial and full-length cDNAs have been used for the cosuppression of endogenous plant genes. See, e.g., U.S. Pat. Nos. 4,801,340, 5,034,323, 5,231,020, and 5,283,184; Van der Kroll et al., 1990, The Plant Cell 2:291-299; Smith et al., 1990, M61. Gen. Genetics 224:477-481; and Napoli et al., 1990, The Plant Cell 2:279-289.

For sense suppression, it is believed that introduction of a sense polynucleotide blocks transcription of the corresponding target gene. The sense polynucleotide will have at least 65% sequence identity with the target plant gene or RNA. Preferably, the percent identity is at least 80%, 90%, 95%, or more. The introduced sense polynucleotide need not be full length relative to the target gene or transcript. Preferably, the sense polynucleotide will have at least 65% sequence identity with at least 100 consecutive nucleotides of SEQ ID NO:1, SEQ ID NO:3, or SEQ ID NO:5. The regions of identity can comprise introns and/or exons and untranslated regions. The introduced sense polynucleotide may be present in the plant cell transiently, or may be stably integrated into a plant chromosome or extrachromosomal replicon.

Alternatively, VTSRP gene expression can be inhibited by targeting nucleotide sequences complementary to the regulatory region of a VTSRP nucleotide sequence (e.g., a VTSRP promoter and/or enhancer) to form triple helical structures that prevent transcription of a VTSRP gene in target cells. See generally, Helene, C., 1991, Anticancer Drug Des. 6(6):569-84; Helene, C. et al., 1992, Ann. N.Y. Acad. Sci. 660:27-36; and Maher, L. J., 1992, Bioassays 14(12):807-15.

In addition to the VTSRP nucleic acids and polypeptides described above, the present invention encompasses these nucleic acids and polypeptides attached to a moiety. These moieties include, but are not limited to, detection moieties, hybridization moieties, purification moieties, delivery moieties, reaction moieties, binding moieties, and the like. A typical group of nucleic acids having moieties attached are probes and primers. Probes and primers typically comprise a substantially isolated oligonucleotide. The oligonucleotide typically comprises a region of nucleotide sequence that hybridizes under stringent conditions to at least about 12, preferably about 25, more preferably about 40, 50, or 75 consecutive nucleotides of a sense strand of one of the sequences set forth in SEQ ID NO:1, SEQ ID NO:3, or SEQ ID NO:5; an anti-sense sequence of one of the sequences set forth in SEQ ID NO:1, SEQ ID NO:3, or SEQ ID NO:5; or naturally occurring mutants thereof. Primers based on a nucleotide sequence of SEQ ID NO:1, SEQ ID NO:3, or SEQ ID NO:5 can be used in PCR reactions to clone VTSRP homologs. Probes based on the VTSRP nucleotide sequences can be used to detect transcripts or genomic sequences encoding the same or substantially identical polypeptides. In preferred embodiments, the probe further comprises a label group attached thereto, e.g. the label group can be a radioisotope, a fluorescent compound, an enzyme, or an enzyme co-factor. Such probes can be used as a part of a genomic marker test kit for identifying cells which express a VTSRP, such as by measuring a level of a VTSRP-encoding nucleic acid, in a sample of cells, e.g., detecting VTSRP mRNA levels or determining whether a genomic VTSRP gene has been mutated or deleted.

In particular, a useful method to ascertain the level of transcription of the gene (an indicator of the amount of mRNA available for translation to the gene product) is to perform a Northern blot (For reference, see, for example, Ausubel et al., 1988, Current Protocols in Molecular Biology, Wiley: New York). The information from a Northern blot at least partially demonstrates the degree of transcription of the transformed gene. Total cellular RNA can be prepared from cells, tissues, or organs by several methods, all well-known in the art, such as that described in Bormann, E. R. et al., 1992, Mol. Microbiol. 6:317-326. To assess the presence or relative quantity of polypeptide translated from this mRNA, standard techniques, such as a Western blot, may be employed. These techniques are well known to one of ordinary skill in the art. (See, for example, Ausubel et al., 1988, Current Protocols in Molecular Biology, Wiley: New York).

The invention further provides an isolated recombinant expression vector comprising a VTSRP nucleic acid as described above, wherein expression of the vector in a host cell results in increased tolerance to environmental stress as compared to a wild type variety of the host cell. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses, and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. As used herein with respect to a recombinant expression vector, "operatively linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers, and other expression control elements (e.g., polyadenylation signals). Such regulatory sequences are described, for example, in Goeddel, Gene Expression Technology: Methods in Enzymology 185, Academic Press, San Diego, Calif. (1990) and Gruber and Crosby, in: Methods in Plant Molecular Biology and Biotechnology, eds. Glick and Thompson, Chapter 7, 89-108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of polypeptide desired, etc. The expression vectors of the invention can be introduced into host cells to thereby produce polypeptides or peptides, including fusion polypeptides or peptides, encoded by nucleic acids as described herein (e.g., VTSRPs, mutant forms of VTSRPs, fusion polypeptides, etc.).

The recombinant expression vectors of the invention can be designed for expression of VTSRPs in prokaryotic or eukaryotic cells. For example, VTSRP genes can be expressed in bacterial cells such as *C. glutamicum*, insect cells (using baculovirus expression vectors), yeast and other fungal cells (See Romanos, M. A. et al., 1992, Foreign gene expression in yeast: a review, Yeast 8:423488; van den Hondel, C. A. M. J. J. et al., 1991, Heterologous gene expression in filamentous fungi, in: More Gene Manipulations in Fungi, J. W. Bennet & L. L. Lasure, eds., p. 396-428: Academic Press: San Diego; and van den Hondel, C. A. M. J. J. & Punt, P. J., 1991, Gene transfer systems and vector development for filamentous fungi, in: Applied Molecular Genetics of Fungi, Peberdy, J. F. et al., eds., p. 1-28, Cambridge University Press: Cambridge), algae (Falciatore et al., 1999, Marine Biotechnology 1(3): 239-251), ciliates of the types: *Holotrichia, Peritrichia, Spirotrichia, Suctoria, Tetrahymena, Paramecium, Colpidium, Glaucoma, Platyophrya, Potomacus, Pseudocohnilembus, Euplotes, Engelmaniella*, and *Stylonychia*, especially of the genus *Stylonychia lemnae* with vectors following a transformation method as described in PCT Application No. WO 98/01572, and multicellular plant cells (See Schmidt, R. and Willmitzer, L., 1988, High efficiency *Agrobacterium tumefaciens*-mediated transformation of *Arabidopsis thaliana* leaf and cotyledon explants, Plant Cell Rep. 583-586; Plant Molecular Biology and Biotechnology, C Press, Boca Raton, Fla., chapter 6/7, S.71-119 (1993); F. F. White, B. Jenes et al., Techniques for Gene Transfer, in: Transgenic Plants, Vol. 1, Engineering and Utilization, eds. Kungund R. Wu, 12843, Academic Press: 1993; Potrykus, 1991, Annu. Rev. Plant Physiol. Plant Molec. Biol. 42:205-225 and references cited therein), or mammalian cells. Suitable host cells are discussed further in Goeddel, Gene Expression Technology: Methods in Enzymology 185, Academic Press: San Diego, Calif. (1990). Alternatively, the recombinant expression vector can be transcribed and translated in vitro, for example using T7 promoter regulatory sequences and T7 polymerase.

Expression of polypeptides in prokaryotes is most often carried out with vectors containing constitutive or inducible promoters directing the expression of either fusion or non-fusion polypeptides. Fusion vectors add a number of amino acids to a polypeptide encoded therein, usually to the amino terminus of the recombinant polypeptide but also to the C-terminus or fused within suitable regions in the polypeptides. Such fusion vectors typically serve three purposes: 1) to increase expression of a recombinant polypeptide; 2) to increase the solubility of a recombinant polypeptide; and 3) to aid in the purification of a recombinant polypeptide by acting as a ligand in affinity purification. Often, in fusion expression vectors, a proteolytic cleavage site is introduced at the junction of the fusion moiety and the recombinant polypeptide to enable separation of the recombinant polypeptide from the fusion moiety subsequent to purification of the fusion polypeptide. Such enzymes, and their cognate recognition sequences, include Factor Xa, thrombin, and enterokinase.

Typical fusion expression vectors include pGEX (Pharmacia Biotech Inc.; Smith, D. B. and Johnson, K. S., 1988, Gene 67:3140), pMAL (New England Biolabs, Beverly, Mass.), and pRIT5 (Pharmacia, Piscataway, N.J.) which fuse glutathione S-transferase (GST), maltose E binding polypeptide, or polypeptide A, respectively, to the target recombinant polypeptide. In one embodiment, the coding sequence of the VTSRP is cloned into a pGEX expression vector to create a vector encoding a fusion polypeptide comprising, from the N-terminus to the C-terminus, GST-thrombin cleavage site-X polypeptide. The fusion polypeptide can be purified by affinity chromatography using glutathione-agarose resin. Recombinant VTSRP unfused to GST can be recovered by cleavage of the fusion polypeptide with thrombin.

Examples of suitable inducible non-fusion *E. coli* expression vectors include pTrc (Amann et al., 1988, Gene 69:301-315) and pET 1 id (Studier et al., Gene Expression Technology: Methods in Enzymology 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21(DE3) or HMS174(DE3) from a resident X prophage harboring a T7 gn1 gene under the transcriptional control of the lacUV 5 promoter.

One strategy to maximize recombinant polypeptide expression is to express the polypeptide in a host bacterium with an impaired capacity to proteolytically cleave the recombinant polypeptide (Gottesman, S., Gene Expression Technology: Methods in Enzymology 185, Academic Press, San Diego, Calif. (1990) 119-128). Another strategy is to alter the sequence of the nucleic acid to be inserted into an expression vector so that the individual codons for each amino acid are those preferentially utilized in the bacterium chosen for expression, such as *C. glutamicum* (Wada et al., 1992, Nucleic Acids Res. 20:2111-2118). Such alteration of nucleic acid sequences of the invention can be carried out by standard DNA synthesis techniques.

In another embodiment, the VTSRP expression vector is a yeast expression vector. Examples of vectors for expression in yeast *S. cerevisiae* include pYepSec1 (Baldari, et al., 1987, EMBO J. 6:229-234), pMFa (Kujan and Herskowitz, 1982, Cell 30:933-943), pJRY88 (Schultz et al., 1987, Gene 54:113-123), and pYES2 (Invitrogen Corporation, San Diego, Calif.). Vectors and methods for the construction of vectors appropriate for use in other fungi, such as the filamentous fungi, include those detailed in: van den Hondel, C. A. M. J. J. & Punt, P. J., 1991, "Gene transfer systems and vector development for filamentous fungi," in: Applied Molecular Genetics of Fungi, J. F. Peberdy, et al., eds., p. 1-28, Cambridge University Press: Cambridge.

Alternatively, the VTSRPs of the invention can be expressed in insect cells using baculovirus expression vectors. Baculovirus vectors available for expression of polypeptides in cultured insect cells (e.g., Sf 9 cells) include the pAc series (Smith et al., 1983, Mol. Cell Biol. 3:2156-2165) and the pVL series (Lucklow and Summers, 1989, Virology 170: 31-39).

In yet another embodiment, a VTSRP nucleic acid of the invention is expressed in mammalian cells using a mammalian expression vector. Examples of mammalian expression vectors include pCDM8 (Seed, B., 1987, Nature 329:840) and pMT2PC (Kaufman et al., 1987, EMBO J. 6:187-195). When used in mammalian cells, the expression vector's control functions are often provided by viral regulatory elements. For example, commonly used promoters are derived from polyoma, Adenovirus 2, cytomegalovirus, and Simian Virus 40. For other suitable expression systems for both prokaryotic and eukaryotic cells, see chapters 16 and 17 of Sambrook, J., Fritsh, E. F., and Maniatis, T. Molecular Cloning: A Laboratory Manual. latest ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, Genes Dev. 1:268-277), lymphoid-specific promoters (Calame and Eaton, 1988, Adv. Immunol. 43:235-275), in particular promoters of T cell receptors (Winoto and Baltimore, 1989, EMBO J. 8:729-733), and immunoglobulins (Banerji et al., 1983, Cell 33:729-740; Queen and Baltimore, 1983, Cell 33:741-748), neuron-specific promoters (e.g., the neurofilament promoter; Byrne and Ruddle, 1989, PNAS 86:5473-5477), pancreas-specific promoters (Edlund et al., 1985, Science 230:912-916), and mammary gland-specific promoters (e.g., milk whey promoter; U.S. Pat. No. 4,873,316 and European Application Publication No. 264, 166). Developmentally-regulated promoters are also encompassed, for example, the murine box promoters (Kessel and Gruss, 1990, Science 249:374-379) and the fetopolypeptide promoter (Campes and Tilghman, 1989, Genes Dev. 3:537-546).

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics or herbicides) is generally introduced into the host cells along with the gene of interest. Preferred selectable markers include those that confer resistance to drugs, such as G418, hygromycin, and methotrexate, or in plants that confer resistance towards an herbicide such as glyphosate, glufosinate, or imidazolinone. Nucleic acid molecules encoding a selectable marker can be introduced into a host cell on the same vector as that encoding a VTSRP or can be introduced on a separate vector. Cells stably transfected with the introduced nucleic acid molecule can be identified by, for example, herbicide selection (e.g., cells that have incorporated the selectable marker gene will survive, while the other cells die).

In a preferred embodiment of the present invention, the VTSRPs are expressed in plants and plants cells such as unicellular plant cells (e.g. algae) (See Falciatore et al., 1999, Marine Biotechnology 1(3):239-251 and references therein) and plant cells from higher plants (e.g., the spermatophytes, such as crop plants). A VTSRP may be "introduced" into a plant cell by any means, including transfection, transformation or transduction, electroporation, particle bombardment, agroinfection, and the like. One transformation method known to those of skill in the art is the dipping of a flowering plant into an Agrobacteria solution, wherein the Agrobacteria contain the VTSRP nucleic acid, followed by breeding of the transformed gametes.

Other suitable methods for transforming or transfecting host cells including plant cells can be found in Sambrook, et al. (Molecular Cloning: A Laboratory Manual. latest ed., Cold Spring Harbor Laboratory, Cold Spring Harbor Laboratory Press, Cold Spring Harbor, N.Y., 1989) and other laboratory manuals such as Methods in Molecular Biology, 1995, Vol. 44, *Agrobacterium* protocols, ed: Gartland and Davey, Humana Press, Totowa, N.J. As increased growth and increased biotic and abiotic stress tolerance are general traits wished to be inherited into a wide variety of plants like maize, wheat, rye, oat, triticale, rice, barley, soybean, peanut, cotton, rapeseed and canola, manicot, pepper, sunflower and tagetes, solanaceous plants like potato, tobacco, eggplant, and tomato, *Vicia* species, pea, alfalfa, bushy plants (coffee, cacao, tea), *Salix* species, trees (oil palm, coconut), perennial grasses, and forage crops, these crop plants are also preferred target plants for a genetic engineering as one further embodiment of the present invention. Forage crops include, but are not limited to, Wheatgrass, Canarygrass, Bromegrass, Wildrye Grass, Bluegrass, Orchardgrass, Alfalfa, Salfoin, Birdsfoot Trefoil, Alsike Clover, Red Clover, and Sweet Clover.

In one embodiment of the present invention, transfection of a VTSRP into a plant is achieved by *Agrobacterium* mediated gene transfer. *Agrobacterium* mediated plant transformation can be performed using for example the GV3101(pMP90) (Koncz and Schell, 1986, Mol. Gen. Genet. 204:383-396) or LBA4404 (Clontech) *Agrobacterium tumefaciens* strain. Transformation can be performed by standard transformation and regeneration techniques (Deblaere et al., 1994, Nucl. Acids. Res. 13:4777-4788; Gelvin, Stanton B. and Schilperoort, Robert A, Plant Molecular Biology Manual, $2^{nd}$ Ed.—Dordrecht: Kluwer Academic Publ., 1995.—in Sect., Ringbuc Zentrale Signatur: BTI 1-P ISBN 0-7923-2731-4; Glick, Bernard R.; Thompson, John E., Methods in Plant Molecular Biology and Biotechnology, Boca Raton: CRC Press, 1993 360 S., ISBN 0-8493-5164-2). For example, rapeseed can be transformed via cotyledon or hypocotyl transformation (Moloney et al., 1989, Plant Cell Report 8:238-242; De Block et al., 1989, Plant Physiol. 91:694-701). Use of antibiotics for *Agrobacterium* and plant selection depends on the binary vector and the *Agrobacterium* strain used for transformation. Rapeseed selection is normally performed using kanamycin as the selectable plant marker. *Agrobacterium* mediated gene transfer to flax can be performed using, for example, a technique described by Mlynarova et al., 1994, Plant Cell Report 13:282-285. Additionally, transformation of soybean can be performed using for example a technique described in European Patent No. 0424 047, U.S. Pat. No. 5,322,783, European Patent No. 0397 687, U.S. Pat. No. 5,376,543, or U.S. Pat. No. 5,169,770. Transformation of maize can be achieved by particle bombardment, polyethylene glycol mediated DNA uptake, or via the silicon carbide fiber technique. (See, for example, Freeling and Walbot "The maize handbook" Springer Verlag: New York (1993) ISBN 3-540-97826-7). A specific example of maize transformation is found in U.S. Pat. No. 5,990,387, and a specific example of wheat transformation can be found in PCT Application No. WO 93/07256.

According to the present invention, the introduced VTSRP may be maintained in the plant cell stably if it is incorporated into a non-chromosomal autonomous replicon or integrated into the plant chromosomes. Alternatively, the introduced VTSRP may be present on an extra-chromosomal non-replicating vector and may be transiently expressed or transiently active.

In one embodiment, a homologous recombinant microorganism can be created wherein the VTSRP is integrated into a chromosome, a vector is prepared which contains at least a portion of a VTSRP gene into which a deletion, addition, or substitution has been introduced to thereby alter, e.g., functionally disrupt, the VTSRP gene. Preferably, the VTSRP gene is a *Physcomitrella patens* or *Saccharomyces cerevisiae* VTSRP gene, but it can be a homolog from a related plant or yeast, or even from a mammalian or insect source. In one embodiment, the vector is designed such that, upon homologous recombination, the endogenous VTSRP gene is functionally disrupted (i.e., no longer encodes a functional polypeptide; also referred to as a knock-out vector). Alternatively, the vector can be designed such that, upon homologous recombination, the endogenous VTSRP gene is mutated or otherwise altered but still encodes a functional polypeptide (e.g., the upstream regulatory region can be altered to thereby alter the expression of the endogenous VTSRP). To create a point mutation via homologous recombination, DNA-RNA hybrids can be used in a technique known as chimeraplasty (Cole-Strauss et al., 1999, Nucleic Acids Research 27(5): 1323-1330 and Kmiec, 1999, Gene Therapy American Scientist 87(3):240-247). Homologous recombination procedures in *Physcomitrella patens* are also well known in the art and are contemplated for use herein.

Whereas in the homologous recombination vector, the altered portion of the VTSRP gene is flanked at its 5' and 3' ends by an additional nucleic acid molecule of the VTSRP gene to allow for homologous recombination to occur between the exogenous VTSRP gene carried by the vector and an endogenous VTSRP gene, in a microorganism or plant. The additional flanking VTSRP nucleic acid molecule is of sufficient length for successful homologous recombination with the endogenous gene. Typically, several hundreds of base pairs up to kilobases of flanking DNA (both at the 5' and 3' ends) are included in the vector (See e.g., Thomas, K. R., and Capecchi, M. R., 1987, Cell 51:503 for a description of homologous recombination vectors or Strepp et al., 1998, PNAS, 95(8):43684373 for cDNA based recombination in *Physcomitrella patens*). The vector is introduced into a microorganism or plant cell (e.g., via polyethylene glycol mediated DNA), and cells in which the introduced VTSRP gene has homologously recombined with the endogenous VTSRP gene are selected using art-known techniques.

In another embodiment, recombinant microorganisms can be produced that contain selected systems that allow for regulated expression of the introduced gene. For example, inclusion of a VTSRP gene on a vector placing it under control of the lac operon permits expression of the VTSRP gene only in the presence of IPTG. Such regulatory systems are well known in the art.

Whether present in an extra-chromosomal non-replicating vector or a vector that is integrated into a chromosome, the VTSRP polynucleotide preferably resides in a plant expression cassette. A plant expression cassette preferably contains regulatory sequences capable of driving gene expression in plant cells that are operatively linked so that each sequence can fulfill its function, for example, termination of transcription by polyadenylation signals. Preferred polyadenylation signals are those originating from *Agrobacterium tumefaciens* t-DNA such as the gene 3 known as octopine synthase of the Ti-plasmid pTiACH5 (Gielen et al., 1984, EMBO J. 3:835) or functional equivalents thereof, but also all other terminators functionally active in plants are suitable. As plant gene expression is very often not limited on transcriptional levels, a plant expression cassette preferably contains other operatively linked sequences like translational enhancers such as the overdrive-sequence containing the 5'-untranslated leader sequence from tobacco mosaic virus enhancing the polypeptide per RNA ratio (Gallie et al., 1987, Nucl. Acids Research 15:8693-8711). Examples of plant expression vectors include those detailed in: Becker, D., Kemper, E., Schell, J. and Masterson, R., 1992, New plant binary vectors with selectable markers located proximal to the left border, Plant Mol. Biol. 20: 1195-1197; and Bevan, M. W., 1984, Binary *Agrobacterium* vectors for plant transformation, Nucl. Acid. Res. 12:8711-8721; Vectors for Gene Transfer in Higher Plants; in: Transgenic Plants, Vol. 1, Engineering and Utilization, eds.: Kung and R. Wu, Academic Press, 1993, S. 15-38.

Plant gene expression should be operatively linked to an appropriate promoter conferring gene expression in a timely, cell specific, or tissue specific manner. Promoters useful in the expression cassettes of the invention include any promoter that is capable of initiating transcription in a plant cell. Such promoters include, but are not limited to, those that can be obtained from plants, plant viruses, and bacteria that contain genes that are expressed in plants, such as *Agrobacterium* and *Rhizobium*.

The promoter may be constitutive, inducible, developmental stage-preferred, cell type-preferred, tissue-preferred, or organ-preferred. Constitutive promoters are active under most conditions. Examples of constitutive promoters include the CaMV 19S and 35S promoters (Odell et al., 1985, Nature 313:810-812), the sX CaMV 35S promoter (Kay et al., 1987, Science 236:1299-1302) the Sep1 promoter, the rice actin promoter (McElroy et al., 1990, Plant Cell 2:163-171), the *Arabidopsis* actin promoter, the ubiquitan promoter (Christensen et al., 1989, Plant Molec. Biol. 18:675-689), pEmu (Last et al., 1991, Theor. Appl. Genet. 81:581-588), the figwort mosaic virus 35S promoter, the Smas promoter (Velten et al., 1984, EMBO J 3:2723-2730), the GRP1-8 promoter, the cinnamyl alcohol dehydrogenase promoter (U.S. Pat. No. 5,683,439), promoters from the T-DNA of *Agrobacterium*, such as mannopine synthase, nopaline synthase, and octopine synthase, the small subunit of ribulose biphosphate carboxylase (ssuRUBISCO) promoter, and the like.

Inducible promoters are preferentially active under certain environmental conditions, such as the presence or absence of a nutrient or metabolite, heat or cold, light, pathogen attack, anaerobic conditions, and the like. For example, the hsp80 promoter from *Brassica* is induced by heat shock; the PPDK promoter is induced by light; the PR-1 promoter from tobacco, *Arabidopsis*, and maize are inducible by infection with a pathogen; and the Adh1 promoter is induced by hypoxia and cold stress. Plant gene expression can also be facilitated via an inducible promoter (For review, see Gatz, 1997, Annu. Rev. Plant Physiol. Plant Mol. Biol. 48:89-108). Chemically inducible promoters are especially suitable if gene expression is wanted to occur in a time specific manner. Examples of such promoters are a salicylic acid inducible promoter (PCT Application No. WO 95/19443), a tetracycline inducible promoter (Gatz et al., 1992, Plant J. 2:397-404), and an ethanol inducible promoter (PCT Application No. WO 93/21334).

In one preferred embodiment of the present invention, the inducible promoter is a stress-inducible promoter. For the purposes of the invention, stress inducible promoters are preferentially active under one or more of the following stresses: sub-optimal conditions associated with salinity, drought, temperature, metal, chemical, pathogenic, and oxidative stresses. Stress inducible promoters include, but are not limited to, Cor78 (Chak et al., 2000, Planta 210:875-883; Hovath et al., 1993, Plant Physiol. 103:1047-1053), Cor15a (Artus et al., 1996, PNAS 93(23):13404-09), Rci2A (Medina et al., 2001, Plant Physiol. 125:1655-66; Nylander et al., 2001, Plant Mol. Biol. 45:341-52; Navarre and Goffeau, 2000, EMBO J. 19:2515-24; Capel et al., 1997, Plant Physiol. 115:569-76), Rd22 (Xiong et al., 2001, Plant Cell 13:2063-83; Abe et al., 1997, Plant Cell 9:1859-68; Iwasaki et al., 1995, Mol. Gen. Genet. 247:391-8), cDet6 (Lang and Palve, 1992, Plant Mol. Biol. 20:951-62), ADH1 (Hoeren et al., 1998, Genetics 149:479-90), KAT1 (Nakamura et al., 1995, Plant Physiol. 109:371-4), KST1 (Muller-Rober et al., 1995, EMBO 14:2409-16), Rha1 (Terryn et al., 1993, Plant Cell 5:1761-9; Terryn et al., 1992, FEBS Lett. 299(3):287-90), ARSK1 (Atkinson et al., 1997, GenBank Accession # L22302, and PCT Application No. WO 97/20057), PtxA (Plesch et al., GenBank Accession # X67427), SbHRGP3 (Ahn et al., 1996, Plant Cell 8:1477-90), GH3 (Liu et al., 1994, Plant Cell 6:645-57), the pathogen inducible PRP1-gene promoter (Ward et al., 1993, Plant. Mol. Biol. 22:361-366), the heat inducible hsp80-promoter from tomato (U.S. Pat. No. 5187267), cold inducible alpha-amylase promoter from potato (PCT Application No; WO 96/12814), or the wound-inducible pinII-promoter (European Patent No. 375091). For other examples of drought, cold, and salt-inducible promoters, such as the RD29A promoter, see Yamaguchi-Shinozalei et al., 1993, Mol. Gen. Genet. 236:331-340.

Developmental stage-preferred promoters are preferentially expressed at certain stages of development. Tissue and organ preferred promoters include those that are preferentially expressed in certain tissues or organs, such as leaves, roots, seeds, or xylem. Examples of tissue preferred and organ preferred promoters include, but are not limited to fruit-preferred, ovule-preferred, male tissue-preferred, seed-preferred, integument-preferred, tuber-preferred, stalk-preferred, pericarp-preferred, and leaf-preferred, stigma-preferred, pollen-preferred, anther-preferred, a petal-preferred, sepal-preferred, pedicel-preferred, silique-preferred, stem-preferred, root-preferred promoters, and the like. Seed preferred promoters are preferentially expressed during seed development and/or germination. For example, seed preferred promoters can be embryo-preferred, endosperm preferred, and seed coat-preferred. See Thompson et al., 1989, BioEssays 10:108. Examples of seed preferred promoters include, but are not limited to, cellulose synthase (celA), Cim1, gamma-zein, globulin-1, maize 19 kD zein (cZ19B1), and the like.

Other suitable tissue-preferred or organ-preferred promoters include the napin-gene promoter from rapeseed (U.S. Pat. No. 5,608,152), the USP-promoter from *Vicia faba* (Baeumlein et al., 1991, Mol. Gen. Genet. 225(3):459-67), the oleosin-promoter from *Arabidopsis* (PCT Application No. WO 98/45461), the phaseolin-promoter from *Phaseolus vulgaris* (U.S. Pat. No. 5,504,200), the Bce4-promoter from *Brassica* (PCT Application No. WO 91/13980), or the legumin B4 promoter (LeB4; Baeumlein et al., 1992, Plant Journal, 2(2):233-9), as well as promoters conferring seed specific expression in monocot plants like maize, barley, wheat, rye, rice, etc. Suitable promoters to note are the lpt2 or lpt1-gene promoter from barley (PCT Application No. WO 95/15389 and PCT Application No. WO 95/23230) or those described in PCT Application No. WO 99/16890 (promoters from the barley hordein-gene, rice glutelin gene, rice oryzin gene, rice prolamin gene, wheat gliadin gene, wheat glutelin gene, oat glutelin gene, Sorghum kasirin-gene, and rye secalin gene).

Other promoters useful in the expression cassettes of the invention include, but are not limited to, the major chlorophyll a/b binding protein promoter, histone promoters, the Ap3 promoter, the β-conglycin promoter, the napin promoter, the soybean lectin promoter, the maize 15 kD zein promoter, the 22 kD zein promoter, the 27 kD zein promoter, the g-zein promoter, the waxy, shrunken 1, shrunken 2, and bronze promoters, the Zm13 promoter (U.S. Pat. No. 5,086,169), the maize polygalacturonase promoters (PG) (U.S. Pat. Nos. 5,412,085 and 5,545,546), and the SGB6 promoter (U.S. Pat. No. 5,470,359), as well as synthetic or other natural promoters.

Additional flexibility in controlling heterologous gene expression in plants may be obtained by using DNA binding domains and response elements from heterologous sources (i.e., DNA binding domains from non-plant sources). An example of such a heterologous DNA binding domain is the LexA DNA binding domain (Brent and Ptashne, 1985, Cell 43:729-736).

The invention further provides a recombinant expression vector comprising a VTSRP DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to a VTSRP mRNA. Regulatory sequences operatively linked to a nucleic acid molecule cloned in the antisense orientation can be chosen which direct the continuous expression of the antisense RNA molecule in a variety of cell types. For instance, viral promoters and/or enhancers, or regulatory sequences can be chosen which direct constitutive, tissue specific, or cell type specific expression of antisense RNA. The antisense expression vector can be in the form of a recombinant plasmid, phagemid, or attenuated virus wherein antisense nucleic acids are produced under the control of a high efficiency regulatory region. The activity of the regulatory region can be determined by the cell type into which the vector is introduced. For a discussion of the regulation of gene expression using antisense genes, see Weintraub, H. et al., 1986, Antisense RNA as a molecular tool for genetic analysis, Reviews—Trends in Genetics, Vol. 1(1), and Mol et al., 1990, FEBS Letters 268:427-430.

Another aspect of the invention pertains to host cells into which a recombinant expression vector of the invention has been introduced. The terms "host cell" and "recombinant host cell" are used interchangeably herein. It is understood that such terms refer not only to the particular subject cell but they also apply to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. For example, a VTSRP can be expressed in bacterial cells such as *C. glutamicum*, insect cells, fungal cells, or mammalian cells (such as Chinese hamster ovary cells (CHO) or COS cells), algae, ciliates, plant cells, fungi, or other microorganisms like *C. glutamicum*. Other suitable host cells are known to those skilled in the art.

A host cell of the invention, such as a prokaryotic or eukaryotic host cell in culture, can be used to produce (i.e., express) a VTSRP. Accordingly, the invention further provides methods for producing VTSRPs using the host cells of the invention. In one embodiment, the method comprises culturing the host cell of invention (into which a recombinant expression vector encoding a VTSRP has been introduced, or into which genome has been introduced a gene encoding a wild-type or altered VTSRP) in a suitable medium until the VTSRP is produced. In another embodiment, the method further comprises isolating VTSRPs from the medium or the host cell.

Another aspect of the invention pertains to isolated VTSRPs, and biologically active portions thereof. An "isolated" or "purified" polypeptide or biologically active portion thereof is free of some of the cellular material when produced by recombinant DNA techniques, or chemical precursors or other chemicals when chemically synthesized. The language "substantially free of cellular material" includes preparations of VTSRP in which the polypeptide is separated from some of the cellular components of the cells in which it is naturally or recombinantly produced. In one embodiment, the language "substantially free of cellular material" includes preparations of a VTSRP having less than about 30% (by dry weight) of non-VTSRP material (also referred to herein as a "contaminating polypeptide"), more preferably less than about 20% of non-VTSRP material, still more preferably less than about 10% of non-VTSRP material, and most preferably less than about 5% non-VTSRP material.

When the VTSRP or biologically active portion thereof is recombinantly produced, it is also preferably substantially free of culture medium, i.e., culture medium represents less than about 20%, more preferably less than about 10%, and most preferably less than about 5% of the volume of the polypeptide preparation. The language "substantially free of chemical precursors or other chemicals" includes preparations of VTSRP in which the polypeptide is separated from chemical precursors or other chemicals that are involved in the synthesis of the polypeptide. In one embodiment, the language "substantially free of chemical precursors or other chemicals" includes preparations of a VTSRP having less than about 30% (by dry weight) of chemical precursors or non-VTSRP chemicals, more preferably less than about 20% chemical precursors or non-VTSRP chemicals, still more preferably less than about 10% chemical precursors or non-VTSRP chemicals, and most preferably less than about 5% chemical precursors or non-VTSRP chemicals. In preferred embodiments, isolated polypeptides, or biologically active portions thereof, lack contaminating polypeptides from the same organism from which the VTSRP is derived. Typically, such polypeptides are produced by recombinant expression of, for example, a *Physcomitrella patens* or *Saccharomyces cerevisiae* VTSRP in plants other than *Physcomitrella patens* or *Saccharomyces cerevisiae*, or microorganisms such as *C. glutamicum*, ciliates, algae, or fungi.

The nucleic acid molecules, polypeptides, polypeptide homologs, fusion polypeptides, primers, vectors, and host cells described herein can be used in one or more of the following methods: identification of *Physcomitrella patens* or *Saccharomyces cerevisiae* and related organisms; mapping of genomes of organisms related to *Physcomitrella patens* or *Saccharomyces cerevisiae*; identification and localization of *Physcomitrella patens* or *Saccharomyces cerevisiae* sequences of interest; evolutionary studies; determination of VTSRP regions required for function; modulation of a VTSRP activity; modulation of the metabolism of one or more cell functions; modulation of the transmembrane transport of one or more compounds; modulation of stress resistance; and modulation of expression of VTSRP nucleic acids. In one embodiment of these methods, the VTSRP functions as an active potassium transport protein. In another embodiment of these methods, the VTSRP functions as a vesicle trafficking protein.

The moss *Physcomitrella patens* is related to other mosses such as *Ceratodon purpureus* that are capable of growth in the absence of light. Mosses like *Ceratodon* and *Physcomitrella* share a high degree of sequence identity on the DNA sequence and polypeptide level allowing the use of heterologous screening of DNA molecules with probes evolving from other mosses or organisms, thus enabling the derivation of a consensus sequence suitable for heterologous screening or functional annotation and prediction of gene functions in third species. The ability to identify such functions can therefore have significant relevance, e.g., prediction of substrate specificity of enzymes. Further, these nucleic acid molecules may serve as reference points for the mapping of moss genomes, or of genomes of related organisms.

The VTSRP nucleic acid molecules of the invention have a variety of uses. Most importantly, the nucleic acid and amino acid sequences of the present invention can be used to transform plants, thereby inducing tolerance to stresses such as drought, high salinity, and cold. The present invention therefore provides a transgenic plant transformed by a VTSRP nucleic acid, wherein expression of the nucleic acid sequence in the plant results in increased tolerance to environmental stress as compared to a wild type variety of the plant. The transgenic plant can be a monocot or a dicot. The invention further provides that the transgenic plant can be selected from maize, wheat, rye, oat, triticale, rice, barley, soybean, peanut, cotton, rapeseed, canola, manihot, pepper, sunflower, tagetes, solanaceous plants, potato, tobacco, eggplant, tomato, *Vicia* species, pea, alfalfa, coffee, cacao, tea, *Salix* species, oil palm, coconut, perennial grass, and forage crops, for example.

In particular, the present invention describes using the expression of the Sar1 small GTPase (PpgBP-1, EST203) and Rab small GTPase (PpVT-1, EST513) of *Physcomitrella patens*; and the v-SNARE protein (ScVTP-1, YMR197C, ORF3240) of *Saccharomyces cerevisiae* to engineer plants with increased growth and/or that are drought-tolerant, salt-tolerant, and/or cold-tolerant plants, and/or plants with altered water use efficiency, particularly an increased water use efficiency. As used herein, the terms and phrases "tolerance," "efficiency," "plant tolerance," and "stress tolerance," may include water use efficiency and are not limited to, for example, cold tolerance, heat tolerance, salt tolerance, and drought tolerance. This strategy has herein been demonstrated for *Arabidopsis thaliana*, but its application is not restricted to this plant. Accordingly, the invention provides a transgenic plant containing a VTSRP such as the sar1 small GTPase (PpgBP-1, EST203) as defined in SEQ ID NO:4, Rab small GTPase (PpVTP-1, EST513) as defined in SEQ ID NO:2, or V-SNARE protein (ScVTP-1, YMR197C, ORF3240) as defined in SEQ ID NO:6, wherein the plant has increased growth and/or an increased tolerance to an environmental stress selected from one or more of the group consisting of drought, increased salt, or decreased or increased temperature. In preferred embodiments, the environmental stress is drought.

Accordingly, the invention provides a method of producing a transgenic plant with a VTSRP coding nucleic acid, wherein expression of the nucleic acid(s) in the plant results in increased tolerance to environmental stress as compared to a wild type variety of the plant comprising: (a) introducing into a plant cell an expression vector comprising a VTSRP nucleic acid, and (b) generating from the plant cell a transgenic plant with a increased tolerance to environmental stress as compared to a wild type variety of the plant. The plant cell includes, but is not limited to, a protoplast, gamete producing cell, and a cell that regenerates into a whole plant. As used herein, the term "transgenic" refers to any plant, plant cell, callus, plant tissue, or plant part, that contains all or part of at least one recombinant polynucleotide. In many cases, all or part of the recombinant polynucleotide is stably integrated into a chromosome or stable extra-chromosomal element, so that it is passed on to successive generations. In preferred embodiments, the VTSRP nucleic acid encodes a protein comprising the polypeptide of SEQ ID NO:2, SEQ ID NO:4, or SEQ ID NO:6.

The present invention also provides a method of modulating a plant's growth and/or tolerance to an environmental stress comprising, modifying the expression of a VTSRP coding nucleic acid in the plant. The plant's growth and/or tolerance to the environmental stress can be increased or decreased as achieved by increasing or decreasing the expression of a VTSRP, respectively. Preferably, the plant's growth and/or tolerance to the environmental stress is increased by increasing expression of a VTSRP. Expression of a VTSRP can be modified by any method known to those of skill in the art. The methods of increasing expression of VTSRPs can be used wherein the plant is either transgenic or not transgenic. In cases when the plant is transgenic, the plant can be transformed with a vector containing any of the above described VTSRP coding nucleic acids, or the plant can be transformed with a promoter that directs expression of native VTSRP in the plant, for example. The invention provides that such a promoter can be tissue preferred, developmentally regulated, stress inducible, or a combination thereof. Alternatively, non-transgenic plants can have native VTSRP expression modified by inducing a native promoter. The expression of sar1 small GTPase (PpgBP-1, EST 203) as defined in SEQ ID NO:4, Rab small GTPase (PpVTP-1, EST 513) as defined in SEQ ID NO:2, or V-SNARE protein (ScVTP-1, Y197C, ORF3240) as defined in SEQ ID NO:6, in target plants can be accomplished by, but is not limited to, one of the following examples: (a) constitutive promoter, (b) stress-inducible promoter, (c) chemical-induced promoter, and (d) engineered promoter overexpression with, for example, zinc-finger derived transcription factors (Greisman and Pabo, 1997, Science 275:657).

In a preferred embodiment, transcription of the VTSRP is modulated using zinc-finger derived transcription factors (ZFPs) as described in Greisman and Pabo, 1997, Science 275:657 and manufactured by Sangamo Biosciences, Inc. These ZFPs comprise both a DNA recognition domain and a functional domain that causes activation or repression of a target nucleic acid such as a VTSRP nucleic acid. Therefore, activating and repressing ZFPs can be created that specifically recognize the VTSRP promoters described above and used to increase or decrease VTSRP expression in a plant, thereby modulating the growth and/or stress tolerance of the plant. The present invention also includes identification of the homologs of sar1 small GTPase (PpgBP-1, EST 203) as defined in SEQ ID NO:4, Rab small GTPase (PpVTP-1, EST 513) as defined in SEQ ID NO:2, and V-SNARE protein (SCVTP-1, Y197C, ORF 3240) as defined in SEQ ID NO:6 in a target plant, as well as the homolog's promoter. The invention also provides a method of increasing expression of a gene of interest within a host cell as compared to a wild type variety of the host cell, wherein the gene of interest is transcribed in response to a VTSRP, comprising: (a) transforming the host cell with an expression vector comprising a VTSRP coding nucleic acid, and (b) expressing the VTSRP within the host cell, thereby increasing the expression of the gene transcribed in response to the VTSRP, as compared to a wild type variety of the host cell.

In addition to introducing the VTSRP nucleic acid sequences into transgenic plants, these sequences can also be used to identify an organism as being *Physcomitrella patens* or *Saccharomyces cerevisiae*, or a close relative thereof. Also, they may be used to identify the presence of *Physcomitrella patens* or *Saccharomyces cerevisiae*, or a relative thereof in a mixed population of microorganisms. The invention provides the nucleic acid sequences of a number of *Physcomitrella patens* or *Saccharomyces cerevisiae* genes; by probing the extracted genomic DNA of a culture of a unique or mixed population of microorganisms under stringent conditions with a probe spanning a region of a *Physcomitrella patens* or *Saccharomyces cerevisiae* gene that is unique to this organism, one can ascertain whether this organism is present.

Further, the nucleic acid and polypeptide molecules of the invention may serve as markers for specific regions of the genome. This has utility not only in the mapping of the genome, but also in functional studies of *Physcomitrella patens* or *Saccharomyces cerevisiae* polypeptides. For example, to identify the region of the genome to which a particular *Physcomitrella patens* DNA-binding polypeptide binds, the *Physcomitrella patens* genome could be digested, and the fragments incubated with the DNA-binding polypeptide. Those fragments that bind the polypeptide may be additionally probed with the nucleic acid molecules of the invention, preferably with readily detectable labels. Binding of such a nucleic acid molecule to the genome fragment enables the localization of the fragment to the genome map of *Physcomitrella patens*, and, when performed multiple times with different enzymes, facilitates a rapid determination of the nucleic acid sequence to which the polypeptide binds. Further, the nucleic acid molecules of the invention may be sufficiently identical to the sequences of related species such that these nucleic acid molecules may serve as markers for the construction of a genomic map in related mosses.

The VTSRP nucleic acid molecules of the invention are also useful for evolutionary and polypeptide structural studies. The vesicle trafficking processes in which the molecules of the invention participate are utilized by a wide variety of prokaryotic and eukaryotic cells; by comparing the sequences of the nucleic acid molecules of the present invention to those encoding similar enzymes from other organisms, the evolutionary relatedness of the organisms can be assessed. Similarly, such a comparison permits an assessment of which regions of the sequence are conserved and which are not, which may aid in determining those regions of the polypeptide that are essential for the functioning of the enzyme. This type of determination is of value for polypeptide engineering studies and may give an indication of what the polypeptide can tolerate in terms of mutagenesis without losing function.

Manipulation of the VTSRP nucleic acid molecules of the invention may result in the production of VTSRPs having functional differences from the wild-type VTSRPs. These polypeptides may be improved in efficiency or activity, may be present in greater numbers in the cell than is usual, or may be decreased in efficiency or activity.

There are a number of mechanisms by which the alteration of a VTSRP of the invention may directly affect growth and/or stress response and/or stress tolerance. In the case of plants expressing VTSRPs, increased vesicle traffic activity can lead to a change in cellular transport of proteins, which can lead to improved plant water use efficiency.

The effect of the genetic modification in plants, *C. glutamicum*, fungi, algae, or ciliates on growth and/or stress tolerance can be assessed by growing the modified microorganism or plant under less than suitable conditions and then analyzing the growth characteristics and/or metabolism of the plant. Such analysis techniques are well known to one skilled in the art, and include dry weight, wet weight, polypeptide synthesis, carbohydrate synthesis, lipid synthesis, evapotranspiration rates, general plant and/or crop yield, flowering, reproduction, seed setting, root growth, respiration rates, photosynthesis rates, etc. (Applications of HPLC in Biochemistry in: Laboratory Techniques in Biochemistry and Molecular Biology, vol. 17; Rehm et al., 1993 Biotechnology, vol. 3, Chapter III: Product recovery and purification, page 469-714, VCH: Weinheim; Belter, P. A. et al., 1988, Bioseparations: downstream processing for biotechnology, John Wiley and Sons; Kennedy, J. F. and Cabral, J. M. S., 1992, Recovery processes for biological materials, John Wiley and Sons; Shaeiwitz, J. A. and Henry, J. D., 1988, Biochemical separations, in: Ulmann's Encyclopedia of Industrial Chemistry, vol. B3, Chapter 11, page 1-27, VCH: Weinheim; and Dechow, F. J., 1989, Separation and purification techniques in biotechnology, Noyes Publications).

For example, yeast expression vectors comprising the nucleic acids disclosed herein, or fragments thereof, can be constructed and transformed into *Saccharomyces cerevisiae* using standard protocols. The resulting transgenic cells can then be assayed for fail or alteration of their increased growth and/or tolerance to drought, salt, and temperature stresses. Similarly, plant expression vectors comprising the nucleic acids disclosed herein, or fragments thereof, can be constructed and transformed into an appropriate plant cell such as *Arabidopsis*, soy, rape, maize, wheat, *Medicago truncatula*, etc., using standard protocols. The resulting transgenic cells and/or plants derived there from can then be assayed for fail or alteration of their increased growth and/or tolerance to drought, salt, and temperature stresses.

Additionally, the sequences disclosed herein, or fragments thereof, can be used to generate knockout mutations in the genomes of various organisms, such as bacteria, mammalian cells, yeast cells, and plant cells (Girke, T., 1998, The Plant Journal 15:3948). The resultant knockout cells can then be evaluated for their ability or capacity to tolerate various stress conditions, their response to various stress conditions, and the effect on the phenotype and/or genotype of the mutation. For other methods of gene inactivation, see U.S. Pat. No. 6,004, 804 "Non-Chimeric Mutational Vectors" and Puttaraju et al., 1999, Spliceosome-mediated RNA trans-splicing as a tool for gene therapy, Nature Biotechnology 17:246-252.

The aforementioned mutagenesis strategies for VTSRPs resulting in increased growth and/or stress tolerance are not meant to be limiting; variations on these strategies will be readily apparent to one skilled in the art. Using such strategies, and incorporating the mechanisms disclosed herein, the nucleic acid and polypeptide molecules of the invention may be utilized to generate algae, ciliates, plants, fungi, or other microorganisms like *C. glutamicum* expressing mutated VTSRP nucleic acid and polypeptide molecules such that the growth and/or stress tolerance is improved.

The present invention also provides antibodies that specifically bind to a VTSRP, or a portion thereof, as encoded by a nucleic acid described herein. Antibodies can be made by many well-known methods (See, e.g., Harlow and Lane, "Antibodies; A Laboratory Manual," Cold Spring Harbor Laboratory, Cold Spring Harbor, N.Y., (1988)). Briefly, purified antigen can be injected into an animal in an amount and in intervals sufficient to elicit an immune response. Antibodies can either be purified directly, or spleen cells can be obtained from the animal. The cells can then fused with an immortal cell line and screened for antibody secretion. The antibodies can be used to screen nucleic acid clone libraries for cells secreting the antigen. Those positive clones can then be sequenced. (See, for example, Kelly et al., 1992, Bio/Technology 10: 163-167; Bebbington et al., 1992, Bio/Technology 10:169-175).

The phrases "selectively binds" and "specifically binds" with the polypeptide refer to a binding reaction that is determinative of the presence of the polypeptide in a heterogeneous population of polypeptides and other biologics. Thus, under designated immunoassay conditions, the specified antibodies bound to a particular polypeptide do not bind in a significant amount to other polypeptides present in the sample. Selective binding of an antibody under such conditions may require an antibody that is selected for its specificity for a particular polypeptide. A variety of immunoassay formats may be used to select antibodies that selectively bind with a particular polypeptide. For example, solid-phase ELISA immunoassays are routinely used to select antibodies selectively immunoreactive with a polypeptide. See Harlow and Lane, "Antibodies, A Laboratory Manual" Cold Spring Harbor Publications, New York, (1988), for a description of immunoassay formats and conditions that could be used to determine selective binding.

In some instances, it is desirable to prepare monoclonal antibodies from various hosts. A description of techniques for preparing such monoclonal antibodies may be found in Stites et al., eds., "Basic and Clinical Immunology," (Lange Medical Publications, Los Altos, Calif., Fourth Edition) and references cited therein, and in Harlow and Lane "Antibodies, A Laboratory Manual" Cold Spring Harbor Publications, New York; 1988.

Throughout this application, various publications are referenced. The disclosures of all of these publications and those references cited within those publications in their entireties are hereby incorporated by reference into this application in order to more fully describe the state of the art to which this invention pertains.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Example 1

Growth of *Physcomitrella patens* Cultures

For this study, plants of the species *Physcomitrella patens* (Hedw.) B. S. G. from the collection of the genetic studies section of the University of Hamburg were used. They originate from the strain 16/14 collected by H. L. K. Whitehouse in Gransden Wood, Huntingdonshire (England), which was subcultured from a spore by Engel (1968, Am. J. Bot. 55, 438446). Proliferation of the plants was carried out by means of spores and by means of regeneration of the gametophytes. The protonema developed from the haploid spore as a chloroplast-rich chloronema and chloroplast-low caulonema, on which buds formed after approximately 12 days. These grew to give gametophores bearing antheridia and archegonia. After fertilization, the diploid sporophyte with a short seta and the spore capsule resulted, in which the meiospores matured.

Culturing was carried out in a climatic chamber at an air temperature of 25° C. and light intensity of 55 micromols $m^{-2}$ $s^{-1}$ (white light; Philips TL 65 W/25 fluorescent tube) and a light/dark change of 16/8 hours. The moss was either modified in liquid culture using Knop medium according to Reski and Abel (1985, Planta 165:354-358) or cultured on Knop solid medium using 1% oxoid agar (Unipath, Basingstoke, England). The protonemas used for RNA and DNA isolation were cultured in aerated liquid cultures. The protonemas were comminuted every 9 days and transferred to fresh culture medium.

Example 2

Total DNA Isolation from Plants

The details for the isolation of total DNA relate to the working up of one gram fresh weight of plant material. The materials used include the following buffers: CTAB buffer: 2% (w/v) N-cethyl-N,N,N-trimethylammonium bromide (CTAB); 100 mM Tris HCl pH 8.0; 1.4 M NaCl; 20 mM EDTA; N-Laurylsarcosine buffer: 10% (w/v) N-laurylsarcosine; 100 mM Tris HCl pH 8.0; and 20 mM EDTA.

The plant material was triturated under liquid nitrogen in a mortar to give a fine powder and transferred to 2 ml Eppendorf vessels. The frozen plant material was then covered with a layer of 1 ml of decomposition buffer (1 ml CTAB buffer, 100 μl of N-laurylsarcosine buffer, 20 μl of β-mercaptoethanol, and 10 μl of proteinase K solution, 10 mg/ml) and incubated at 60° C. for one hour with continuous shaking. The homogenate obtained was distributed into two Eppendorf vessels (2 ml) and extracted twice by shaking with the same volume of chloroform/isoamyl alcohol (24:1). For phase separation, centrifugation was carried out at 8000×g and room temperature for 15 minutes in each case. The DNA was then precipitated at −70° C. for 30 minutes using ice-cold isopropanol. The precipitated DNA was sedimented at 4° C. and 10,000 g for 30 minutes and resuspended in 180 μl of TE buffer (Sambrook et al., 1989, Cold Spring Harbor Laboratory Press: ISBN 0-87969-309-6). For further purification, the DNA was treated with NaCl (1.2 M final concentration) and precipitated again at −70° C. for 30 minutes using twice the volume of absolute ethanol. After a washing step with 70% ethanol, the DNA was dried and subsequently taken up in 50 μl of $H_2O$+RNAse (50 mg/ml final concentration). The DNA was dissolved overnight at 4° C., and the RNAse digestion was subsequently carried out at 37° C. for 1 hour. Storage of the DNA took place at 4° C.

Example 3

Isolation of Total RNA and Poly-(A)+RNA and cDNA Library Construction from *Physcomitrella patens*

For the investigation of transcripts, both total RNA and poly-(A)$^+$ RNA were isolated. The total RNA was obtained from wild-type 9 day old protonemata following the GTC-method (Reski et al., 1994, Mol. Gen. Genet., 244:352-359). The Poly(A)$^+$ RNA was isolated using Dyna BeadS® (Dynal, Oslo, Norway) following the instructions of the manufacturer's protocol. After determination of the concentration of the RNA or of the poly(A)+RNA, the RNA was precipitated by addition of 1/10 volumes of 3 M sodium acetate pH 4.6 and 2 volumes of ethanol and stored at −70° C.

For cDNA library construction, first strand synthesis was achieved using Murine Leukemia Virus reverse transcriptase (Roche, Mannheim, Germany) and oligo-d(T)-primers, second strand synthesis by incubation with DNA polymerase I, Klenow enzyme and RNAseH digestion at 12° C. (2 hours), 16° C. (1 hour), and 22° C. (1 hour). The reaction was stopped by incubation at 65° C. (10 minutes) and subsequently transferred to ice. Double stranded DNA molecules were blunted by T4-DNA-polymerase (Roche, Mannheim) at 37° C. (30 minutes). Nucleotides were removed by phenol/chloroform extraction and Sephadex G50 spin columns. EcoRI adapters (Pharmacia, Freiburg, Germany) were ligated to the cDNA ends by T4-DNA-ligase (Roche, 12° C., overnight) and phosphorylated by incubation with polynucleotide kinase (Roche, 37° C., 30 minutes). This mixture was subjected to separation on a low melting agarose gel. DNA molecules larger than 300 base pairs were eluted from the gel, phenol extracted, concentrated on Elutip-D-columns (Schleicher and Schuell, Dassel, Germany), and were ligated to vector arms and packed into lambda ZAPII phages or lambda ZAP-Express phages using the Gigapack Gold Kit (Stratagene, Amsterdam, Netherlands) using material and following the instructions of the manufacturer.

Example 4

Sequencing and Function Annotation of *Physcomitrella patens* ESTs cDNA libraries as described in Example 3 were used for DNA sequencing according to standard methods, and in particular, by the chain termination method using the ABI PRISM Big Dye Terminator Cycle Sequencing Ready Reaction Kit (Perkin-Elmer, Weiterstadt, Germany). Random sequencing was carried out subsequent to preparative plasmid recovery from cDNA libraries via in vivo mass excision, retransformation, and subsequent plating of DH10B on agar plates (material and protocol details from Stratagene, Amsterdam, Netherlands). Plasmid DNA was prepared from overnight grown *E. coli* cultures grown in Luria-Broth medium containing ampicillin (See Sambrook et al., 1989, Cold Spring Harbor Laboratory Press: ISBN 0-87969-309-6) on a Qiagene DNA preparation robot (Qiagen, Hilden) according to the manufacturer's protocols. Sequencing primers with the following nucleotide sequences were used:

```
5'-CAGGAAACAGCTATGACC-3'      SEQ ID NO: 7

5'-CTAAAGGGAACAAAAGCTG-3'     SEQ ID NO: 8

5'-TGTAAAACGACGGCCAGT-3'.     SEQ ID NO: 9
```

Sequences were processed and annotated using the software package EST-MAX commercially provided by Bio-Max (Munich, Germany). The program incorporates practically all bioinformatics methods important for functional and structural characterization of protein sequences. For reference, see the website at pedant.mips.biochem.mpg.de. The most important algorithms incorporated in EST-MAX are: FASTA (Very sensitive sequence database searches with estimates of statistical significance; Pearson W. R., 1990, Rapid and sensitive sequence comparison with FASTP and FASTA. Methods Enzymol. 183:63-98); BLAST (Very sensitive sequence database searches with estimates of statistical significance. Altschul S. F. et al., Basic local alignment search tool, Journal of Molecular Biology 215:403-10); PREDATOR (High-accuracy secondary structure prediction from single and multiple sequences. Frishman, D. and Argos, P., 1997, 75% accuracy in protein secondary structure prediction. Proteins, 27:329-335); CLUSTALW: Multiple sequence alignment. Thompson, J. D. et al., 1994, CLUSTAL W (improving the sensitivity of progressive multiple sequence alignment through sequence weighting, positions-specific gap penalties and weight matrix choice, Nucleic Acids Research, 22:4673-4680); TMAP (Transmembrane region prediction from multiply aligned sequences. Persson, B. and Argos, P., 1994, Prediction of transmembrane segments in proteins utilizing multiple sequence alignments. J. Mol. Biol. 237:182-192); ALOM2 (Transmembrane region prediction from single sequences. Klein, P. et al., Prediction of protein function from sequence properties: A discriminate analysis of a database. Biochim. Biophys. Acta 787:221-226 (1984). Version 2 by Dr. K. Nakai); PROSEARCH (Detection of PROSITE protein sequence patterns. Kolakowski L. F. Jr., Leunissen J. A. M., Smith J. E., 1992, ProSearch: fast searching of protein sequences with regular expression patterns related to protein structure and function. Biotechniques 13, 919-921); BLIMPS (Similarity searches against a database of ungapped blocks, J. C. Wallace and Henikoff S., 1992); PATMAT (a searching and extraction program for sequence, pattern and block queries and databases, CABIOS 8:249-254. Written by Bill Alford).

Example 5

Identification of ORFs Corresponding to PpgBP-1, PpVTP-1, and ScVTP-1

The *Physcomitrella patens* partial cDNAs (ESTs) for partial sar1 small GTPase (PpgBP-1, EST 203) and Rab small GTPase (PpVTP-1, EST 513) were identified in the *Physcomitrella patens* EST sequencing program using the program EST-MAX through BLAST analysis. These particular clones, which were found to encode vesicle trafficking proteins, were chosen for further analyses.

TABLE 1

Degree of amino acid identity and similarity of PpGBP-1 and other vesicle trafficking proteins (pairwise comparison was used: gap penalty: 10; gap extension penalty: 0.1; score matrix: blosum62); degree of amino acid identity and similarity of PpGBP-1 and other homologous proteins (pairwise comparison program was used: gap penalty: 10; gap extension penalty: 0.1; score matrix: blosum62)

| Swiss-Prot # | Q9SDQ5 | P52884 | O04834 | O24110 | Q01474 |
|---|---|---|---|---|---|
| Protein name | Small GTP-binding protein Sar1BNT | GTP-binding protein Sar2 | GTP-binding protein Sar1A | Small GTP-binding protein | GTP-binding protein Sar1B |
| Species | *Nicotiana tabacum* (Common tobacco) | *Lycopersicon esculentum* (Tomato) | *Arabidopsis thaliana* (Mouse-ear cress) | *Nicotiana plumbaginifolia* (Leadwort-leaved tobacco) | *Arabidopsis thaliana* (Mouse-ear cress) |
| Identity % | 84% | 84% | 83% | 83% | 82% |
| Similarity % | 94% | 93% | 93% | 93% | 92% |

The PpgBP-1 amino acid sequence also has significant homology to several sequences disclosed in published patent applications as is shown in Table 2.

To isolate the clones encoding PpgBP-1 (SEQ ID NO:4) and PpVTP-1 (SEQ ID NO:2) from *Physcomitrella patens*, cDNA libraries were created with SMART RACE cDNA

TABLE 2

| Name | Barley 01 | Arabidopsis 02 | Arabidopsis 03 | Arabidopsis 04 | Zea mays 05 | Zea mays 06 | Zea mays 07 | Zea mays 08 |
|---|---|---|---|---|---|---|---|---|
| Patent | WO03/057877 | | | EP 1033405 A2 | | | | |
| Species | Barley | *A. thaliana* | *A. thaliana* | *A. thaliana* | Zea mays | Zea mays | Zea mays | Zea mays |
| Identity % | 82 | 82 | 82 | 81 | 81 | 81 | 81 | 80 |
| Similarity % | 92 | 92 | 92 | 91 | 91 | 91 | 91 | 90 |

TABLE 3

Degree of amino acid identity and similarity of Rab small GTPase (PpVTP-1, EST 513) and other vesicle trafficking proteins (pairwise comparison was used: gap penalty: 10; gap extension penalty: 0.1; score matrix: blosum62)

| Polypeptide name | Arabidopsis 01 | Arabidopsis 02 |
|---|---|---|
| Patent | EP1033405-A2 | EP1033405-A2 |
| Species | *A. thaliana* | *A. thaliana* |
| Identity % | 83 | 83 |
| Similarity % | 90 | 90 |

The ORF 3240 gene from *Saccharomyces cerevisiae*, encoding a vSNARE polypeptide, was first described in European Patent Application No. 03022225.1 by Metanomics, Inc. filed Sep. 30, 2003. The Metanomics patent application is hereby incorporated by reference in its entirety. The ORF 3240 gene was isolated using the standard protocol of Pfu DNA polymerase or a PfuITaq DNA polymerase mix (Herculase) for the amplification procedure. Amplified ORF fragments were analyzed by gel electrophoresis. Each primer consists of a universal 5' end and ORF specific 3' end whereby the universal sequences differ for the forward and reverse primers (Forward primer sequence contained an EcoRI for yeast or SmaI for *E. coli* and the reverse primer sequence a SmaI for yeast or SacI for *E. coli*) allowing a unidirectional cloning. PCR reactions for the amplification included: 1×PCR buffer, 0.2 mM dNTP, 100 ng *Saccharomyces cerevisiae* genomic DNA (S288C) or 60 ng genomic DNA *Escherichia coli* K-12 (MG1655), 25 pmol reverse primer, 2.5μ Pfu or Herculase DNA polymerase. The conditions consisted of: 1 cycle for 3' at 94° C.; followed by 25 cycles of 30" at 94° C., 30" at 55° C., and 5-6' at 72° C.; followed by 1 cycle for 610' at 72° C., then at 4° C. indefinitely. The forward sequence for ScVTP-1 (ORF 3240) is 5'-GGAATTCC AGCTGACCAC-CATGAGTTCCCTATTAATATCATACGA-3' (SEQ ID NO:10). The reverse sequence for ScVTP-1 (ORF 3240) is 5'-gatccccgggaattgccatgctatt gattgtttgttccacggact-3' (SEQ ID NO:11).

Example 6

Cloning of the Full-Length *Physcomitrella patens* cDNA Encoding for PpgBP-1 and PpVTP-1

To isolate the full-length clones encoding the Sar1small GTPase (PpgBP-1, EST 203) (SEQ ID NO:3) and the Rab small GTPase (PpVTP-1, EST 513) (SEQ ID NO:1) from *Physcomitrella patens*, cDNA libraries were created with SMART RACE cDNA Amplification kit (Clontech Laboratories) following the manufacturer's instructions.

Amplification kit (Clontech Laboratories) following manufacturer's instructions. Total RNA isolated as described in Example 3 was used as the template. The cultures were treated prior to RNA isolation as follows: Salt Stress: 2, 6, 12, 24, 48 h with 1-M NaCl-supplemented medium; Cold Stress: 4 C for the same time points as for salt; Drought Stress: cultures were incubated on dry filter paper for the same time points above. RNA was then pulled and used for isolation.

5' RACE Protocol—The EST sequences PpgBP-1 and PpVTP-1, identified from the database search as described in Example 5 were used to design oligos for RACE (See Table 4). The extended sequences for these genes were obtained by performing Rapid Amplification of cDNA Ends polymerase chain reaction (RACE PCR) using the Advantage 2 PCR kit (Clontech Laboratories) and the SMART RACE cDNA amplification kit (Clontech Laboratories) using a Biometra T3 Thermocycler following the manufacturer's instructions.

The sequences obtained from the RACE reactions contained the 5' end of the full-length coding regions of for PpgBP-1 and PpVTP-1 and were used to design oligos for full-length cloning of the respective genes (see below under "Full-length Amplification").

Full-Length Amplification. Full-length clones corresponding to PpgBP-1 (SEQ ID NO:3) and PpVTP-1 (SEQ ID NO:1) were obtained by performing polymerase chain reaction (PCR) with gene-specific primers (See Table 4) and the original EST as the template. The conditions for the reaction were standard conditions with PWO DNA polymerase (Roche). PCR was performed according to standard conditions and to manufacturer's protocols (Sambrook et al., 1989, Molecular Cloning, A Laboratory Manual, 2nd Edition, Cold Spring Harbor Laboratory Press, Cold Spring Harbor, N.Y., Biometra T3 Thermocycler). The parameters for the reaction were: five minutes at 94° C. followed by five cycles of one minute at 94° C., one minute at 50° C. and 1.5 minutes at 72° C. This was followed by twenty five cycles of one minute at 94° C., one minute at 65° C. and 1.5 minutes at 72° C. Full-length clones for PpgBP-1 (SEQ ID NO:3) and PPVTP-1 (SEQ ID NO:1) were isolated by repeating the RACE method but using the gene-specific primers as given in Table 4.

The amplified fragments were then extracted from agarose gel with a QIAquick Gel Extraction Kit (Qiagen) and ligated into the TOPO pCR 2.1 vector (Invitrogen) following manufacture's instructions. Recombinant vectors were transformed into Top10 cells (Invitrogen) using standard conditions (Sambrook et al. 1989. Molecular Cloning, A Laboratory Manual, 2nd Edition, Cold Spring Harbor Laboratory Press, Cold Spring Harbor, N.Y.). Transformed cells were selected for on LB agar containing 100 μg/mil carbenicillin, 0.8 mg X-gal (5-bromo-4-chloro-3-indolyl-β-D-galactoside) and 0.8 mg IPTG (isopropylthio-β-D-galactoside)

grown overnight at 37° C. White colonies were selected and used to inoculate 3 ml of liquid LB containing 100 μg/ml ampicillin and grown overnight at 37° C. Plasmid DNA was extracted using the QIAprep Spin Miniprep Kit (Qiagen) following manufacture's instructions. Analyses of subsequent clones and restriction mapping were performed according to standard molecular biology techniques (Sambrook et al., 1989, Molecular Cloning, A Laboratory Manual, 2nd Edition, Cold Spring Harbor Laboratory Press, Cold Spring Harbor, N.Y.).

prep Kit (Qiagen) following manufacturer's instructions. Analyses of subsequent clones and restriction mapping were performed according to standard molecular biology techniques (Sambrook et al., 1989, Molecular Cloning, A Laboratory Manual. 2nd Edition, Cold Spring Harbor Laboratory Press, Cold Spring Harbor, N.Y.).

Both the pGMBS vector and p1bxSuperGUS vector were digested with XbaI and KpnI (Roche) according to manufacturer's instructions, excising the gentamycin cassette from pGMBS and producing the backbone from the

TABLE 4

Scheme and primers used for cloning of full-length clones

| Gene | Sites in the final product | Isolation Method | Primers Race | Primer Full-length PCR |
|------|---------------------------|------------------|--------------|------------------------|
| PpGBP-1 | XmaI/HpaI | 5' RACE and RT-PCR for Full-length clone | (SEQ ID NO: 12) TGCCAGCATTG TCGAGACCCA GAAA | RC586 (SEQ ID NO: 13) ATCCCGGGTCCGTAGATACCA AGGCTGGT RC587 (SEQ ID NO: 14) GCGTTAACTCGTCGCTCTTAA ACACCGAGCTAAG |
| PpVTP-1 | XmaI/SacI | 5' RACE and RT-PCR for Full-length clone | (SEQ ID NO: 12) TGCCAGCATTG TCGAGACCCA GAAA | RC693 (SEQ ID NO: 23) ATCCCGGGAGATAGCCCAGA AGGCCGATCC RC694 (SEQ ID NO: 22) GCGAGCTCCACACCAATCTCC AGACTCCACCA |

Example 7

Engineering Stress-Tolerant *Arabidopsis* Plants by Overexpressing the PpgBP-1, PpVTP-1, or ScVTP-1 Gene Binary Vector Construction: PBPS-JH001. The plasmid construct pLMNC53 (Mankin, 2000, Ph.D. thesis, University of North Carolina) was digested with HindIII (Roche) and blunt-end filled with Klenow enzyme and 0.1 mM dNTTs according to manufacturer's instructions. This fragment was purified by agarose gel and extracted via the QIAquick Gel Extraction kit (Qiagen) according to manufacturer's instructions. The purified fragment was then digested with EcoRI (Roche), purified by agarose gel, and extracted via the QIAquick Gel Extraction kit (Qiagen) according to manufacturer's instructions. The resulting 1.4 kilobase fragment, the gentamycin cassette, included the nos promoter, aacCI gene, and the g7 terminator.

The vector pBlueScript was digested with EcoRI and SmaI (Roche) according to manufacturer's instructions, and the resulting fragment was extracted from agarose gel with a QIAquick Gel Extraction Kit (Qiagen) according to manufacturer's instructions. The digested pBlueScript vector and the gentamycin cassette fragments were ligated with T4 DNA Ligase (Roche) according to manufacturer's instructions, joining the two respective EcoRI sites and joining the blunt-ended HindIII site with the SmaI site.

The recombinant vector (pGMBS) was transformed into Top10 cells (Invitrogen) using standard conditions. Transformed cells were selected for on LB agar containing 100 μg/ml carbenicillin, 0.8 mg X-gal (5-bromo4-chloro-3-indolyl-β-D-galactoside) and 0.8 mg IPTG (isopropylthio-β-D-galactoside), grown overnight at 37° C. White colonies were selected and used to inoculate 3 ml of liquid LB containing 100 μg/ml ampicillin and grown overnight at 37° C. Plasmid DNA was extracted using the QIAprep Spin Minip1bxSuperGUS vector. The resulting fragments were extracted from agarose gel with a QIAquick Gel Extraction Kit (Qiagen) according to manufacturer's instructions. These two fragments were ligated with T4 DNA ligase (Roche) according to manufacturer's instructions.

The resulting recombinant vector (pBPS-JH001) was transformed into Top10 cells (Invitrogen) using standard conditions. Transformed cells were selected for on LB agar containing 100 μg/ml carbenicillin, 0.8 mg X-gal (5-bromo4-chloro-3-indolyl-β-D-galactoside) and 0.8 mg IPTG (isopropylthio-β-D-galactoside), grown overnight at 37° C. White colonies were selected and used to inoculate 3 ml of liquid LB containing 100 μg/ml ampicillin and grown overnight at 37° C. Plasmid DNA was extracted using the QIAprep Spin Miniprep Kit (Qiagen) following manufacturer's instructions. Analyses of subsequent clones and restriction mapping were performed according to standard molecular biology techniques (Sambrook et al., 1989, Molecular Cloning, A Laboratory Manual, 2nd Edition, Cold Spring Harbor Laboratory Press, Cold Spring Harbor, N.Y.).

Subcloning of PpgBP-1 and PpVTP-1 into the Binary Vector. The fragments containing the different *Physcomitrella patens* vesicle trafficking proteins were excised from the recombinant PCR2.1 TOPO vectors by double digestion with restriction enzymes (See Table 5) according to manufacturer's instructions. The subsequent fragments were excised from agarose gel with a QIAquick Gel Extraction Kit (Qiagen) according to manufacturer's instructions, ligated into binary vectors, cleaved with appropriate enzymes (See Table 5), and dephosphorylated prior to ligation. The resulting recombinant vectors contained the corresponding vesicle trafficking protein in the sense orientation under the control of the constitutive superpromoter, a fusion of octopine and mannopine synthase mas promoter/activator (Ni et al., 1995, Plant J. 7:661-676).

TABLE 5

Listed are the names of the constructs of the *Physcomitrella patens* vesicle trafficking proteins used for plant transformation.

| Gene | Enzymes used to generate gene fragment | Enzymes used to restrict vector | Binary Vector Construct |
|---|---|---|---|
| PpGBP-1 | XmaI/HpaI | XmaI/Ecl136 | pBPSLVM162 |
| PpVTP-1 | XamI/SacI | XamI/SacI | pBPSSY020 |

Subcloning of ScVTP-1 into the Binary Vector. The ScVTP-1 gene (YMR 197C, ORF 3240) was subcloned into a binary vector 1bxbigResgen that is based on a modified pPZP binary vector backbone. The vector comprised a selection marker gene for bacterial selection (Hajukeiwicz et al., 1994, Plant Mol. Biol. 25:989-994) and the bar gene driven by the mas1 promoter on its T-DNA (Velten et al., 1984, EMBO J. 3: 2723-2730; Mengiste, et al., 1997, Plant J., 12: 945-948). In addition, the T-DNA contained a promoter (Kay et al., 1987, Science 236:1299-1302) in front of a cloning cassette which was followed by the nos terminator (Depicker et al., J. Mol. Appl. Gen. 1(6):561-573). The cloning cassette consisted of the sequence: 5'-GGAATTCCAGCTGACCAC-CATGGCAATTCCCGGGGATC-3' (SEQ ID NO:17). Other selection systems and promoters are known in the art and are similarly capable of use in the present invention (e.g., AHAS marker, ubiquitin promoter (Callis et al., J. Biol. Chem. 1990, 265:12486-12493; U.S. Pat. No. 5,510,474; U.S. Pat. No. 6,020,190; Kawalleck et al., 1993, Plant Mol. Biol. 21:673-684), 34S promoter (GenBank Accession Numbers M59930 and X16673).

The binary vector and the ScVTP-1 gene (100 ng) were digested with EcoRI and SmaI using the standard protocol provided by the supplier (MBI Fermentas, Germany). The ScVTP-1 gene was purified using a Qiagen column (Qiagen, Hilden, Germany), and was ligated with the restriction digested binary vector (30 ng) using standard procedures (Maniatis et al.).

*Agrobacterium* Transformation. The recombinant vectors were transformed into *Agrobacterium tumefaciens* C58C1 and PMP90 according to standard conditions (Hoefgen and Willmitzer, 1990; Koncz and Schell, 1986, Mol. Gen. Genet. 204:383-396).

Plant Transformation. *Arabidopsis thaliana* ecotype C24 were grown and transformed according to standard conditions (Bechtold, 1993, Acad. Sci. Paris. 316:1194-1199; Bent et al., 1994, Science 265:1856-1860).

Screening of Transformed Plants Comprising *Physcomitrella* Genes. T1 seeds were sterilized according to standard protocols (Xiong et al., 1999, Plant Molecular Biology Reporter 17: 159-170). Seeds were selected on ½ Murashige and Skoog media (MS) (Sigma-Aldrich), 0.6% agar and supplemented with 1% sucrose, and 2 µg/ml benomyl (Sigma-Aldrich). Seeds on plates were vernalized for four days at 4° C. The seeds were germinated in a climatic chamber at an air temperature of 22° C. and light intensity of 40 micromols $m^{-2}$ $s^{-1}$ (white light; Philips TL 65 W/25 fluorescent tube) and 16 hours light and 8 hours dark day length cycle. Transformed seedlings were selected after 14 days and transferred to ½ MS media supplemented with 0.6% agar, 1% sucrose, and allowed to recover for five to seven days.

Drought Tolerance Screening of Transformed Plants Comprising *Physcomitrella* or *Saccharomyces* Genes. T1 seedlings were transferred to dry, sterile filter paper in a petri dish and allowed to desiccate for two hours at 80% RH (relative humidity) in a Sanyo Growth Cabinet MLR-350H, micromols $m^{-2}$ $s^{-1}$ (white light; Philips TL 65 W/25 fluorescent tube). The RH was then decreased to 60%, and the seedlings were desiccated further for eight hours. Seedlings were then removed and placed on ½ MS 0.6% agar plates supplemented with 2 µg/ml benomyl (Sigma-Aldrich) and scored after five days. The transgenic plants were then screened for their improved drought tolerance.

Under drought stress conditions, PpgBP-1 (sar1, EST 203)-overexpressing *Arabidopsis thaliana* plants showed a 45% survival rate to the drought stress (9 survivors from 20 stressed plants), as compared to the 28% survival rate that was demonstrated by the untransformed control plants (16 survivor from 57 stressed plants).

Transgenic *Arabidopsis* plants comprising the ScVTP-1 (ORF 3240, YMR197C) gene were screened for their tolerance to drought in three separate experiments. In the first experiment, the plants were subjected to a period of twelve days of drought conditions. After the twelve days, the transgenic plants were screened for their improved drought tolerance. Transgenic plants containing the ScVTP-1 transgene (14 plants) retained viability, as shown by their turgid appearance and maintenance of green color, for an average of 0.57 days beyond the untransformed wild type control plant.

In the second experiment, one plant from several independent transgenic lines were used. Three week old transgenic plants containing the ScVTP-1 transgene were subjected to drought stress conditions. Transgenic plants containing the ScVTP-1 transgene (9 plants) retained viability, as shown by their turgid appearance and maintenance of green color, for an average of 1.22 days beyond the untransformed wild type control plant.

In the third experiment, several plants from one independent transgenic line were used. Three week old transgenic plants containing the ScVTP-1 transgene were subjected to drought stress conditions. The results are shown in Table 6. Transgenic plants containing the ScVTP-1 transgene retained a significantly higher photosynthetic yield than the untransformed wild type control plant. For ScVTP-1, the average result of 5 replicate plants is listed; for the wild type plants, the average result of 20-25 plants is listed.

TABLE 6

| | Photosynthetic yield (6 days after final watering) | Photosynthetic yield (10 days after final watering) | Photosynthetic yield (14 days after final watering) |
|---|---|---|---|
| ScVTP-1 | 751 | 723 | 63 |
| Wild type | 736 | 709 | 20 |

Freezing Tolerance Screening of Transformed Plants Comprising *Physcomitrella* Genes. Seedlings were moved to petri dishes containing ½ MS 0.6% agar supplemented with 2% sucrose and 2 µg/ml benomyl. After four days, the seedlings were incubated at 4° C. for 1 hour and then covered with shaved ice. The seedlings were then placed in an Environmental Specialist ES2000 Environmental Chamber and incubated for 3.5 hours beginning at −1.0° C., and decreasing −1° C. each hour. The seedlings were then incubated at −5.0° C. for 24 hours and then allowed to thaw at 5° C. for 12 hours. The water was poured off, and the seedlings were scored after 5 days.

The transgenic plants are screened for their improved cold tolerance, demonstrating that transgene expression confers cold tolerance. Under freezing stress conditions, PpgBP-1-overexpressing *Arabidopsis thaliana* plants showed a 60% survival rate to the freeze stress (15 survivors from 25 stressed plants), as compared to the 2% survival rate that was demonstrated by the untransformed control plants (1 survivor from 48 stressed plants).

TABLE 7

Summary of the freezing stress tests

| | Freezing Stress Test | | |
|---|---|---|---|
| Gene Name | Number of survivors | Total number of plants | Percentage of survivors |
| PpGBP-1 | 15 | 25 | 60% |
| Control | 1 | 48 | 2% |

Salt Tolerance Screening. Seedlings are transferred to filter paper soaked in ½ MS and placed on ½ MS 0.6% agar supplemented with 2 µg/ml benomyl the night before the salt tolerance screening. For the salt tolerance screening, the filter paper with the seedlings is moved to stacks of sterile filter paper, soaked in 50 mM NaCl, in a petri dish. After two hours, the filter paper with the seedlings is moved to stacks of sterile filter paper, soaked with 200 mM NaCl, in a petri dish. After two hours, the filter paper with the seedlings is moved to stacks of sterile filter paper, soaked in 600 mM NaCl, in a petri dish. After 10 hours, the seedlings are moved to petri dishes containing ½ MS 0.6% agar supplemented with 2 µg/ml benomyl. The seedlings are scored after 5 days.

Transgenic plants overexpressing the transgene are screened for their improved salt tolerance demonstrating that transgene expression confers salt tolerance.

Growth Screen Under Water-Limited Conditions. The PpgBP-1, PpVTP-1, and ScVTP-1 genes were overexpressed in *Arabidopsis thaliana* under the control of the constitutive superpromoter as described above (Ni et al., 1995, Plant J. 7:661 676). The transgenic lines were grown in a growth chamber for three weeks at approximately 50% of the maximum water-holding capacity of the soil. The total water lost (transpiration) by the plant during this time was measured. After three weeks, the entire above-ground plant material was collected, dried at 65° C. for two days and weighed. The ratio of above-ground plant dry weight to plant water use is Water Use Efficiency (WUE). The percent difference of the results with the transgenic plants from results achieved with the wild-type control plants for WUE and above-ground dry weight (DW) for each of these three genes is given in Table 8.

For PpgBP-1 and PpVTP-1, the data are the average of a single assay of approximately 50 plants per genotype, 5 plants each of 10 independent lines. Data for plants comprising ScVTP-1 were from 19 individual transgenic and wild type plants. All three transgenic lines had significant increases in dry weight and water use efficiency. For each of the transgenes, the mean versus both of the controls for each parameter was increased, 8-30% for WUE, 17-68% for DW. The variation in phenotype from gene to gene may be explained by variation in the level of transgene expression and the site of transgene insertion.

TABLE 8

| BPS Gene name | Gene name in public domain | WUE increase(%) | DW increase(%) |
|---|---|---|---|
| PpGBP-1 | Sar1 small GTPase | 25 | 29 |
| PpVTP-1 | Rab Small GTPase | 8 | 17 |
| ScVTP-1 | V-SNARE protein | 30 | 68 |

Example 8

Detection of the GBP-1 Transgene in the Transgenic *Arabidopsis* Lines

One leaf from a wild type and a transgenic *Arabidopsis* plant was homogenized in 250 µl Hexadecyltrimethyl ammonium bromide (CTAB) buffer (2% CTAB, 1.4 M NaCl, 8mM EDTA and 20 mM Tris pH 8.0) and 1 µl β-mercaptoethanol. The samples were incubated at 60-65° C. for 30 minutes and 250 µl of Chloroform was then added to each sample. The samples were vortexed for 3 minutes and centrifuged for 5 minutes at 18,000×g. The supernatant was taken from each sample and 150 µl isopropanol was added. The samples were incubated at room temperature for 15 minutes, and centrifuged for 10 minutes at 18,000×g. Each pellet was washed with 70% ethanol, dried, and resuspended in 20 µl TE. 4 µl of above suspension was used in a 20 µl PCR reaction using Taq DNA polymerase (Roche Molecular Biochemicals) according to the manufacturer's instructions. Binary vector plasmid with each gene cloned in was used as positive control, and the wild type C24 genomic DNA was used as negative control in the PCR reactions. 10 µl PCR reaction was analyzed on 0.8% agarose/ethidium bromide gel. The PCR program used was as follows: 30 cycles of 1 minute at 94° C., 1 minute at 62° C. and 4 minutes at 70° C., followed by 10 minutes at 72° C.

The 5' primer was as follows: 5'GCTGACACGCCAAGC-CTCGCTAGTC3' (SEQ ID NO:18). The gene-specific primers and the size of the amplified bands (Gene Product Size) are listed below:

```
PpGBP-1:
Primer: RC587:
GCGTTAACTCGTCGCTCTTAAACACCGAGCTAAG (SEQ ID NO: 19)

Gene Product:
700 bp.
```

The transgene was successfully amplified from the T1 transgenic lines, but not from the wild type C24. This result indicates that the T1 transgenic plants contain at least one copy of the transgene. There was no indication of existence of either identical or very similar genes in the untransformed *Arabidopsis thaliana* control that could be amplified by this method.

Example 9

Detection of the PpgBP-1 Transgene mRNA in Transgenic *Arabidopsis* Lines

Transgene expression was detected using RT-PCR. Total RNA was isolated from stress-treated plants using a procedure adapted from (Verwoerd et al., 1989 NAR 17:2362). Leaf samples (50-100 mg) were collected and ground to a fine powder in liquid nitrogen. Ground tissue was resuspended in 500 µl of a 80° C., 1:1 mixture, of phenol to extraction buffer (100 mM LiCl, 100 mM Tris pH8, 10 mM EDTA, 1% SDS), followed by brief vortexing to mix. After the addition of 250 µl of chloroform, each sample was vortexed briefly. Samples were then centrifuged for 5 minutes at 12,000×g. The upper aqueous phase was removed to a fresh eppendorf tube. RNA was precipitated by adding ¹⁄₁₀th volume 3 M sodium acetate and 2 volumes 95% ethanol. Samples were mixed by inversion and placed on ice for 30 minutes. RNA was pelleted by centrifugation at 12,000×g for 10 minutes. The supernatant was removed and pellets briefly air-dried. RNA sample pellets were resuspended in 10 μl DEPC treated water. To remove contaminating DNA from the samples, each was treated with RNase-free DNase (Roche) according to the manufacturer's recommendations. cDNA was synthesized from total RNA using the 1st Strand cDNA synthesis kit (Boehringer Mannheim) following manufacturer's recommendations.

PCR amplification of a gene-specific fragment from the synthesized cDNA was performed using Taq DNA polymerase (Roche) and gene-specific primers (See Table 9 for primers) in the following reaction: 1×PCR buffer, 1.5 mM MgCl$_2$, 0.2 μM each primer, 0.2 μM dNTPs, 1 unit polymerase, 5 μl cDNA from synthesis reaction. Amplification was performed under the following conditions: Denaturation, 95° C., 1 minute; annealing, 62° C., 30 seconds; extension, 72° C., 1 minute, 35 cycles; extension, 72° C., 5 minutes; hold, 4° C., forever. PCR products were run on a 1% agarose gel, stained with ethidium bromide, and visualized under UV light using the Quantity-One gel documentation system (Bio-Rad). Expression of the transgene was detected in the T1 transgenic line. These results indicated that the transgene is expressed in the transgenic lines and strongly suggested that its gene product improved plant stress tolerance in the transgenic lines. In agreement with the previous statement, no expression of identical or very similar endogenous genes could be detected by this method. These results are in agreement with the data from Example 8.

TABLE 9

Primers used for the amplification of respective transgene mRNA in PCR using RNA isolated from transgenic *Arabidopsis thaliana* plants as template.

| Gene | 5' primer | 3' primer |
|---|---|---|
| PpGBP-1 | RC586: (SEQ ID NO:20) ATCCCGGGTCCGTAGATACCA AGGCTGGT | RC587: (SEQ ID NO:21) GCGTTAACTCGTCGCTCTTAA ACACCGAGCTAAG |

Example 10

Engineering Stress-Tolerant Soybean Plants by Over-Expressing the PpgBP-1, PpVTP-1, or ScVTP-1 Gene Seeds of soybean are surface sterilized with 70% ethanol for 4 minutes at room temperature with continuous shaking, followed by 20% (v/v) Clorox supplemented with 0.05% (v/v) Tween for 20 minutes with continuous shaking. Then, the seeds are rinsed 4 times with distilled water and placed on moistened sterile filter paper in a Petri dish at room temperature for 6 to 39 hours. The seed coats are peeled off, and cotyledons are detached from the embryo axis. The embryo axis is examined to make sure that the meristematic region is not damaged. The excised embryo axes are collected in a half-open sterile Petri dish and air-dried to a moisture content less than 20% (fresh weight) in a sealed Petri dish until further use.

*Agrobacterium tumefaciens* culture is prepared from a single colony in LB solid medium plus appropriate selection agents followed by growth of the single colony in liquid LB medium to an optical density at 600 nm of 0.8. Then, the bacteria culture is pelleted at 7000 rpm for 7 minutes at room temperature, and resuspended in MS (Murashige and Skoog, 1962) medium supplemented with 100 μM acetosyringone. Bacteria cultures are incubated in this pre-induction medium for 2 hours at room temperature before use. The axis of soybean zygotic seed embryos at approximately 15% moisture content are imbibed for 2 hours at room temperature with the pre-induced *Agrobacterium* suspension culture. The embryos are removed from the inhibition culture and are transferred to Petri dishes containing solid MS medium supplemented with 2% sucrose and incubated for 2 days in the dark at room temperature. Alternatively, the embryos are placed on top of moistened (liquid MS medium) sterile filter paper in a Petri dish and incubated under the same conditions described above. After this period, the embryos are transferred to either solid or liquid MS medium supplemented with 500 mg/L carbenicillin or 300 mg/L cefotaxime to kill the *Agrobacteria*. The liquid medium is used to moisten the sterile filter paper. The embryos are incubated during 4 weeks at 25° C., under 150 μmol m$^{-2}$ sec$^{-1}$ and 12 hours photoperiod. Once the seedlings produce roots, they are transferred to sterile metromix soil. The medium of the in vitro plants is washed off before transferring the plants to soil. The plants are kept under a plastic cover for 1 week to favor the acclimatization process. Then the plants are transferred to a growth room where they are incubated at 25° C., under 150 μmol m$^{-2}$ sec$^{-1}$ light intensity and 12 hours photoperiod for about 80 days.

The transgenic plants are screened for their improved growth and/or stress tolerance according to the screening methods described in Example 7, demonstrating that transgene expression confers stress tolerance and/or increased water use efficiency.

Example 11

Engineering Stress-Tolerant Rapeseed/Canola Plants by Overexpressing the PpgBP-1, PpVTP-1, or ScVTP-1 Gene Cotyledonary petioles of 4 day-old young seedlings are used as explants for tissue culture and transformed according to patent EPI 566443. The commercial cultivar Westar (Agriculture Canada) is the standard variety used for transformation, but other varieties can be used.

*Agrobacterium tumefaciens* GV3101:pMP90RK containing a binary vector is used for canola transformation. The standard binary vector used for transformation is pSUN (patent WO02/00900), but many different binary vector systems have been described for plant transformation (e.g. An, G. in *Agrobacterium* Protocols. Methods in Molecular Biology vol 44, pp 47-62, Gartland K M A and M R Davey eds. Humana Press, Totowa, N.J.). A plant gene expression cassette consists of at least two genes—a selection marker gene and a plant promoter regulating the transcription of the cDNA or genomic DNA of the trait gene. Various selection marker genes can be used including the *Arabidopsis* gene encoding a mutated acetohydroxy acid synthase (AHAS) enzyme (U.S. Pat. Nos. 5,767,366 and 6,225,105). Similarly, various promoters can be used to regulate the trait gene to provide constitutive, developmental, tissue or environmental regulation of gene transcription. In this example, the 34S promoter (GenBank Accession numbers M59930 and X16673) is used to provide constitutive expression of the trait gene.

Canola seeds are surface-sterilized in 70% ethanol for 2 min, incubated for 15 min in 55° C. warm tap water and then in 1.5% sodium hypochlorite for 10 min, followed by three rinses with sterilized distilled water. Seeds are then placed on MS medium without hormones, containing Gamborg B5 vitamins, 3% sucrose, and 0.8% Oxoidagar. Seeds are germinated at 24° C. for 4 days in low light (<50 μMol/m2s) at 16 hr light. The cotyledon petiole explants with the cotyledon attached are excised from the in vitro seedlings, and inoculated with *Agrobacterium* by dipping the cut end of the petiole explant into the bacterial suspension. The explants are then cultured for 3 days on MS medium including vitamins containing 3.75 mg/l BAP, 3% sucrose, 0.5 µl MES, pH 5.2, 0.5 mg/l GA3, 0.8% Oxoidagar at 24° C., 16 hr light. After three days of co-cultivation with *Agrobacterium*, the petiole explants are transferred to regeneration medium containing 3.75 mg/l BAP, 0.5 mg/l GA3, 0.5 g/l MES, pH 5.2, 300 mg/l timentin and selection agent until shoot regeneration. As soon as explants started to develop shoots they are transferred to shoot elongation medium (A6, containing full strength MS medium including vitamins, 2% sucrose, 0.5% Oxoidagar, 100 mg/l myo-inositol, 40 mg/l adenine sulfate, 0.5 g/l MES, pH 5.8, 0.0025 mg/l BAP, 0.1 mg/l IBA, 300 mg/l timentin and selection agent).

Samples from both in vitro and greenhouse material of the primary transgenic plants (T0) are analyzed by qPCR using TaqMan probes to confirm the presence of T-DNA and to determine the number of T-DNA integrations.

Seeds are produced from the primary transgenic plants by self-pollination. The second-generation plants are grown in greenhouse conditions and self-pollinated. The plants are analyzed by qPCR using TaqMan probes to confirm the presence of T-DNA and to determine the number of T-DNA integrations. Homozygous transgenic, heterozygous transgenic and azygous (null transgenic) plants are compared for their growth characteristics and yield.

Example 12

Engineering Stress-Tolerant Corn Plants by Overexpressing the PpgBP-1, PpVTP-1, or ScVTP-1 Gene

*Agrobacterium* cells harboring the genes and the maize ahas gene on the same plasmid are grown in YP medium supplemented with appropriate antibiotics for 1-3 days. A loop of *Agrobacterium* cells is collected and suspended in 2 ml M-LS-002 medium (LS-inf) and the tube containing *Agrobacterium* cells is kept on a shaker for 1-3 hrs at 1,200 rpm.

Corncobs [genotype J553x(HIIIAxA188)] are harvested at 7-12 days after pollination. The cobs are sterilized in 20% Clorox solution for 15 min followed by thorough rinse with sterile water. Immature embryos with size 0.8-2.0 mm are dissected into the tube containing *Agrobacterium* cells in LS-inf solution.

Agro-infection is carried out by keeping the tube horizontally in the laminar hood at room temperature for 30 min. Mixture of the agro infection is poured on to a plate containing the co-cultivation medium (M-LS-011). After the liquid agro-solution is piped out, the embryos are plated on the co-cultivation medium with schutellum side up and cultured in the dark at 22 C. for 2-4 days.

Embryos are transferred to M-MS-101 medium without selection. 7-10 days later, embryos are transferred to M-LS-401medium containing 0.75 µM imazethapyr and grown for 4 weeks to select transformed callus cells.

Plant regeneration is initiated by transferring resistant calli to M-LS-504 medium supplemented with 0.75 µM imazethapyr and grown under light at 26° C. for two to three weeks. Regenerated shoots are then transferred to rooting box with M-MS-607 medium (0.5 µM imazethapyr).

Plantlets with roots are transferred to potting mixture and grown in a growth chamber for a week, then transplanted to larger pots and maintained in greenhouse till maturity.

Example 13

Engineering Stress-Tolerant Wheat Plants by Overexpressing PpgBP-1, PpVTP-1, or ScVTP-1 Gene Transformation of wheat with the gene of interest is performed with the method described by Ishida et al., 1996, Nature Biotech. 14745-50. Immature embryos are co-cultivated with *Agrobacterium tumefaciens* that carry "super binary" vectors, and transgenic plants are recovered through organogenesis. This procedure provides a transformation efficiency between 2.5% and 20%. The transgenic plants are screened for their improved growth and/or stress tolerance according to the screening methods described in Example 7, demonstrating that transgene expression confers stress tolerance and/or increased water use efficiency.

Example 14

Identification of Homologous and Heterologous Genes

Gene sequences can be used to identify homologous or heterologous genes from cDNA or genomic libraries. Homologous genes (e.g. full-length cDNA clones) can be isolated via nucleic acid hybridization using for example cDNA libraries. Depending on the abundance of the gene of interest, 100,000 up to 1,000,000 recombinant bacteriophages are plated and transferred to nylon membranes. After denaturation with alkali, DNA is immobilized on the membrane by, e.g., UV cross linking. Hybridization is carried out at high stringency conditions. In aqueous solution, hybridization and washing is performed at an ionic strength of 1 M NaCl and a temperature of 68° C. Hybridization probes are generated by, e.g., radioactive ($^{32}$P) nick transcription labeling (High Prime, Roche, Mannheim, Germany). Signals are detected by autoradiography.

Partially homologous or heterologous genes that are related but not identical can be identified in a manner analogous to the above-described procedure using low stringency hybridization and washing conditions. For aqueous hybridization, the ionic strength is normally kept at 1 M NaCl while the temperature is progressively lowered from 68 to 42° C.

Isolation of gene sequences with homologies (or sequence identity/similarity) only in a distinct domain of (for example 10-20 amino acids) can be carried out by using synthetic radio labeled oligonucleotide probes. Radiolabeled oligonucleotides are prepared by phosphorylation of the 5-prime end of two complementary oligonucleotides with T4 polynucleotide kinase. The complementary oligonucleotides are annealed and ligated to form concatemers. The double stranded concatemers are then radiolabeled by, for example, nick transcription. Hybridization is normally performed at low stringency conditions using high oligonucleotide concentrations.

Oligonucleotide Hybridization Solution
6×SSC
0.01 M sodium phosphate
1 mM EDTA (pH 8)
0.5% SDS
100 µg/ml denatured salmon sperm DNA
0.1% nonfat dried milk During hybridization, the temperature is lowered stepwise to 5-10° C. below the estimated oligonucleotide $T_m$, or down to room temperature, followed by washing steps and autoradiography. Washing is performed with low stringency, such as 3 washing steps using 4×SSC. Further details are described by Sambrook, J. et al., 1989, "Molecular Cloning: A Laboratory Manual", Cold Spring Harbor Laboratory Press or Ausubel, F. M. et al., 1994, "Current Protocols in Molecular Biology", John Wiley & Sons.

Example 15

Identification of Homologous Genes by Screening Expression Libraries with Antibodies c-DNA clones can be used to produce recombinant protein for example in *E. coli* (e.g. Qiagen QIAexpress pQE system). Recombinant proteins are then normally affinity purified via Ni-NTA affinity chromatography (Qiagen). Recombinant proteins are then used to produce specific antibodies for example by using standard techniques for rabbit immunization. Antibodies are affinity purified using a Ni-NTA column saturated with the recombinant antigen as described by Gu et al., 1994, BioTechniques 17:257-262. The antibody can be used to screen expression cDNA libraries to identify homologous or heterologous genes via an immunological screening (Sambrook, J. et al., 1989, "Molecular Cloning: A Laboratory Manual", Cold Spring Harbor Laboratory Press or Ausubel, F. M. et al., 1994, "Current Protocols in Molecular Biology", John Wiley & Sons).

Example 16

In vivo Mutagenesis

In vivo mutagenesis of microorganisms can be performed by passage of plasmid (or other vector) DNA through *E. coli* or other microorganisms (e.g. *Bacillus* spp. or yeasts such as *Saccharomyces cerevisiae*) which are impaired in their capabilities to maintain the integrity of their genetic information. Typical mutator strains have mutations in the genes for the DNA repair system (e.g., mutHLS, mutD, mutT, etc.; for reference, see Rupp, W. D., 1996, DNA repair mechanisms, in: *Escherichia coli* and *Salmonella*, p. 2277-2294, ASM: Washington.) Such strains are well known to those skilled in the art. The use of such strains is illustrated, for example, in Greener, A. and Callahan, M., 1994, Strategies 7:32-34. Transfer of mutated DNA molecules into plants is preferably done after selection and testing in microorganisms. Transgenic plants are generated according to various examples within the exemplification of this document.

Example 17

In vitro Analysis of the Function of *Physcomitrella* and *Saccharomyces* Genes in Transgenic Organisms The determination of activities and kinetic parameters of enzymes is well established in the art. Experiments to determine the activity of any given altered enzyme must be tailored to the specific activity of the wild-type enzyme, which is well within the ability of one skilled in the art. Overviews about enzymes in general, as well as specific details concerning structure, kinetics, principles, methods, applications, and examples for the determination of many enzyme activities may be found, for example, in the following references: Dixon, M., and Webb, E. C., 1979, Enzymes. Longmans: London; Fersht, 1985, Enzyme Structure and Mechanism. Freeman: New York; Walsh, 1979, Enzymatic Reaction Mechanisms. Freeman: San Francisco; Price, N. C., Stevens, L., 1982, Fundamentals of Enzymology. Oxford Univ. Press: Oxford; Boyer, P. D., ed., 1983, The Enzymes, $3^{rd}$ ed. Academic Press: New York; Bisswanger, H., 1994, Enzymkinetik, $2^{nd}$ ed. VCH: Weinheim (ISBN 3527300325); Bergmeyer, H. U., Bergmeyer, J., Graβl, M., eds., 1983-1986, Methods of Enzymatic Analysis, $3^{rd}$ ed., vol. I-XII, Verlag Chemie: Weinheim; and Ullmann's Encyclopedia of Industrial Chemistry, 1987, vol. A9, Enzymes. VCH: Weinheim, p. 352-363.

The activity of proteins which bind to DNA can be measured by several well-established methods, such as DNA band-shift assays (also called gel retardation assays). The effect of such proteins on the expression of other molecules can be measured using reporter gene assays (such as that described in Kolmar, H. et al., 1995, EMBO J. 14: 3895-3904 and references cited therein). Reporter gene test systems are well known and established for applications in both pro- and eukaryotic cells, using enzymes such as β-galactosidase, green fluorescent protein, and several others.

The determination of activity of membrane-transport proteins can be performed according to techniques such as those described in Gennis, R. B., 1989, Pores, Channels and Transporters, in Biomembranes, Molecular Structure and Function, pp. 85-137, 199-234 and 270-322, Springer: Heidelberg.

Example 18

Purification of the Desired Product from Transformed Organisms

Recovery of the desired product from plant material (i.e., *Physcomitrella patens* or *Arabidopsis thaliana*, fungi, algae, ciliates, *C. glutamicum* cells, or other bacterial cells transformed with the nucleic acid sequences described herein, or the supernatant of the above-described cultures can be performed by various methods well known in the art. If the desired product is not secreted from the cells, the cells can be harvested from the culture by low-speed centrifugation, and the cells can be lysed by standard techniques, such as mechanical force or sonification. Organs of plants can be separated mechanically from other tissue or organs. Following homogenization, cellular debris is removed by centrifugation, and the supernatant fraction containing the soluble proteins is retained for further purification of the desired compound. If the product is secreted from desired cells, then the cells are removed from the culture by low-speed centrifugation, and the supernate fraction is retained for further purification.

The supernatant fraction from either purification method is subjected to chromatography with a suitable resin, in which the desired molecule is either retained on a chromatography resin while many of the impurities in the sample are not, or where the impurities are retained by the resin while the sample is not. Such chromatography steps may be repeated as necessary, using the same or different chromatography resins. One skilled in the art would be well-versed in the selection of appropriate chromatography resins and in their most efficacious application for a particular molecule to be purified. The purified product may be concentrated by filtration or ultrafiltration, and stored at a temperature at which the stability of the product is maximized.

There is a wide array of purification methods known to the art and the preceding method of purification is not meant to be limiting. Such purification techniques are described, for example, in Bailey, J. E. & Ollis, 1986, D. F. Biochemical Engineering Fundamentals, McGraw-Hill: New York. Additionally, the identity and purity of the isolated compounds may be assessed by techniques standard in the art. These include high-performance liquid chromatography (HPLC), spectroscopic methods, staining methods, thin layer chromatography, NIRS, enzymatic assay, or microbiologically. Such analysis methods are reviewed in: Patek et al., 1994, Appl. Environ. Microbiol. 60:133-140; Malakhova et al., 1996, Biotelhnologiya 11:27-32; and Schmidt et al., 1998, Bioprocess Engineer. 19:67-70; Ulmann's Encyclopedia of Industrial Chemistry, 1996, vol. A27, VCH: Weinheim, p. 89-90, p. 521-540, p. 540-547, p. 559-566, 575-581, and p. 581-587; Michal, G., 1999, Biochemical Pathways: An Atlas of Biochemistry and Molecular Biology, John Wiley and Sons; Fallon, A. et al., 1987, Applications of HPLC in Biochemistry in: Laboratory Techniques in Biochemistry and Molecular Biology, vol. 17.

Example 19

Greenhouse Screening for Stress Tolerant Plants

Seeds from transgenic corn plants were planted into 4" square paper pots preloaded into trays. The pots were filled with Metro Mix (Metro Mix 360) mixed with gypsum and osomocote. The seeds were sown, well watered and allowed to grow under normal greenhouse conditions (photoperiod: 14 hrs, temperature: 82° F. day, 65° F. night). The plants were sampled for detection of the transgenic genes 7 days post emergence.

The plants were transplanted into Classic 1200 pots containing 4 Kg of Metro Mix 360. Three transgenic and three null sibling plants were planted into the Metro Mix, equally spaced, with the same genotyped plants along one side of the pot. Null sibling plant is a plant segregated from its transgenic parent plant. It does not contain the plasmid. Four replicate pots per line were transplanted. An additional one kg of Metro Mix was added to the pots to cover the paper pots and fill in the areas between the plants.

The plants continued to grow for 19 days after transplanting under either 50% field capacity or 30% field capacity by adding water to the PVC pipe every Monday, Wednesday, and Friday for 16 days. Field capacity is defined as the percentage of the soil water content in contrast to the maximum soil water content. On the last day of the assay, the plants were harvested. The same genotype plants from one pot were grouped together, resulting in four replicates per genotype per line, totaling eight samples per line (four transgenic, four null siblings). Fresh weight was collected for each sample. Each sample allowed to dry in an oven at 65° C. for six days. The dry weights were then collected.

All three genes showed increased biomass under drought condition. Five PpgBP-1 events showed biomass increase in the range of 7.3%-16.3% (Table 10). PpVTP-1 plants showed biomass increase in the range of 5.9-16.4% under 50% water field capacity (Table 11). Transgenic plant containing ScVTP-1 showed biomass increase in the range of 5.3-6.1% under 30% water field capacity (Table 12).

TABLE 10

Competition assay of PpGBP-1 transgenic plants under 50% water field capacity.

| Event | Number of Values | | Average | | |
| --- | --- | --- | --- | --- | --- |
| | Null | Transgenic | Null | Transgenic | % Change |
| ERG067M0008 | 12 | 12 | 46.0 | 49.3 | 7.3 |
| ERG067M0001 | 13 | 11 | 53.7 | 57.8 | 7.6 |
| ERG067M0006 | 12 | 12 | 45.9 | 49.4 | 7.7 |
| ERG067M0020 | 12 | 12 | 46.4 | 51.4 | 10.7 |
| ERG067M0013 | 4 | 4 | 51.5 | 60.0 | 16.3 |

TABLE 11

Competition assay of PpVTP-1 transgenic plants under 50% water field capacity.

| Event | Number of Values | | Average | | |
| --- | --- | --- | --- | --- | --- |
| | Null | Transgenic | Null | Transgenic | % Change |
| J553/ERG072M0001 | 11 | 13 | 61.0 | 64.7 | 5.9 |
| J553/ERG072M0005 | 13 | 13 | 64.7 | 69.2 | 7.0 |
| J553/ERG072M0007 | 12 | 12 | 66.8 | 72.5 | 8.6 |
| J553/ERG072M0008 | 12 | 12 | 62.1 | 68.4 | 10.0 |
| J553/ERG072M0010 | 12 | 12 | 59.6 | 66.9 | 12.1 |
| J553/ERG072M0011 | 12 | 11 | 59.8 | 69.6 | 16.4 |

TABLE 12

Competition assay of ScVTP-1 transgenic plants under 30% water field capacity.

| Event | Number of Values | | Average | | |
| --- | --- | --- | --- | --- | --- |
| | Null | Transgenic | Null | Transgenic | % Change |
| YMR197CM0014 | 12 | 12 | 56.9 | 59.9 | 5.3 |
| YMR197CM0001 | 8 | 8 | 66.8 | 70.4 | 5.3 |
| YMR197CM0007 | 12 | 12 | 77.4 | 82.0 | 5.9 |
| YMR197CM0011 | 8 | 8 | 65.2 | 69.2 | 6.1 |

Example 20

Field Screening for Stress Tolerant Plants

Transgenic corn plants were grown under rain-free field conditions with drought stress treatments imposed by manipulating irrigation volumes. All plants received optimum irrigation for 4 weeks after planting. After that time through harvest, 3 irrigation regimes were imposed. A 100% treatment condition is defined as maintaining an optimum irrigation volume. A moderate drought condition is defined as consisting of 80% of the optimum volume and a severe drought condition is defined as consisting of 29% of the optimum volume. A single row of each independent event was planted in each irrigation treatment area. Transgenic plants were compared to their null segregants within the row. Measurement of plant height was performed on the plants grown under the severe drought condition. Measurement of plant grain yield was performed on plants grown under either moderate drought or optimum irrigation conditions.

PpgBP-1 and PpVTP-1 transgenic plants showed increase in grain yield under well-watered and drought conditions. Under well-watered (100%) irrigation condition in the field, PpVTP-1 plants showed yield increase in the range of 12%-115% (Table 13). Under moderate drought (80% irrigation) condition in the field, the PpVTP-1 plants showed yield increase in the range of 21%-115% (Table 14).

TABLE 13

Grain weight/per plant assay of PpVTP-1 transgenic plants under optimum (100%) irrigation condition in the field.

| Event Name | Mean Grain Weight (g per plant) Null | Mean Grain Weight (g per plant) Transgenic | Standard Error Null | Standard Error Transgenic | Number of Plants Null | Number of Plants Transgenic | % Change (Transgenic/Null) |
|---|---|---|---|---|---|---|---|
| 106921 | 4.8 | 10.4 | 2.1 | 2.8 | 10 | 32 | 115 |
| 102051 | 12.1 | 24.8 | 3.7 | 6.2 | 21 | 21 | 105 |
| 106831 | 15.4 | 27.4 | 4.5 | 4.6 | 20 | 17 | 78 |
| 1011131 | 6.9 | 11.5 | 2.6 | 2.5 | 20 | 20 | 67 |
| 106971 | 9.7 | 11.0 | 3.2 | 3.3 | 21 | 21 | 13 |
| 1010651 | 52.3 | 58.8 | 7.6 | 5.9 | 19 | 23 | 12 |

TABLE 14

Grain weight/per plant assay of PpVTP-1 under moderate drought (80% irrigation) condition in the field.

| Event Name | Mean Grain Weight (g per plant) Null | Mean Grain Weight (g per plant) Transgenic | Standard Error Null | Standard Error Transgenic | Number of Plants Null | Number of Plants Transgenic | % Change (Transgenic/Null) |
|---|---|---|---|---|---|---|---|
| 101631 | 0.4 | 4.5 | 0.3 | 1.9 | 20 | 22 | 1156 |
| 1010651 | 0.2 | 2.2 | 0.2 | 2.2 | 24 | 19 | 1021 |
| 106831 | 0.2 | 1.0 | 0.2 | 0.6 | 20 | 21 | 393 |
| 101701 | 2.6 | 8.5 | 1.1 | 2.8 | 42 | 42 | 230 |
| 106921 | 0.0 | 0.1 | 0.0 | 0.1 | 12 | 31 | 109 |
| 1011131 | 6.1 | 11.9 | 3.4 | 3.1 | 15 | 27 | 93 |
| 102051 | 0.9 | 1.7 | 0.4 | 0.9 | 23 | 18 | 82 |
| 1011121 | 0.1 | 0.1 | 0.1 | 0.1 | 23 | 19 | 21 |

Under optimum (100%) irrigation condition in the field, PpgBP-1 transgenic plants showed increase in yield in the range of 27-249% (Table 15). Under moderate drought (80% irrigation) condition in the field, the yield increase is in the range of 50-175% (Table 16).

TABLE 15

Grain weight/per plant assay of PpGBP-1 transgenic plants under optimum (100%) irrigation condition in the field.

| Event Name | Mean Grain Weight (g per plant) Null | Mean Grain Weight (g per plant) Transgenic | Standard Error Null | Standard Error Transgenic | Number of Plants Null | Number of Plants Transgenic | % Change (Transgenic/Null) |
|---|---|---|---|---|---|---|---|
| 107551 | 3.9 | 13.6 | 1.8 | 4.0 | 15 | 27 | 249 |
| 1011131 | 6.9 | 11.5 | 2.6 | 2.5 | 20 | 20 | 67 |
| 107631 | 28.4 | 42.5 | 5.0 | 11.4 | 29 | 12 | 50 |
| 1019171 | 36.5 | 48.3 | 7.6 | 6.4 | 19 | 22 | 32 |
| 107681 | 40.6 | 51.8 | 11.3 | 6.7 | 13 | 29 | 27 |

TABLE 16

Grain weight/per plant assay of PpGBP-1 transgenic plants under moderate drought (80% irrigation) condition in the field.

| Event Name | Mean Grain Weight (g per plant) Null | Mean Grain Weight (g per plant) Transgenic | Standard Error Null | Standard Error Transgenic | Number of Plants Null | Number of Plants Transgenic | % Change (Transgenic/Null) |
|---|---|---|---|---|---|---|---|
| 107631 | 0.3 | 0.9 | 0.2 | 0.8 | 24 | 18 | 175 |
| 1011711 | 10.0 | 16.5 | 4.0 | 5.0 | 20 | 19 | 64 |
| 107551 | 1.0 | 1.6 | 0.6 | 0.8 | 21 | 21 | 50 |

We claim:

1. An isolated polynucleotide selected from the group consisting of: a) a polynucleotide comprising nucleotides 1 to 642 of SEQ ID NO: 1; and b) a polynucleotide encoding a polypeptide comprising amino acids 1 to 204 of SEQ ID NO:2.

2. A recombinant expression vector comprising an isolated polynucleotide selected from the group consisting of:
   a) a polynucleotide comprising nucleotides 1 to 642 of SEQ ID NO:1; and
   b) a polynucleotide encoding a polypeptide comprising amino acids 1 to 204 of SEQ ID NO:2.

3. A transgenic plant transformed with a polynucleotide selected from the group consisting of: a) a polynucleotide sequence comprising nucleotides 1 to 642 of SEQ ID NO:1; and b) a polynucleotide sequence encoding a polypeptide comprising amino acids 1 to 204 of SEQ ID NO:2; wherein expression of the polynucleotide in the plant results in increased tolerance to drought as compared to a wild type variety of the plant.

4. The transgenic plant of claim 3, further defined as a monocot.

5. The transgenic plant of claim 3, further defined as a dicot.

6. A part of the transgenic plant of claim 3, wherein said part is selected from the group consisting of, a plant cell, and a seed, and wherein said part comprises the polynucleotide.

7. The transgenic plant of claim 3, wherein expression of the polynucleotide in the plant results in increased growth of the plant under water-limited conditions.

8. The transgenic plant of claim 7, wherein the increased growth under water-limited conditions is due to the plant having increased Water Use Efficiency (WUE).

9. The transgenic plant of claim 8, wherein the increased WUE is due to the plant having increased dry weight.

10. A part of the transgenic plant of claim 7, wherein said part is selected from the group consisting of, a plant cell, and a seed, and wherein said part comprises the polynucleotide.

11. A part of the transgenic plant of claim 8, wherein said part is selected from the group consisting of, a plant cell, and a seed, and wherein said part comprises the polynucleotide.

12. A part of the transgenic plant of claim 9, wherein said part is selected from the group consisting of, a plant cell, and a seed, and wherein said part comprises the polynucleotide.

13. The transgenic plant of claim 3, wherein the plant is selected from the group consisting of maize, wheat, rye, oat, triticale, rice, barley, soybean, peanut, cotton, rapeseed, canola, manihot, pepper, sunflower, tagetes, solanaceous plants, potato, tobacco, eggplant, tomato, *Vicia* species, pea, alfalfa, coffee, cacao, tea, *Salix* species, oil palm, coconut, perennial grass, and a forage crop.

14. A method of producing a drought-tolerant transgenic plant, wherein the method comprises the steps of: a) transforming a plant cell with an expression vector comprising a polynucleotide selected from the group consisting of: i) a polynucleotide sequence comprising nucleotides 1 to 642 of SEQ ID NO:1; and ii) a polynucleotide sequence encoding a polypeptide comprising amino acids 1 to 204 of SEQ ID NO:2; and b) generating a transgenic plant from the transformed plant cell, wherein the transgenic plant expressing said polynucleotide is drought tolerant.

15. The method of claim 14, wherein the plant is a monocot.

16. The method of claim 14, wherein the plant is a dicot.

17. The method of claim 14, wherein the plant is selected from the group consisting of maize, wheat, rye, oat, triticale, rice, barley, soybean, peanut, cotton, rapeseed, canola, manihot, pepper, sunflower, tagetes, solanaceous plants, potato, tobacco, eggplant, tomato, *Vicia* species, pea, alfalfa, coffee, cacao, tea, *Salix* species, oil palm, coconut, perennial grass, and a forage crop.

18. The transgenic plant of claim 13, which is maize.

19. The transgenic plant of claim 13, which is soybean.

20. The transgenic plant of claim 13, which is cotton.

21. The transgenic plant of claim 13, which is rapeseed or canola.

22. The isolated polynucleotide of claim 1, which encodes the polypeptide comprising amino acids 1 to 204 of SEQ ID NO:2.

23. The isolated polynucleotide of claim 1, which comprises nucleotides 1 to 642 of SEQ ID NO:1.

24. The transgenic plant of claim 6, which is a seed.

25. The seed of claim 24, which is true breeding for the polynucleotide encoding the polypeptide comprising amino acids 1 to 204 of SEQ ID NO:2.

26. The seed of claim 24, which is true breeding for the polynucleotide comprising nucleotides 1 to 642 of SEQ ID NO:1.

* * * * *

SEQUENCE LISTING

<160> NUMBER OF SEQ ID NOS: 33

<210> SEQ ID NO 1
<211> LENGTH: 642
<212> TYPE: DNA
<213> ORGANISM: Physcomitrella patens

<400> SEQUENCE: 1

```
cccagaaggc cgatccgaaa gaaaggcacc atgaatcccg aatatgatta ccttttcaag      60
ctgttgctga tcggagactc cggtgttgga aagagttgcc ttctgctacg atttgcagac     120
gactcgtacc tggagagcta catcagcaca atcggtgtgg actttaaaat acgtacggtg     180
gagctggacg ggaagaccat caagttgcag atttgggata ctgctggtca ggagaggttc     240
cggaccatca aagcagcta ctatcgtgga gcgcacggga tcattgttgt gtacgacgtg      300
acagaccagg agagcttcaa caacgtgaag caatggttga gtgagatcga ccggtacgcg     360
agcgagaacg tgaacaagct gctggtgggc aacaagtcag atctggcgtc gaagaaggtg     420
gtggattatg caactgcaaa ggcatttgcg gacgagattg ggattccgtt tttggagacg     480
agtgcgaaga atgctacgaa cgtggagcag gcgtttatga caatggcagc ggagatcaag     540
aacaggatgg cgagtcagcc cgcgttgagc agcacaagca ggccgaacaa tgtgacgaac     600
ctgcgaggac aggctattcc gcagaagagt gggtgctgct ca                        642
```

<210> SEQ ID NO 2
<211> LENGTH: 204
<212> TYPE: PRT
<213> ORGANISM: Physcomitrella patens

<400> SEQUENCE: 2

```
Met Asn Pro Glu Tyr Asp Tyr Leu Phe Lys Leu Leu Ile Gly Asp
1               5                   10                  15

Ser Gly Val Gly Lys Ser Cys Leu Leu Leu Arg Phe Ala Asp Asp Ser
            20                  25                  30

Tyr Leu Glu Ser Tyr Ile Ser Thr Ile Gly Val Asp Phe Lys Ile Arg
        35                  40                  45

Thr Val Glu Leu Asp Gly Lys Thr Ile Lys Leu Gln Ile Trp Asp Thr
    50                  55                  60

Ala Gly Gln Glu Arg Phe Arg Thr Ile Thr Ser Ser Tyr Tyr Arg Gly
65                  70                  75                  80

Ala His Gly Ile Ile Val Val Tyr Asp Val Thr Asp Gln Glu Ser Phe
                85                  90                  95

Asn Asn Val Lys Gln Trp Leu Ser Glu Ile Asp Arg Tyr Ala Ser Glu
            100                 105                 110

Asn Val Asn Lys Leu Leu Val Gly Asn Lys Ser Asp Leu Ala Ser Lys
        115                 120                 125

Lys Val Val Asp Tyr Ala Thr Ala Lys Ala Phe Ala Asp Glu Ile Gly
    130                 135                 140

Ile Pro Phe Leu Glu Thr Ser Ala Lys Asn Ala Thr Asn Val Glu Gln
145                 150                 155                 160

Ala Phe Met Thr Met Ala Ala Glu Ile Lys Asn Arg Met Ala Ser Gln
                165                 170                 175

Pro Ala Leu Ser Ser Thr Ser Arg Pro Asn Asn Val Thr Asn Leu Arg
            180                 185                 190

Gly Gln Ala Ile Pro Gln Lys Ser Gly Cys Cys Ser
```

<210> SEQ ID NO 3
<211> LENGTH: 606
<212> TYPE: DNA
<213> ORGANISM: Physcomitrella patens

<400> SEQUENCE: 3

```
cccgggtccg tagataccaa ggctggtacc atgtttcttg tagattggtt ttacggcttt      60
cttgcgagca tagggctgtg gcagaaggag gccaaaatcc tgtttctggg tctcgacaat     120
gctggcaaga ctactcttct gcacatgctc aaggatgaga aactgggggca acatcaacca    180
acgcagtatc caacgtcaga ggagttgagt atcaacagag tgaagttcaa agcattcgat     240
ctgggtggcc acacaatcgc tcgacgcgtg tggagggact actatgctaa ggtggatgct     300
atagtgtatc tcgtcgacgc agtagacagg gagagatttg ctgagtcaaa gaaagagctc     360
gattctcttc tctccgacga ttctctgtcc caagttcctg tgctcgtcct gggaaacaag     420
attgatatcc cgtacgcttc ttctgaagac gagttgcggt tcacacttgg gttgaccatg     480
accactggta aaggaacggt gaaccctggga gatagcaaca ttcggcccat tgaggttttc    540
atgtgcagta ttgtgcgcaa aatggggtac ggtgaaggtt tcaagtggat gacccagtac    600
atcaag                                                                606
```

<210> SEQ ID NO 4
<211> LENGTH: 192
<212> TYPE: PRT
<213> ORGANISM: Physcomitrella patens

<400> SEQUENCE: 4

```
Met Phe Leu Val Asp Trp Phe Tyr Gly Phe Leu Ala Ser Ile Gly Leu
  1               5                  10                  15

Trp Gln Lys Glu Ala Lys Ile Leu Phe Leu Gly Leu Asp Asn Ala Gly
             20                  25                  30

Lys Thr Thr Leu Leu His Met Leu Lys Asp Glu Lys Leu Gly Gln His
         35                  40                  45

Gln Pro Thr Gln Tyr Pro Thr Ser Glu Glu Leu Ser Ile Asn Arg Val
     50                  55                  60

Lys Phe Lys Ala Phe Asp Leu Gly Gly His Thr Ile Ala Arg Arg Val
 65                  70                  75                  80

Trp Arg Asp Tyr Tyr Ala Lys Val Asp Ala Ile Val Tyr Leu Val Asp
                 85                  90                  95

Ala Val Asp Arg Glu Arg Phe Ala Glu Ser Lys Lys Glu Leu Asp Ser
            100                 105                 110

Leu Leu Ser Asp Asp Ser Leu Ser Gln Val Pro Val Leu Val Leu Gly
        115                 120                 125

Asn Lys Ile Asp Ile Pro Tyr Ala Ser Ser Glu Asp Glu Leu Arg Phe
    130                 135                 140

Thr Leu Gly Leu Thr Met Thr Thr Gly Lys Gly Thr Val Asn Leu Gly
145                 150                 155                 160

Asp Ser Asn Ile Arg Pro Ile Glu Val Phe Met Cys Ser Ile Val Arg
                165                 170                 175

Lys Met Gly Tyr Gly Glu Gly Phe Lys Trp Met Thr Gln Tyr Ile Lys
            180                 185                 190
```

<210> SEQ ID NO 5
<211> LENGTH: 654

<212> TYPE: DNA
<213> ORGANISM: Saccharomyces cerevisiae

<400> SEQUENCE: 5

```
atgagttccc tattaatatc atacgaatct gacttcaaaa caaccttaga acaagccaaa      60
gcgagcttag cagaggcccc ctcacaaccg ttatcacaga gaaatactac actgaagcac     120
gtagaacagc aacaagatga gttgtttgac ctgctagatc agatggatgt agaagttaat     180
aacagcatag gcgatgcctc agaacgtgct acgtacaagg cgaagttaag agaatggaag     240
aagactatac agagcgatat caaacgacca ctgcaatcct tagtagactc aggcgatcgt     300
gatagacttt ttggagatct taacgcatct aatattgacg atgaccaaag gcaacagttg     360
ttgagcaacc atgcaatctt acagaaatcg ggagatagac taaaagatgc cagtagaata     420
gcaaatgaaa ctgaaggaat agggtcacaa ataatgatgg atttaaggtc acagagagaa     480
actttggaaa atgcaagaca gaccttgttt caagcggatt catatgtgga taaaagtata     540
aagacactaa aaacaatgac tagaaggcta gttgctaata aattcataag ctatgccatt     600
atcgcagtcc ttatattatt gattttgcta gttttgttct caaagtttaa ataa           654
```

<210> SEQ ID NO 6
<211> LENGTH: 217
<212> TYPE: PRT
<213> ORGANISM: Saccharomyces cerevisiae

<400> SEQUENCE: 6

```
Met Ser Ser Leu Leu Ile Ser Tyr Glu Ser Asp Phe Lys Thr Thr Leu
1               5                   10                  15

Glu Gln Ala Lys Ala Ser Leu Ala Glu Ala Pro Ser Gln Pro Leu Ser
            20                  25                  30

Gln Arg Asn Thr Thr Leu Lys His Val Glu Gln Gln Asp Glu Leu
        35                  40                  45

Phe Asp Leu Leu Asp Gln Met Asp Val Glu Val Asn Asn Ser Ile Gly
    50                  55                  60

Asp Ala Ser Glu Arg Ala Thr Tyr Lys Ala Lys Leu Arg Glu Trp Lys
65                  70                  75                  80

Lys Thr Ile Gln Ser Asp Ile Lys Arg Pro Leu Gln Ser Leu Val Asp
                85                  90                  95

Ser Gly Asp Arg Asp Arg Leu Phe Gly Asp Leu Asn Ala Ser Asn Ile
            100                 105                 110

Asp Asp Asp Gln Arg Gln Gln Leu Leu Ser Asn His Ala Ile Leu Gln
        115                 120                 125

Lys Ser Gly Asp Arg Leu Lys Asp Ala Ser Arg Ile Ala Asn Glu Thr
    130                 135                 140

Glu Gly Ile Gly Ser Gln Ile Met Met Asp Leu Arg Ser Gln Arg Glu
145                 150                 155                 160

Thr Leu Glu Asn Ala Arg Gln Thr Leu Phe Gln Ala Asp Ser Tyr Val
                165                 170                 175

Asp Lys Ser Ile Lys Thr Leu Lys Thr Met Thr Arg Arg Leu Val Ala
            180                 185                 190

Asn Lys Phe Ile Ser Tyr Ala Ile Ile Ala Val Leu Ile Leu Leu Ile
        195                 200                 205

Leu Leu Val Leu Phe Ser Lys Phe Lys
    210                 215
```

<210> SEQ ID NO 7

```
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Description of Artificial Sequence: Synthetic
      primer

<400> SEQUENCE: 7
caggaaacag ctatgacc                                                   18

<210> SEQ ID NO 8
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: Description of Artificial Sequence: Synthetic
      primer

<400> SEQUENCE: 8
ctaaagggaa caaaagctg                                                  19

<210> SEQ ID NO 9
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Description of Artificial Sequence: Synthetic
      primer

<400> SEQUENCE: 9
tgtaaaacga cggccagt                                                   18

<210> SEQ ID NO 10
<211> LENGTH: 45
<212> TYPE: DNA
<213> ORGANISM: Artificial Sequence
<220> FEATURE:
<221> NAME/KEY: misc_feature
<222> LOCATION: (1)..(45)
<223> OTHER INFORMATION: Description of Artificial Sequence: Synthetic
      oligonucleotide

<400> SEQUENCE: 10
ggaattccag ctgaccacca tgagttccct attaatatca tacga                     45

<210> SEQ ID NO 11
<211> LENGTH: 45
<212> TYPE: DNA
<213> ORGANISM: Artificial Sequence
<220> FEATURE:
<221> NAME/KEY: misc_feature
<222> LOCATION: (1)..(45)
<223> OTHER INFORMATION: Description of Artificial Sequence: Synthetic
      oligonucleotide

<400> SEQUENCE: 11
gatccccggg aattgccatg ctattgattg tttgttccac ggact                     45

<210> SEQ ID NO 12
<211> LENGTH: 25
<212> TYPE: DNA
<213> ORGANISM: Artificial Sequence
<220> FEATURE:
```

```
<221> NAME/KEY: misc_feature
<222> LOCATION: (1)..(25)
<223> OTHER INFORMATION: Description of Artificial Sequence: Synthetic
      primer

<400> SEQUENCE: 12
tgccagcatt gtcgagaccc agaaa                                           25

<210> SEQ ID NO 13
<211> LENGTH: 29
<212> TYPE: DNA
<213> ORGANISM: Artificial Sequence
<220> FEATURE:
<221> NAME/KEY: misc_feature
<222> LOCATION: (1)..(29)
<223> OTHER INFORMATION: Description of Artificial Sequence: Synthetic
      primer

<400> SEQUENCE: 13
atcccgggtc cgtagatacc aaggctggt                                       29

<210> SEQ ID NO 14
<211> LENGTH: 34
<212> TYPE: DNA
<213> ORGANISM: Artificial Sequence
<220> FEATURE:
<221> NAME/KEY: misc_feature
<222> LOCATION: (1)..(34)
<223> OTHER INFORMATION: Description of Artificial Sequence: Synthetic
      primer

<400> SEQUENCE: 14
gcgttaactc gtcgctctta aacaccgagc taag                                 34

<210> SEQ ID NO 15
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: Description of Artificial Sequence: Synthetic
      primer

<400> SEQUENCE: 15
gcgctgcaga tttcatttgg agaggacacg                                      30

<210> SEQ ID NO 16
<211> LENGTH: 35
<212> TYPE: DNA
<213> ORGANISM: Artificial Sequence
<220> FEATURE:
<221> NAME/KEY: misc_feature
<222> LOCATION: (1)..(35)
<223> OTHER INFORMATION: Description of Artificial Sequence: Synthetic
      primer

<400> SEQUENCE: 16
cgcggccggc ctcagaagaa ctcgtcaaga aggcg                                35

<210> SEQ ID NO 17
<211> LENGTH: 38
<212> TYPE: DNA
<213> ORGANISM: Artificial Sequence
<220> FEATURE:
<221> NAME/KEY: misc_feature
<222> LOCATION: (1)..(38)
<223> OTHER INFORMATION: Description of Artificial Sequence: Synthetic
      oligonucleotide
```

```
<400> SEQUENCE: 17
ggaattccag ctgaccacca tggcaattcc cggggatc                           38

<210> SEQ ID NO 18
<211> LENGTH: 25
<212> TYPE: DNA
<213> ORGANISM: Artificial Sequence
<220> FEATURE:
<221> NAME/KEY: misc_feature
<222> LOCATION: (1)..(25)
<223> OTHER INFORMATION: Description of Artificial Sequence: Synthetic
      primer

<400> SEQUENCE: 18
gctgacacgc caagcctcgc tagtc                                         25

<210> SEQ ID NO 19
<211> LENGTH: 34
<212> TYPE: DNA
<213> ORGANISM: Artificial Sequence
<220> FEATURE:
<221> NAME/KEY: misc_feature
<222> LOCATION: (1)..(34)
<223> OTHER INFORMATION: Description of Artificial Sequence: Synthetic
      primer

<400> SEQUENCE: 19
gcgttaactc gtcgctctta aacaccgagc taag                               34

<210> SEQ ID NO 20
<211> LENGTH: 29
<212> TYPE: DNA
<213> ORGANISM: Artificial Sequence
<220> FEATURE:
<221> NAME/KEY: misc_feature
<222> LOCATION: (1)..(29)
<223> OTHER INFORMATION: Description of Artificial Sequence: Synthetic
      primer

<400> SEQUENCE: 20
atcccgggtc cgtagatacc aaggctggt                                     29

<210> SEQ ID NO 21
<211> LENGTH: 34
<212> TYPE: DNA
<213> ORGANISM: Artificial Sequence
<220> FEATURE:
<221> NAME/KEY: misc_feature
<222> LOCATION: (1)..(34)
<223> OTHER INFORMATION: Description of Artificial Sequence: Synthetic
      primer

<400> SEQUENCE: 21
gcgttaactc gtcgctctta aacaccgagc taag                               34

<210> SEQ ID NO 22
<211> LENGTH: 32
<212> TYPE: DNA
<213> ORGANISM: Artificial Sequence
<220> FEATURE:
<221> NAME/KEY: misc_feature
<222> LOCATION: (1)..(32)
<223> OTHER INFORMATION: Description of Artificial Sequence: Synthetic
      primer

<400> SEQUENCE: 22
gcgagctcca caccaatctc cagactccac ca                                 32
```

```
<210> SEQ ID NO 23
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: Description of Artificial Sequence: Synthetic
      primer

<400> SEQUENCE: 23
atcccgggag atagcccaga aggccgatcc                                            30

<210> SEQ ID NO 24
<211> LENGTH: 193
<212> TYPE: PRT
<213> ORGANISM: Hordeum vulgare

<400> SEQUENCE: 24

Met Phe Leu Val Asp Trp Phe Tyr Gly Val Leu Ala Ser Leu Gly Leu
1               5                   10                  15

Trp Gln Lys Glu Ala Lys Ile Leu Phe Leu Gly Leu Asp Asn Ala Gly
            20                  25                  30

Lys Thr Thr Leu Leu His Met Leu Lys Asp Glu Arg Leu Val Gln His
        35                  40                  45

Gln Pro Thr Gln Tyr Pro Thr Ser Glu Glu Leu Ser Ile Gly Lys Ile
    50                  55                  60

Lys Phe Lys Ala Phe Asp Leu Gly Gly His Gln Ile Ala Arg Arg Val
65                  70                  75                  80

Trp Lys Asp Tyr Tyr Ala Lys Val Asp Ala Val Val Tyr Leu Val Asp
                85                  90                  95

Ala Tyr Asp Lys Glu Arg Phe Ala Glu Ser Lys Lys Glu Leu Asp Ala
            100                 105                 110

Leu Leu Ser Asp Asp Ser Leu Ala Thr Val Pro Phe Leu Ile Leu Gly
        115                 120                 125

Asn Lys Ile Asp Ile Pro Tyr Ala Ala Ser Glu Glu Glu Leu Arg Tyr
    130                 135                 140

His Leu Gly Leu Ser Asn Phe Thr Thr Gly Lys Gly Lys Val Ser Leu
145                 150                 155                 160

Ser Glu Ser Asn Val Arg Pro Leu Glu Val Phe Met Cys Ser Ile Val
                165                 170                 175

Arg Lys Met Gly Tyr Gly Glu Gly Phe Lys Trp Met Ser Gln Tyr Ile
            180                 185                 190

Lys

<210> SEQ ID NO 25
<211> LENGTH: 193
<212> TYPE: PRT
<213> ORGANISM: Arabidopsis thaliana

<400> SEQUENCE: 25

Met Phe Met Ile Asp Trp Phe Tyr Gly Val Leu Ala Ser Leu Gly Leu
1               5                   10                  15

Trp Gln Lys Glu Ala Lys Ile Leu Phe Leu Gly Leu Asp Asn Ala Gly
            20                  25                  30

Lys Thr Thr Leu Leu His Met Leu Lys Asp Glu Arg Leu Val Gln His
        35                  40                  45
```

```
Gln Pro Thr Gln His Pro Thr Ser Glu Glu Leu Ser Ile Gly Lys Ile
         50                  55                  60

Lys Phe Lys Ala Phe Asp Leu Gly Gly His Gln Ile Ala Arg Arg Val
 65                  70                  75                  80

Trp Lys Asp Tyr Tyr Ala Lys Val Asp Ala Val Val Tyr Leu Val Asp
                 85                  90                  95

Ala Tyr Asp Lys Glu Arg Phe Ala Glu Ser Lys Lys Glu Leu Asp Ala
                100                 105                 110

Leu Leu Ser Asp Glu Ser Leu Ala Ser Val Pro Phe Leu Ile Leu Gly
                115                 120                 125

Asn Lys Ile Asp Ile Pro Tyr Ala Ala Ser Glu Asp Glu Leu Arg Tyr
            130                 135                 140

His Leu Gly Leu Ser Asn Phe Thr Thr Gly Lys Gly Lys Val Asn Leu
145                 150                 155                 160

Thr Asp Ser Asn Val Arg Pro Leu Glu Val Phe Met Cys Ser Ile Val
                165                 170                 175

Arg Lys Met Gly Tyr Gly Glu Gly Phe Lys Trp Val Ser Gln Tyr Ile
                180                 185                 190

Lys
```

<210> SEQ ID NO 26
<211> LENGTH: 193
<212> TYPE: PRT
<213> ORGANISM: Arabidopsis thaliana

<400> SEQUENCE: 26

```
Met Phe Leu Phe Asp Trp Phe Tyr Gly Ile Leu Ala Ser Leu Gly Leu
 1               5                  10                  15

Trp Gln Lys Glu Ala Lys Ile Leu Phe Leu Gly Leu Asp Asn Ala Gly
                20                  25                  30

Lys Thr Thr Leu Leu His Met Leu Lys Asp Glu Arg Leu Val Gln His
                35                  40                  45

Gln Pro Thr Gln His Pro Thr Ser Glu Glu Leu Ser Ile Gly Lys Ile
         50                  55                  60

Lys Phe Lys Ala Phe Asp Leu Gly Gly His Gln Ile Ala Arg Arg Val
 65                  70                  75                  80

Trp Lys Asp Tyr Tyr Ala Lys Val Asp Ala Val Val Tyr Leu Val Asp
                 85                  90                  95

Ala Tyr Asp Lys Glu Arg Phe Ala Glu Ser Lys Arg Glu Leu Asp Ala
                100                 105                 110

Leu Leu Ser Asp Glu Ala Leu Ala Thr Val Pro Phe Leu Ile Leu Gly
                115                 120                 125

Asn Lys Ile Asp Ile Pro Tyr Ala Ala Ser Glu Asp Glu Leu Arg Tyr
            130                 135                 140

His Leu Gly Leu Thr Asn Phe Thr Thr Gly Lys Gly Lys Val Thr Leu
145                 150                 155                 160

Gly Asp Ser Gly Val Arg Pro Leu Glu Val Phe Met Cys Ser Ile Val
                165                 170                 175

Arg Lys Met Gly Tyr Gly Glu Gly Phe Lys Trp Leu Ser Gln Tyr Ile
                180                 185                 190

Asn
```

<210> SEQ ID NO 27
<211> LENGTH: 191
<212> TYPE: PRT

<213> ORGANISM: Arabidopsis thaliana

<400> SEQUENCE: 27

```
Met Ile Asp Trp Phe Tyr Gly Val Leu Ala Ser Leu Gly Leu Trp Gln
1               5                   10                  15

Lys Glu Ala Lys Ile Leu Phe Leu Gly Leu Asp Asn Ala Gly Lys Thr
            20                  25                  30

Thr Leu Leu His Met Leu Lys Asp Glu Arg Leu Val Gln His Gln Pro
        35                  40                  45

Thr Gln His Pro Thr Ser Glu Glu Leu Ser Ile Gly Lys Ile Lys Phe
    50                  55                  60

Lys Ala Phe Asp Leu Gly Gly His Gln Ile Ala Arg Arg Val Trp Lys
65                  70                  75                  80

Asp Tyr Tyr Ala Lys Val Asp Ala Val Val Tyr Leu Val Asp Ala Tyr
                85                  90                  95

Asp Lys Glu Arg Phe Ala Glu Ser Lys Lys Glu Leu Asp Ala Leu Leu
            100                 105                 110

Ser Asp Glu Ser Leu Ala Ser Val Pro Phe Leu Ile Leu Gly Asn Lys
        115                 120                 125

Ile Asp Ile Pro Tyr Ala Ala Ser Glu Asp Glu Leu Arg Tyr His Leu
    130                 135                 140

Gly Leu Ser Asn Phe Thr Thr Gly Lys Gly Lys Val Asn Leu Thr Asp
145                 150                 155                 160

Ser Asn Val Arg Pro Leu Glu Val Phe Met Cys Ser Ile Val Arg Lys
                165                 170                 175

Met Gly Tyr Gly Glu Gly Phe Lys Trp Val Ser Gln Tyr Ile Lys
            180                 185                 190
```

<210> SEQ ID NO 28
<211> LENGTH: 300
<212> TYPE: PRT
<213> ORGANISM: Zea mays
<220> FEATURE:
<221> NAME/KEY: MOD_RES
<222> LOCATION: (186)..(187)
<223> OTHER INFORMATION: Variable amino acid

<400> SEQUENCE: 28

```
Met Val Gln Ser Lys Arg Val Tyr Met Gln His Ser Leu Ala Ser Leu
1               5                   10                  15

Arg Leu Glu Trp Ser Arg His Pro Asp Pro Ala Ala Val Asn Arg
            20                  25                  30

His Ala Pro Ile Leu Pro Gln Gln Thr Gln His Lys Gln Thr Gly Arg
        35                  40                  45

Asp Ser Asp Pro Leu Val Thr His Pro Arg Tyr Pro Leu Ser Leu Gly
    50                  55                  60

Phe Leu Ser His His Gln Pro Pro Ser Arg Leu Ser Pro Pro Pro
65                  70                  75                  80

Ala Leu Gly Arg Arg Asp Glu Gly Arg Glu Ala Pro Ala Gly Arg
                85                  90                  95

Gly Gly Lys Arg Ser Ser Arg Ala Gly Gly Glu Met Phe Leu Trp Asp
            100                 105                 110

Trp Phe Tyr Gly Val Leu Ala Ser Leu Gly Leu Trp Gln Lys Glu Ala
        115                 120                 125

Lys Ile Leu Phe Leu Cys Leu Asp Asn Ala Gly Lys Thr Thr Leu Leu
    130                 135                 140
```

```
His Met Leu Lys Asp Glu Arg Leu Val Gln His Gln Pro Thr Gln His
145                 150                 155                 160

Pro Thr Ser Glu Glu Leu Ser Ile Gly Lys Ile Lys Phe Lys Ala Phe
            165                 170                 175

Asp Leu Gly Gly His Gln Ile Ala Arg Xaa Xaa Trp Lys Asp Tyr Tyr
        180                 185                 190

Ala Lys Val Asp Ala Val Val Tyr Leu Val Asp Ala Tyr Asp Lys Glu
        195                 200                 205

Arg Phe Ala Glu Ser Lys Lys Glu Leu Asp Ala Leu Leu Ser Asp Asp
    210                 215                 220

Ser Leu Ala Asn Val Pro Phe Leu Ile Leu Gly Asn Lys Ile Asp Ile
225                 230                 235                 240

Pro Tyr Ala Ala Ser Glu Glu Glu Leu Arg Tyr His Leu Gly Leu Ser
                245                 250                 255

Asn Phe Thr Thr Gly Lys Gly Lys Val Asn Leu Gly Asp Ser Asn Val
            260                 265                 270

Arg Pro Leu Glu Val Phe Met Cys Ser Val Val Arg Lys Met Gly Tyr
        275                 280                 285

Gly Asp Gly Phe Lys Trp Val Ser Gln Tyr Ile Lys
290                 295                 300

<210> SEQ ID NO 29
<211> LENGTH: 305
<212> TYPE: PRT
<213> ORGANISM: Zea mays
<220> FEATURE:
<221> NAME/KEY: MOD_RES
<222> LOCATION: (191)..(192)
<223> OTHER INFORMATION: Variable amino acid

<400> SEQUENCE: 29

Phe Ser Ile Asp Thr Met Val Gln Ser Lys Arg Val Tyr Met Gln His
1               5                   10                  15

Ser Leu Ala Ser Leu Arg Leu Glu Trp Ser Arg His Pro Asp Pro Ala
            20                  25                  30

Ala Ala Val Asn Arg His Ala Pro Ile Leu Pro Gln Gln Thr Gln His
        35                  40                  45

Lys Gln Thr Gly Arg Asp Ser Asp Pro Leu Val Thr His Pro Arg Tyr
    50                  55                  60

Pro Leu Ser Leu Gly Phe Leu Ser His His Gln Pro Pro Ser Arg Leu
65                  70                  75                  80

Ser Pro Pro Pro Ala Leu Gly Arg Arg Asp Glu Gly Arg Arg Glu
                85                  90                  95

Ala Pro Ala Gly Arg Gly Gly Lys Arg Ser Ser Arg Ala Gly Gly Glu
            100                 105                 110

Met Phe Leu Trp Asp Trp Phe Tyr Gly Val Leu Ala Ser Leu Gly Leu
        115                 120                 125

Trp Gln Lys Glu Ala Lys Ile Leu Phe Leu Cys Leu Asp Asn Ala Gly
    130                 135                 140

Lys Thr Thr Leu Leu His Met Leu Lys Asp Glu Arg Leu Val Gln His
145                 150                 155                 160

Gln Pro Thr Gln His Pro Thr Ser Glu Glu Leu Ser Ile Gly Lys Ile
                165                 170                 175

Lys Phe Lys Ala Phe Asp Leu Gly Gly His Gln Ile Ala Arg Xaa Xaa
            180                 185                 190

Trp Lys Asp Tyr Tyr Ala Lys Val Asp Ala Val Val Tyr Leu Val Asp
```

```
              195                 200                 205
Ala Tyr Asp Lys Glu Arg Phe Ala Glu Ser Lys Lys Glu Leu Asp Ala
    210                 215                 220

Leu Leu Ser Asp Asp Ser Leu Ala Asn Val Pro Phe Leu Ile Leu Gly
225                 230                 235                 240

Asn Lys Ile Asp Ile Pro Tyr Ala Ala Ser Glu Glu Leu Arg Tyr
                245                 250                 255

His Leu Gly Leu Ser Asn Phe Thr Thr Gly Lys Gly Lys Val Asn Leu
                260                 265                 270

Gly Asp Ser Asn Val Arg Pro Leu Glu Val Phe Met Cys Ser Val Val
                275                 280                 285

Arg Lys Met Gly Tyr Gly Asp Gly Phe Lys Trp Val Ser Gln Tyr Ile
            290                 295                 300

Lys
305

<210> SEQ ID NO 30
<211> LENGTH: 292
<212> TYPE: PRT
<213> ORGANISM: Zea mays
<220> FEATURE:
<221> NAME/KEY: MOD_RES
<222> LOCATION: (178)..(179)
<223> OTHER INFORMATION: Variable amino acid

<400> SEQUENCE: 30

Met Gln His Ser Leu Ala Ser Leu Arg Leu Glu Trp Ser Arg His Pro
1               5                   10                  15

Asp Pro Ala Ala Val Asn Arg His Ala Pro Ile Leu Pro Gln Gln
            20                  25                  30

Thr Gln His Lys Gln Thr Gly Arg Asp Ser Asp Pro Leu Val Thr His
                35                  40                  45

Pro Arg Tyr Pro Leu Ser Leu Gly Phe Leu Ser His Gln Pro Pro
    50                  55                  60

Ser Arg Leu Ser Pro Pro Pro Ala Leu Gly Arg Arg Asp Glu Gly
65                  70                  75                  80

Arg Arg Glu Ala Pro Ala Gly Arg Gly Gly Lys Arg Ser Ser Arg Ala
                85                  90                  95

Gly Gly Glu Met Phe Leu Trp Asp Trp Phe Tyr Gly Val Leu Ala Ser
            100                 105                 110

Leu Gly Leu Trp Gln Lys Glu Ala Lys Ile Leu Phe Leu Cys Leu Asp
        115                 120                 125

Asn Ala Gly Lys Thr Thr Leu Leu His Met Leu Lys Asp Glu Arg Leu
    130                 135                 140

Val Gln His Gln Pro Thr Gln His Pro Thr Ser Glu Glu Leu Ser Ile
145                 150                 155                 160

Gly Lys Ile Lys Phe Lys Ala Phe Asp Leu Gly Gly His Gln Ile Ala
                165                 170                 175

Arg Xaa Xaa Trp Lys Asp Tyr Tyr Ala Lys Val Asp Ala Val Val Tyr
            180                 185                 190

Leu Val Asp Ala Tyr Asp Lys Glu Arg Phe Ala Glu Ser Lys Lys Glu
        195                 200                 205

Leu Asp Ala Leu Leu Ser Asp Ser Leu Ala Asn Val Pro Phe Leu
    210                 215                 220

Ile Leu Gly Asn Lys Ile Asp Ile Pro Tyr Ala Ala Ser Glu Glu Glu
225                 230                 235                 240
```

```
Leu Arg Tyr His Leu Gly Leu Ser Asn Phe Thr Thr Gly Lys Gly Lys
            245                 250                 255

Val Asn Leu Gly Asp Ser Asn Val Arg Pro Leu Glu Val Phe Met Cys
            260                 265                 270

Ser Val Val Arg Lys Met Gly Tyr Gly Asp Gly Phe Lys Trp Val Ser
            275                 280                 285

Gln Tyr Ile Lys
        290

<210> SEQ ID NO 31
<211> LENGTH: 193
<212> TYPE: PRT
<213> ORGANISM: Arabidopsis thaliana

<400> SEQUENCE: 31

Met Phe Leu Phe Asp Trp Phe Tyr Gly Ile Leu Ala Ser Leu Gly Leu
1               5                   10                  15

Cys Lys Lys Glu Ala Lys Ile Leu Phe Leu Gly Leu Asp Asn Ala Gly
            20                  25                  30

Lys Thr Thr Leu Leu His Met Leu Lys Asp Glu Arg Leu Val Gln His
            35                  40                  45

Gln Pro Thr Gln His Pro Thr Ser Glu Glu Leu Ser Ile Gly Lys Ile
        50                  55                  60

Asn Phe Lys Ala Phe Asp Leu Gly Gly His Gln Ile Ala Arg Arg Val
65                  70                  75                  80

Trp Lys Asp Cys Tyr Ala Lys Val Asp Ala Val Val Tyr Leu Val Asp
                85                  90                  95

Ala Tyr Asp Arg Asp Arg Phe Val Glu Ser Lys Arg Glu Leu Asp Ala
            100                 105                 110

Leu Leu Ser Asp Glu Ala Leu Ala Asn Val Pro Cys Leu Ile Leu Gly
            115                 120                 125

Asn Lys Ile Asp Ile Pro Tyr Ala Ser Ser Glu Asp Glu Leu Arg Tyr
        130                 135                 140

Tyr Leu Gly Leu Thr Asn Phe Thr Thr Gly Lys Gly Ile Val Asn Leu
145                 150                 155                 160

Glu Asp Ser Gly Val Arg Pro Leu Glu Val Phe Met Cys Ser Ile Val
                165                 170                 175

Arg Lys Met Gly Tyr Gly Glu Gly Phe Lys Trp Leu Ser Gln Tyr Ile
            180                 185                 190

Lys

<210> SEQ ID NO 32
<211> LENGTH: 258
<212> TYPE: PRT
<213> ORGANISM: Arabidopsis thaliana

<400> SEQUENCE: 32

Met Asn Phe Asn Leu Leu His Tyr Trp Ala Phe Ala His Ile Ile Ile
1               5                   10                  15

Gln Gly Pro Asn Thr Glu Ser Pro Leu Val Asn Arg Glu Arg Lys
            20                  25                  30

Ser Glu Lys Arg Glu Arg Asp Leu Trp Leu Cys Ile Ala Arg Cys Ser
            35                  40                  45

Ser Ser His Arg Ser Lys Thr Met Asn Pro Glu Tyr Asp Tyr Leu Phe
        50                  55                  60
```

```
Lys Leu Leu Leu Ile Gly Asp Ser Gly Val Gly Lys Ser Cys Leu Leu
 65                  70                  75                  80

Leu Arg Phe Ser Asp Asp Ser Tyr Val Glu Ser Tyr Ile Ser Thr Ile
                 85                  90                  95

Gly Val Asp Phe Lys Ile Arg Thr Val Glu Gln Asp Gly Lys Thr Ile
            100                 105                 110

Lys Leu Gln Ile Trp Asp Thr Ala Gly Gln Glu Arg Phe Arg Thr Ile
        115                 120                 125

Thr Ser Ser Tyr Tyr Arg Gly Ala His Gly Ile Ile Ile Val Tyr Asp
    130                 135                 140

Val Thr Asp Glu Glu Ser Phe Asn Asn Val Lys Gln Trp Leu Ser Glu
145                 150                 155                 160

Ile Asp Arg Tyr Ala Ser Asp Asn Val Asn Lys Leu Leu Val Gly Asn
                165                 170                 175

Lys Ser Asp Leu Thr Glu Asn Arg Ala Ile Pro Tyr Glu Thr Ala Lys
            180                 185                 190

Ala Phe Ala Asp Glu Ile Gly Ile Pro Phe Met Glu Thr Ser Ala Lys
        195                 200                 205

Asp Ala Thr Asn Val Glu Gln Ala Phe Met Ala Met Ser Ala Ser Ile
    210                 215                 220

Lys Glu Arg Met Ala Ser Gln Pro Ala Gly Asn Asn Ala Arg Pro Pro
225                 230                 235                 240

Thr Val Gln Ile Arg Gly Gln Pro Val Ala Gln Lys Asn Gly Cys Cys
                245                 250                 255

Ser Thr

<210> SEQ ID NO 33
<211> LENGTH: 203
<212> TYPE: PRT
<213> ORGANISM: Arabidopsis thaliana

<400> SEQUENCE: 33

Met Asn Pro Glu Tyr Asp Tyr Leu Phe Lys Leu Leu Leu Ile Gly Asp
1               5                   10                  15

Ser Gly Val Gly Lys Ser Cys Leu Leu Leu Arg Phe Ser Asp Asp Ser
            20                  25                  30

Tyr Val Glu Ser Tyr Ile Ser Thr Ile Gly Val Asp Phe Lys Ile Arg
        35                  40                  45

Thr Val Glu Gln Asp Gly Lys Thr Ile Lys Leu Gln Ile Trp Asp Thr
    50                  55                  60

Ala Gly Gln Glu Arg Phe Arg Thr Ile Thr Ser Ser Tyr Tyr Arg Gly
65                  70                  75                  80

Ala His Gly Ile Ile Ile Val Tyr Asp Val Thr Asp Glu Glu Ser Phe
                85                  90                  95

Asn Asn Val Lys Gln Trp Leu Ser Glu Ile Asp Arg Tyr Ala Ser Asp
            100                 105                 110

Asn Val Asn Lys Leu Leu Val Gly Asn Lys Ser Asp Leu Thr Glu Asn
        115                 120                 125

Arg Ala Ile Pro Tyr Glu Thr Ala Lys Ala Phe Ala Asp Glu Ile Gly
    130                 135                 140

Ile Pro Phe Met Glu Thr Ser Ala Lys Asp Ala Thr Asn Val Glu Gln
145                 150                 155                 160

Ala Phe Met Ala Met Ser Ala Ser Ile Lys Glu Arg Met Ala Ser Gln
                165                 170                 175
```

```
                    -continued
Pro Ala Gly Asn Asn Ala Arg Pro Pro Thr Val Gln Ile Arg Gly Gln
            180                 185                 190

Pro Val Ala Gln Lys Asn Gly Cys Cys Ser Thr
        195                 200
```